United States Patent
Garcia et al.

(10) Patent No.: US 12,005,079 B2
(45) Date of Patent: *Jun. 11, 2024

(54) BIOLOGICALLY RELEVANT ORTHOGONAL CYTOKINE/RECEPTOR PAIRS

(71) Applicants: The Board of Trustees of the Leland Stanford Junior University, Stanford, CA (US); University of Washington, Seattle, WA (US)

(72) Inventors: Kenan Christopher Garcia, Menlo Park, CA (US); Jonathan Sockolosky, San Francisco, CA (US); Lora Picton, Foster City, CA (US)

(73) Assignees: The Board of Trustees of the Leland Stanford Junior University, Stanford, CA (US); University of Washington, Seattle, WA (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/953,000

(22) Filed: Nov. 19, 2020

(65) Prior Publication Data

US 2021/0069243 A1    Mar. 11, 2021

Related U.S. Application Data

(63) Continuation of application No. 15/916,689, filed on Mar. 9, 2018, now Pat. No. 10,869,887, which is a continuation-in-part of application No. PCT/US2016/050511, filed on Sep. 7, 2016.

(60) Provisional application No. 62/375,089, filed on Aug. 15, 2016, provisional application No. 62/217,364, filed on Sep. 11, 2015.

(51) Int. Cl.
| | |
|---|---|
| *A61K 38/17* | (2006.01) |
| *A61K 35/17* | (2015.01) |
| *A61K 38/20* | (2006.01) |
| *C07K 14/55* | (2006.01) |
| *C12N 5/0783* | (2010.01) |
| *C12N 15/10* | (2006.01) |
| *A61K 39/00* | (2006.01) |

(52) U.S. Cl.
CPC .......... *A61K 35/17* (2013.01); *A61K 38/1793* (2013.01); *A61K 38/2013* (2013.01); *C07K 14/55* (2013.01); *C12N 5/0638* (2013.01); *C12N 15/1034* (2013.01); *A61K 2039/5156* (2013.01); *A61K 2300/00* (2013.01); *C12N 2740/10043* (2013.01)

(58) Field of Classification Search
CPC ............................ A61K 38/2013; C07K 14/55
See application file for complete search history.

(56) References Cited

U.S. PATENT DOCUMENTS

| | | | |
|---|---|---|---|
| 4,902,502 A | 2/1990 | Nitecki et al. | |
| 6,955,807 B1 | 10/2005 | Shanafelt et al. | |
| 7,981,398 B2 | 7/2011 | Chang et al. | |
| 10,869,887 B2 * | 12/2020 | Garcia | A61K 38/1793 |
| 2003/0166163 A1 * | 9/2003 | Gillies | C07K 14/55 |
| | | | 435/325 |
| 2003/0171267 A1 | 9/2003 | Rosen et al. | |
| 2006/0199250 A1 | 9/2006 | Zhao et al. | |
| 2011/0250213 A1 | 10/2011 | Tsao et al. | |
| 2013/0017168 A1 | 1/2013 | Gillies et al. | |
| 2014/0255360 A1 | 9/2014 | Spencer et al. | |
| 2014/0349402 A1 | 11/2014 | Cooper et al. | |
| 2015/0306141 A1 | 10/2015 | Jensen et al. | |
| 2020/0024319 A1 * | 1/2020 | Butz | A61P 37/06 |

FOREIGN PATENT DOCUMENTS

| | | | |
|---|---|---|---|
| CN | 101809032 | 8/2010 | |
| CN | 0107746831 | 3/2018 | |
| JP | 2002506980 | 3/2002 | |
| JP | 2005511707 | 4/2008 | |
| JP | 2010-536923 | 12/2010 | |
| JP | 2016-519651 | 7/2016 | |
| JP | 2016-520074 | 7/2016 | |
| RU | 2312677 C2 | 12/2007 | |
| WO | WO1999/047178 | 9/1999 | |
| WO | WO1999047178 | 9/1999 | |
| WO | WO2003048334 | 12/2002 | |
| WO | WO 2005/086751 | 9/2005 | |
| WO | WO2014150600 | 9/2014 | |
| WO | WO2016025385 | 2/2016 | |
| WO | WO-2016164937 A2 * | 10/2016 | A61K 38/2013 |
| WO | WO2017044464 | 3/2017 | |

OTHER PUBLICATIONS

Marofi et al., (2021) "CAR T Cells in Solid Tumors: Challenges and Opportunities." Stem Cell Research & Therapy, vol. 12, No. 81, 16 pages.
Muller et al., (2008) "Spliceosomal Peptide P140 for Immunotherapy of Systemic Lupus Erythematosus: Results of an early phase II clinical trial." Arthritis & Rheumatism, vol. 58, No. 12, pp. 3873-3883.
Singer et al. (2018) "Genes and Genomes", vol. 1;2, 373, English Translated pp. 33-35.
Zhang et al., (2016) "New Strategies for the Treatment of Solid Tumors with CAR-T Cells." International Journal of Biological Sciences, vol. 12, No. 6, pp. 718-729.
Bork et al. (2000) "Powers and Pitfalls in Sequence Analysis: The 70% Hurdle" , Genome, pp. 398-400.
Bowie et al. (1990) "Deciphering the message in protein sequences: tolerance to amino acid substitutions" Science, ,247:1306-1310.

(Continued)

*Primary Examiner* — Vanessa L. Ford
*Assistant Examiner* — Sandra Dillahunt
(74) *Attorney, Agent, or Firm* — Pamela J. Sherwood; Bozicevic, Field & Francis LLP

(57) ABSTRACT

Engineered orthogonal cytokine receptor/ligand pairs, and methods of use thereof, are provided.

29 Claims, 34 Drawing Sheets

Figure 1A:
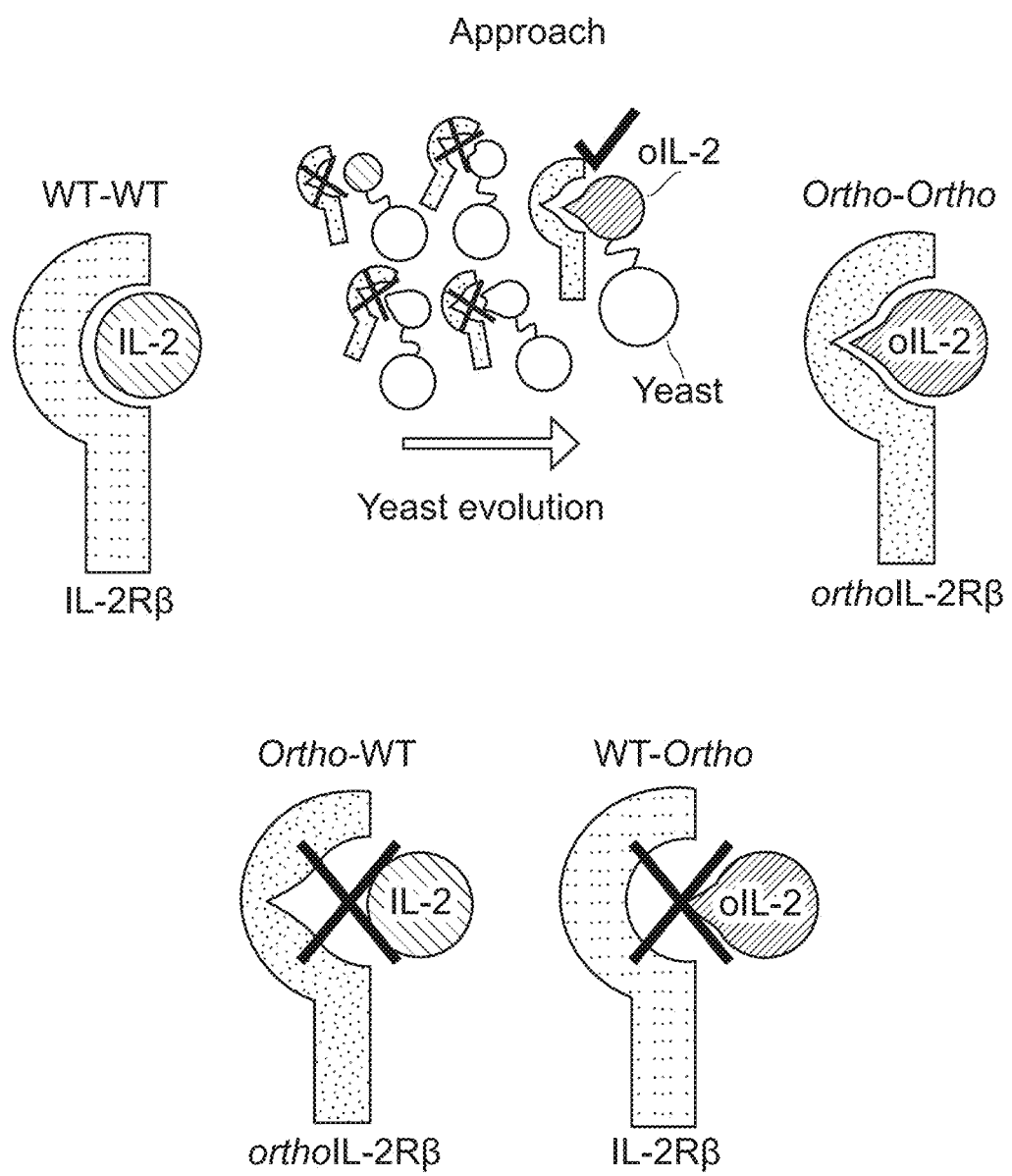

Specification includes a Sequence Listing.

(56) References Cited

OTHER PUBLICATIONS

Burgess et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" J. Cell Bioi. 111:2129-2138.

Calvello et al., "Conservation/Mutation in the Splice Sites of Cytokine Receptor Genes of Mouse and Human", Int J Evol Bioi., Oct. 26, 2013, pp. 1-10, vol. 2013, Article ID 818954, Hindawi Publishing Corporation, Cairo, Egypt.

Cochran et al., "Improved mutants from directed evolution are biased to orthologous substitutions", Protein Eng Des Sel., Jun. 1, 2006, pp. 245-253, vol. 19, Issue 6, Oxford University Press, Oxford, United Kingdom.

Lazar et al. "Transforming Growth Factor-α: Mutation of Aspartic Acid 47 and Leucine 48 Results in Different Biological Activities" Mol. Cell. Bioi., 8:1247-1252, 1988 (Year: 1988).

Mitra et al., "Interleukin-2 Activity Can be Fine Tuned with Engineered Receptor Signaling Clamps", Immunity, May 19, 2015, pp. 826-838, vol. 42, Issue 5, Elsevier, New York City, NY.

Ring et al, (2012) "Mechanistic and Structural Insight into the Functional Dichotomy between Interleukin-2 and Interleukin-15", Nat Immunol, Vo. 13, No. 12, p. 1187-1195.

Shi et al., "A Novel Cytokine Receptor-Ligand Pair", J Bioi Chern., Jun. 23, 2000, 2000, pp. 19167-19176, vol. 275(25), American Society for Biochemistry and Molecular Biology, Rockville, MD.

Wang et al., (2005) "Structure of the Quaternary Complex of interleukin-2 With Its α, β, and γc Receptors", Science, 2005, vol. 310, p. 1159-1163.

Ho et al., "Decoupling the Functional Pleiotropy of Stem Cell Factor by Tuning c-Kit Signaling", Cell, Mar. 10, 2017, pp. 1041-1052.e18, vol. 168, Issue 6, Elsevier, New York City, NY.

Imler et al., (1992) "Identification of three adjacent amino acids of interleukin-2 receptor chain which control the affinity and the specificity of the interaction with interleukin-2." The EMBO Journal, vol. 11, No. 6, pp. 2047-2053.

Sockolosky et al., (2018) "Selective targeting of engineered T cells using orthogonal IL-2 cytokine-receptor complexes." Science, vol. 359, No. 6379, pp. 1037-1042.

Kochenderfer et al (2013). "Donor-derived CD19-targeted T cells cause regression of malignancy persisting after allogeneic hematopoietic stem cell transplantation." *Blood, The Journal of the American Society of Hematology*, 122(25), pp. 4129-4139.

Kochenderfer et al (2009). "Construction and pre-clinical evaluation of an anti-CD19 chimeric antigen receptor." *Journal of immunotherapy (Hagerstown, MD.*: 1997), 32(7), pp. 689-702.

Lee et al (2008). "A novel strategy for rapid and efficient isolation of human tumor-specific CD4+ and CD8+ T-cell clones." *Journal of immunological methods*, 331(1-2), pp. 13-26.

Kitada et al (2018). "Programming gene and engineered-cell therapies with synthetic biology." *Science*, 359(6376), eaad1067.

Katre et al (1990). "Immunogenicity of recombinant IL-2 modified by covalent attachment of polyethylene glycol." *Journal of immunology (Baltimore, MD.*: 1950), 144(1), pp. 209-213.

Harris et al (2001). "Pegylation: a novel process for modifying pharmacokinetics." *Clinical pharmacokinetics*, 40, pp. 539-551.

Maude et al (2017). "The effect of pembrolizumab in combination with CD19-targeted chimeric antigen receptor (CAR) T cells in relapsed acute lymphoblastic leukemia (ALL)." *Special clinical science Symposia* 35(15).

Sequence alignment, 2024.

Jackson Laboratory Data Sheet, 2024.

\* cited by examiner

FIG. 3

Validated to disrupt wild-type IL-2 binding

| Sequence | 1 | 2 | 3 | 4 | 5 | 6 | 7 | 8 | 9 | 10 | ... | 70 | 71 | 72 | 73 | 74 | 75 | ... | 130 | 131 | 132 | 133 | 134 | 135 | 136 | 137 | 138 | 139 | ... | 212 | 213 | 214 | 215 |
|---|---|---|---|---|---|---|---|---|---|---|---|---|---|---|---|---|---|---|---|---|---|---|---|---|---|---|---|---|---|---|---|---|---|
| WT | A | V | K | N | C | S | H | L | E | C | ... | S | Q | S | L | T | S | ... | S | Q | V | S | H | Y | I | E | P | Y | ... | M | K | E | I |
| T74Y | A | V | K | N | C | S | H | L | E | C | ... | S | Q | S | L | Y | S | ... | S | Q | V | S | H | Y | I | E | P | Y | ... | M | K | E | I |
| H134D | A | V | K | N | C | S | H | L | E | C | ... | S | Q | S | L | T | S | ... | S | Q | V | S | D | Y | I | E | P | Y | ... | M | K | E | I |
| Y135F | A | V | K | N | C | S | H | L | E | C | ... | S | Q | S | L | T | S | ... | S | Q | V | S | H | F | I | E | P | Y | ... | M | K | E | I |
| H134D Y135F | A | V | K | N | C | S | H | L | E | C | ... | S | Q | S | L | T | S | ... | S | Q | V | S | D | F | I | E | P | Y | ... | M | K | E | I |
| Q71Y | A | V | K | N | C | S | H | L | E | C | ... | S | Y | S | L | T | S | ... | S | Q | V | S | H | Y | I | E | P | Y | ... | M | K | E | I |
| T74D | A | V | K | N | C | S | H | L | E | C | ... | S | Q | S | L | D | S | ... | S | Q | V | S | H | Y | I | E | P | Y | ... | M | K | E | I |
| H134E Y135E | A | V | K | N | C | S | H | L | E | C | ... | S | Q | S | L | T | S | ... | S | Q | V | S | E | E | I | E | P | Y | ... | M | K | E | I |
| H134K Y135R | A | V | K | N | C | S | H | L | E | C | ... | S | Q | S | L | T | S | ... | S | Q | V | S | K | R | I | E | P | Y | ... | M | K | E | I |

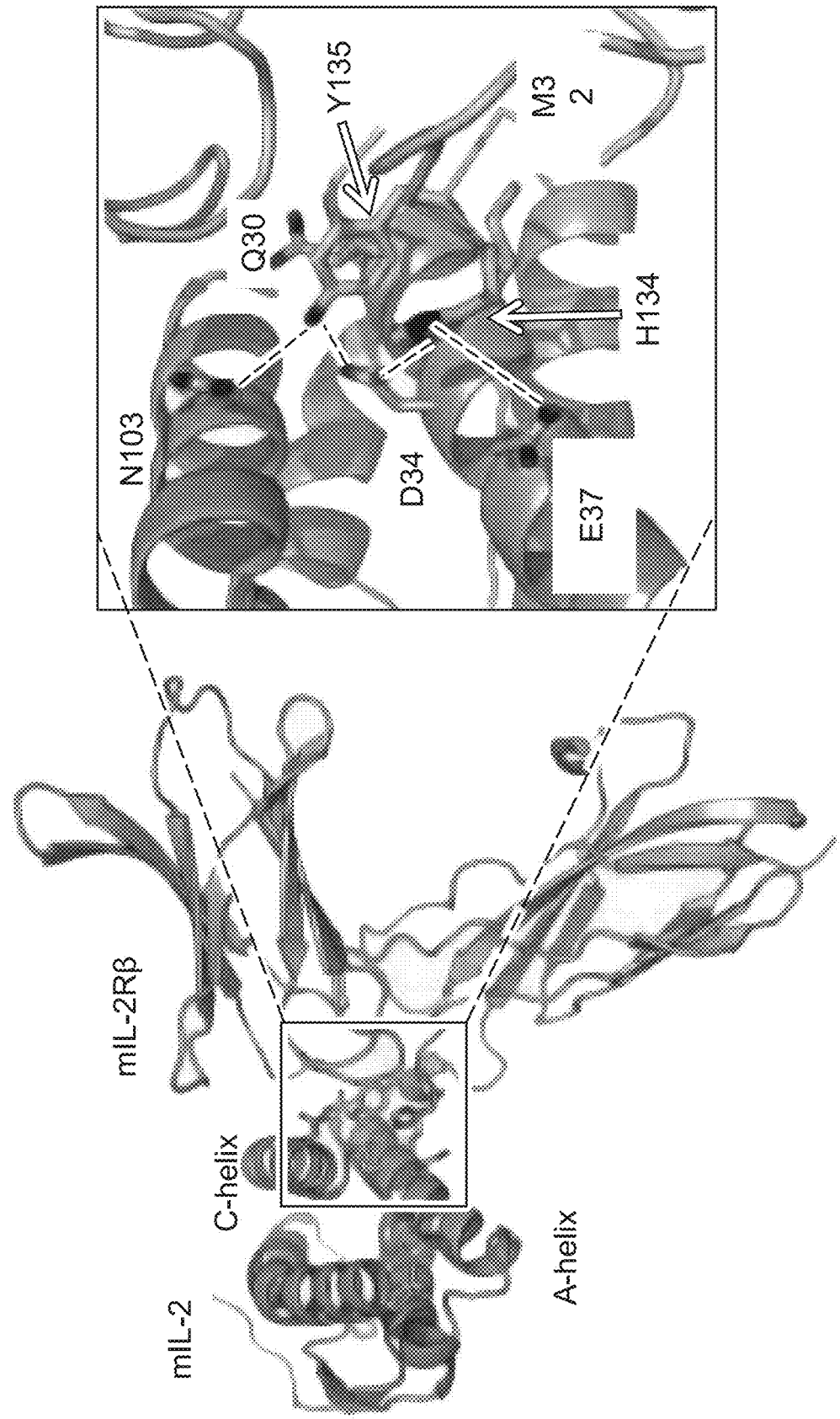

FIG. 6

| Sequence | 27 | 28 | 29 | 30 | 31 | 32 | 33 | 34 | 35 | 36 | 37 | 38 | 39 | 40 | 41 | 42 | 43 | 44 | 45 | ... | 100 | 101 | 102 | 103 | 104 | 105 | ... | 145 | 146 | 147 | 148 | 149 |
|---|---|---|---|---|---|---|---|---|---|---|---|---|---|---|---|---|---|---|---|---|---|---|---|---|---|---|---|---|---|---|---|---|
| WT IL-2 | H | L | E | Q | L | L | M | D | L | Q | E | L | L | S | R | M | E | N | Y | ... | F | I | S | N | I | R | ... | S | T | S | P | Q |
| 145 | H | M | E | N | L | L | V | L | L | Q | A | L | L | S | R | M | E | N | Y | ... | F | I | S | N | I | R | ... | S | T | S | P | Q |
| 146 | W | L | E | N | L | L | I | L | L | Q | W | L | L | S | R | M | E | N | Y | ... | F | I | S | N | I | R | ... | S | T | S | P | Q |
| 147 | H | W | E | N | L | L | V | L | L | Q | H | L | L | S | R | M | E | N | Y | ... | F | I | S | N | I | R | ... | S | T | S | P | Q |
| 148 | H | L | D | N | L | L | V | M | L | S | W | L | L | S | K | M | E | N | Y | ... | F | I | S | E | I | R | ... | S | T | S | P | Q |
| 149 | H | L | E | N | L | L | V | L | L | T | W | L | L | S | R | M | E | N | Y | ... | F | I | S | E | I | R | ... | S | T | S | P | Q |
| 150 | H | L | E | N | L | L | V | M | L | K | H | L | L | S | R | M | E | N | Y | ... | F | I | S | N | I | R | ... | S | T | S | P | Q |
| 151 | H | L | E | N | L | L | V | L | L | Q | Y | L | L | S | R | M | E | N | Y | ... | F | I | S | E | I | R | ... | S | T | S | P | Q |
| 157 | H | L | F | N | L | L | V | M | L | M | Y | L | L | S | R | M | E | N | Y | ... | F | I | S | N | I | R | ... | S | T | S | P | Q |
| 160 | H | L | Q | N | L | L | V | L | L | T | H | L | L | S | R | M | E | N | Y | ... | F | I | S | Q | I | R | ... | S | T | S | P | Q |
| 161 | H | L | D | N | L | L | V | M | L | Q | F | L | L | S | R | M | E | N | Y | ... | F | I | S | E | I | R | ... | S | T | S | P | Q |
| 162 | H | L | D | N | L | L | V | L | L | E | Y | L | L | S | R | M | E | N | Y | ... | F | I | S | N | I | R | ... | S | T | S | P | Q |
| 163 | H | L | D | N | L | L | A | M | L | T | V | L | L | S | R | M | E | N | Y | ... | F | I | S | Q | I | R | ... | S | T | S | P | Q |
| 165 | H | L | T | N | L | L | V | L | L | Q | H | L | L | S | R | M | E | N | Y | ... | F | I | S | N | I | R | ... | S | T | S | P | Q |
| 170 | H | L | E | N | L | L | V | L | L | Q | H | L | L | S | R | M | E | N | Y | ... | F | I | S | N | I | R | ... | S | T | S | P | Q |
| 172 | H | L | D | N | L | L | V | L | L | Q | Y | L | L | S | R | M | E | N | Y | ... | F | I | S | N | I | R | ... | S | T | S | P | Q |
| 175 | H | L | D | N | L | I | V | L | L | Q | A | L | L | S | R | M | E | N | Y | ... | F | I | S | N | I | R | ... | S | T | S | P | Q |
| 176 | H | L | D | N | L | L | V | L | L | Q | V | L | L | S | R | M | E | N | Y | ... | F | I | S | N | I | R | ... | S | T | S | P | Q |
| 177 | H | L | D | N | L | L | V | L | L | Q | H | L | L | S | R | M | E | N | Y | ... | F | I | S | N | I | R | ... | S | T | S | P | Q |
| 180 | H | L | D | N | L | L | V | L | L | K | A | L | L | S | R | M | E | N | Y | ... | F | I | S | N | I | R | ... | S | T | S | P | Q |
| 181 | H | L | D | N | L | L | V | L | L | E | L | L | L | S | R | M | E | N | Y | ... | F | I | S | N | I | R | ... | S | T | S | P | Q |
| 182 | H | L | D | N | L | L | V | L | L | Y | Y | L | L | S | R | M | E | N | Y | ... | F | I | S | N | I | R | ... | S | T | S | P | Q |
| 183 | H | L | A | N | L | L | V | L | L | E | H | L | L | S | R | M | E | N | Y | ... | F | I | S | N | I | R | ... | S | T | S | P | Q |

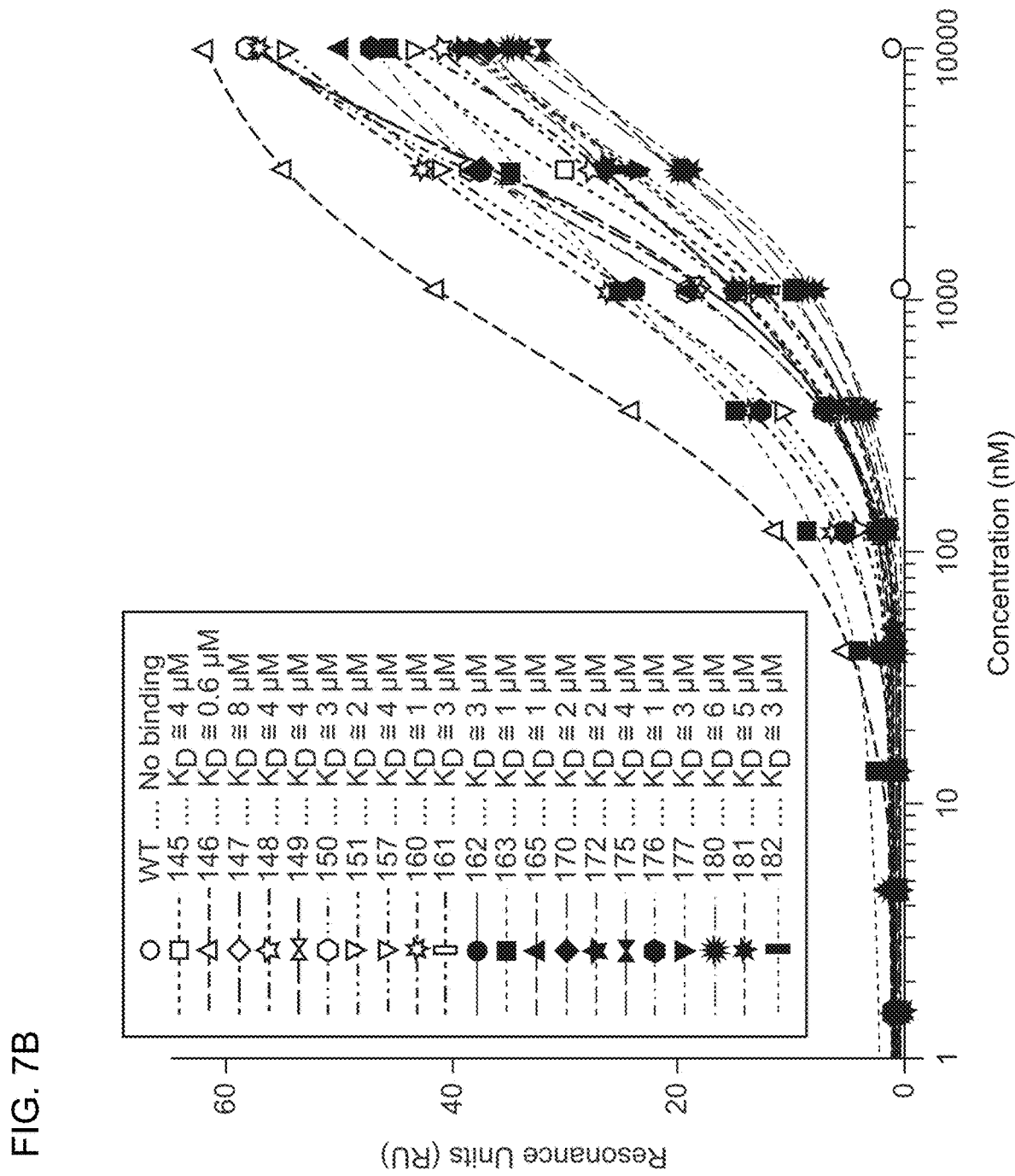

| IL-2 clone | CTLL-2 T cell line | | |
|---|---|---|---|
| | EC50 wild-type (pM) | EC50 ortho (pM) | WT / ortho |
| WT | 1.0 | 0.6 | 2 |
| 145 | 1021 | 20 | 51 |
| 146 | 40 | 2 | 17 |
| 147 | 15 | 1 | 14 |
| 148 | 4618 | 369 | 13 |
| 149 | 971 | 15 | 67 |
| 150 | 140 | 11 | 12 |
| 151 | 3382 | 53 | 64 |
| 157 | 129400 | 1543 | 84 |
| 160 | 16000 | 2021 | 8 |
| 161 | 19270 | 45760 | 0 |
| 162 | 80640 | 248 | 325 |
| 163 | 2104 | 1080 | 2 |
| 165 | 39780 | 21720 | 2 |
| 170 | 304 | 470 | 1 |
| 172 | 555 | 44 | 13 |
| 173 | 32830 | 9067 | 4 |
| 175 | 831 | 80 | 10 |
| 176 | 79220 | 15020 | 5 |
| 177 | 89150 | 345 | 258 |
| 180 | 1625 | 18 | 89 |
| 181 | 4555 | 67 | 68 |
| 182 | 5524 | 813 | 7 |
| 183 | 15400 | 1121 | 14 |

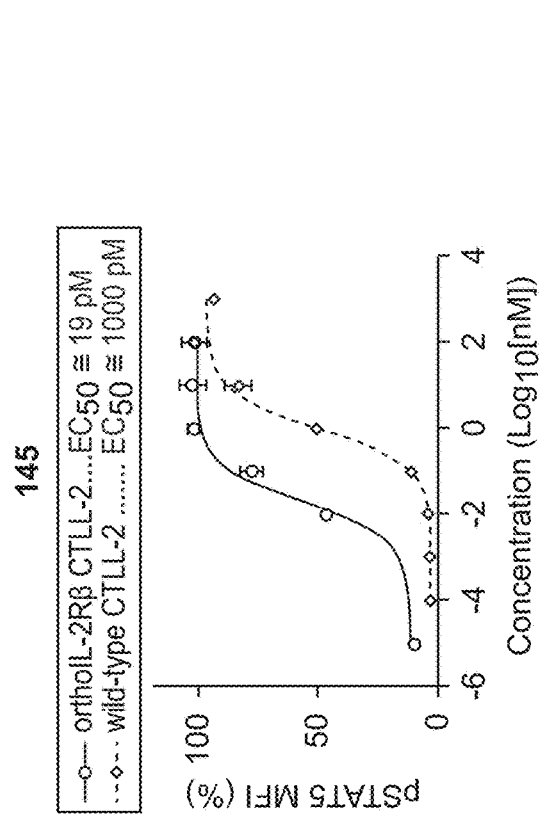
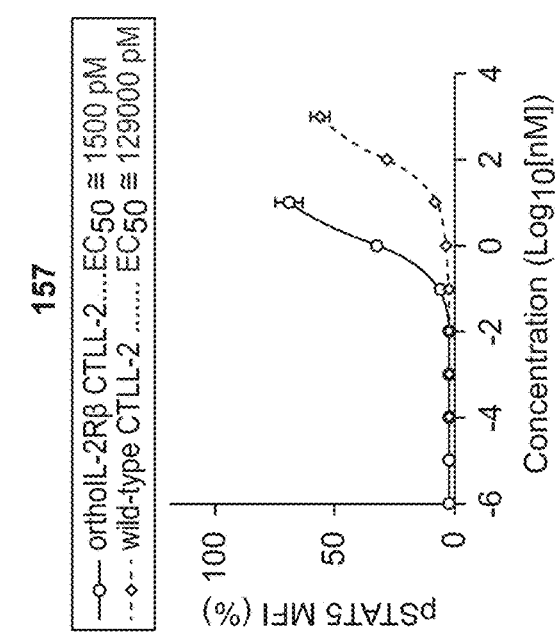
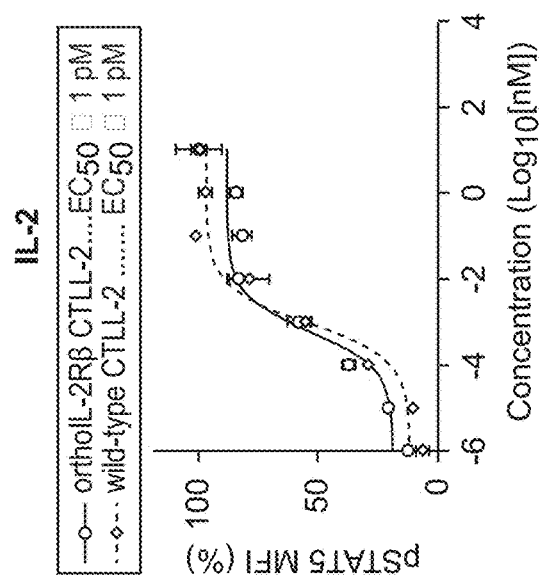
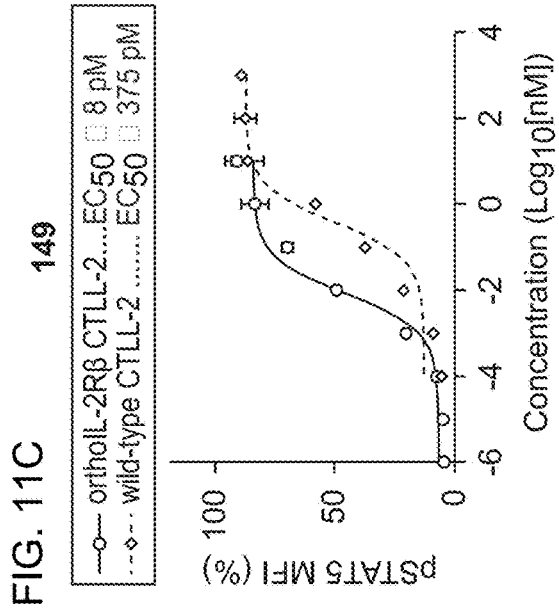

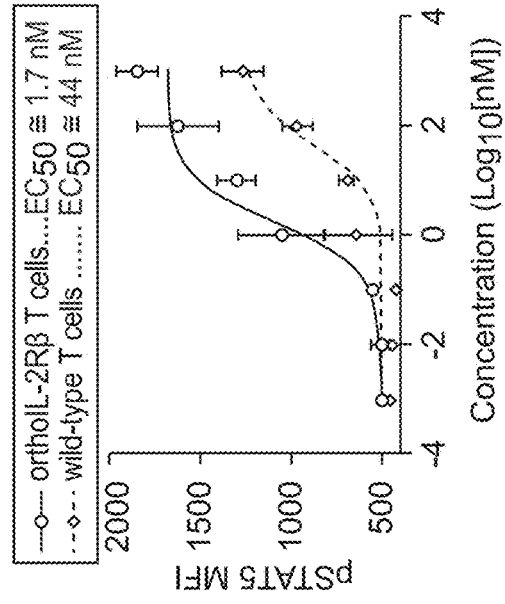
FIG. 13A
FIG. 13B
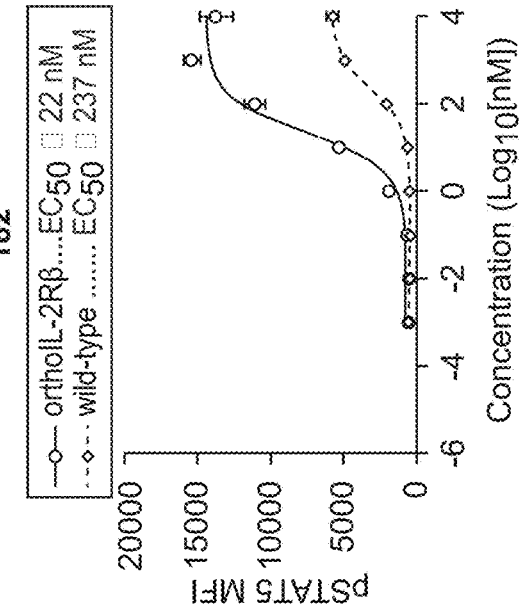
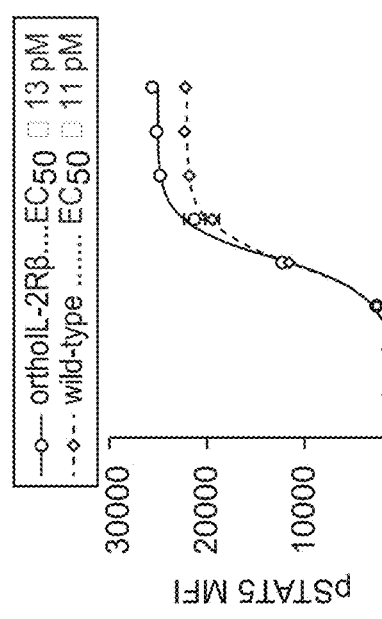
FIG. 13C
FIG. 13D
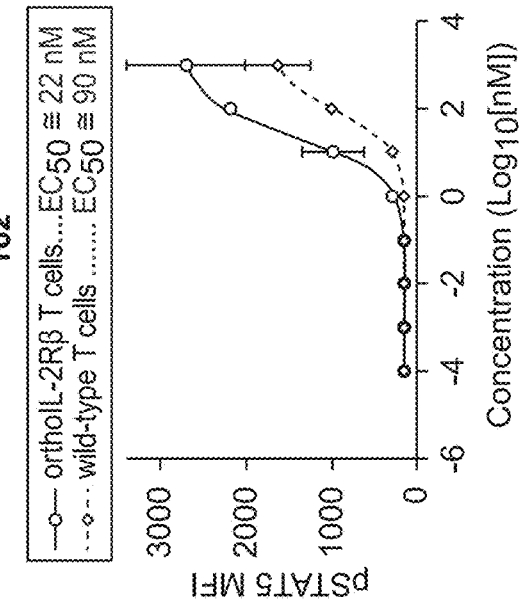

FIG. 15

```
IL2RB_HUMAN     1   AVNGTSQFTCFYNSRANISCVWSQDGALQDTSCQVHAWPDRRRWNQTCELLPVSQASWAC    60
IL2RB_MOUSE     1   AVKNCSHLECFYNSRANVSCMWSHEEALNVTTCHVHAKSNLRHWNKTCELTLVRQASWAC    60
                    *:.:  . **:******:**.*:**.:*:***:* * *:*..*.*** * * : ******

IL2RB_HUMAN    61   NLILGA-PDSQKLTTVDIVTLRVLCREGVRWRVMAIQDFKPFENLRLMAPISLQVVHVET   119
IL2RB_MOUSE    61   NLILGSFPESQSLTSVDLLDINVVCWEEKGWRRVKTCDFHPFDNLRIVAPHSLQVLHIDT   120
                    *****: *:**.**:**::.:.** *.:  *** *  ** **:***::** ***:*::*

IL2RB_HUMAN   120   HRCNISWEISQASHYFERHLEFEARTLSPGHTWEEAPLLTLKQEWICLETLTPDTQYE   179
IL2RB_MOUSE   121   QRCNISWKVSQVSHYIEPYLEFEARRRLLGHSWEDASVLSLKRQQWLFLEMLIPSTSYE   180
                    :******::**.***:* :****** * .*:**:*.:*:**:*:*: ** *  .: **

IL2RB_HUMAN   180   FQVRVKPLQGEFTTWSPWSQPLAFRTKPAALGKDT----TPWLGHLLVGLSGAFGFIILVYL   237
IL2RB_MOUSE   181   VQVRVKAQRNNTGTWSPWSQPLTFRTRPADPMKEILPMSWLRYLLLVLGCFSGFSCVYI   240
                    .*****   .:  ******:***:*  .*.  :.     :*  ::.** .:.** :**:

IL2_MOUSE       1   APTSSSTSSSTAEAQQQQQQQQQQHLEQLLMDLQELLSRMENYRNLKLPRMLTFKFYL    60
IL2_HUMAN       1   APTSS------------STKKTQLQLEHLLLDLQMILNGINNYKNPKLTRMLTFKFYM    46
                    *****            * :.***  ..**:*:**:** :* :****:*.**:******:

IL2_MOUSE      61   PKQATELKDLQCLEDELGPLRHVLDLTQSKSFQLEDAENFISNIRVTVVKLKGSDNTFEC   120
IL2_HUMAN      47   PKKATELKHLQCLEEELKPLEEVLNLAQSKNFHLRP--RDLISNINVTVLELKGSETTFMC   105
                    **:*****.*****:**.**:.**:*:*** *::     *:**** ***:  ****:.**:*

IL2_MOUSE     121   QEDDESATVVDFLRRWIAFCQSIISTSPQ     149
IL2_HUMAN     106   EYADETATIVEFLNRWITFCQSIISTLT-     133
                    : .**:*:*:* ***:***:******* 
```

FIG. 16D

| | 15 | 16 | 19 | 20 | 23 |
|---|---|---|---|---|---|
| WT | E | H | L | D | M |
| C1 | H | Q | S | I | E |
| C2 | T | Q | V | T | I |
| C3 | T | Q | I | T | I |
| C4 | T | Q | I | T | T |
| C5 | D | N | I | M | F |
| C6 | S | Q | V | L | Q |
| C7 | K | Q | I | T | V |
| C8 | I | Q | I | S | T |
| C9 | K | Q | V | M | L |
| C10 | K | Q | V | T | L |
| C11 | V | Q | V | S | L |
| C12 |   | N | V | M | A |
| C13 | K | Q | I | M | Q |
| C14 | S | Q | V | L | V |

FIG. 16C

| | 15 | 16 | 19 | 20 | 22 | 23 |
|---|---|---|---|---|---|---|
| WT | E | H | L | D | Q | M |
| C1 | S | Q | V | T | K | L |
| C2 | S | Q | V | S | K | L |
| C3 | S | Q | V | S | K | L |
| C4 | S | Q | I | M | K | L |
| C5 | T |   | V | S |   | S |
| C6 | Q | Q | V | M | K | S |
| C7 | Q | Q | V | T | K | S |
| C8 | H | Q | V | S | K | V |
| C9 | H | Q | I | L | K | L |
| C10 |   |   | I | M | N | S |
| C11 |   | Q | V | M | K |   |

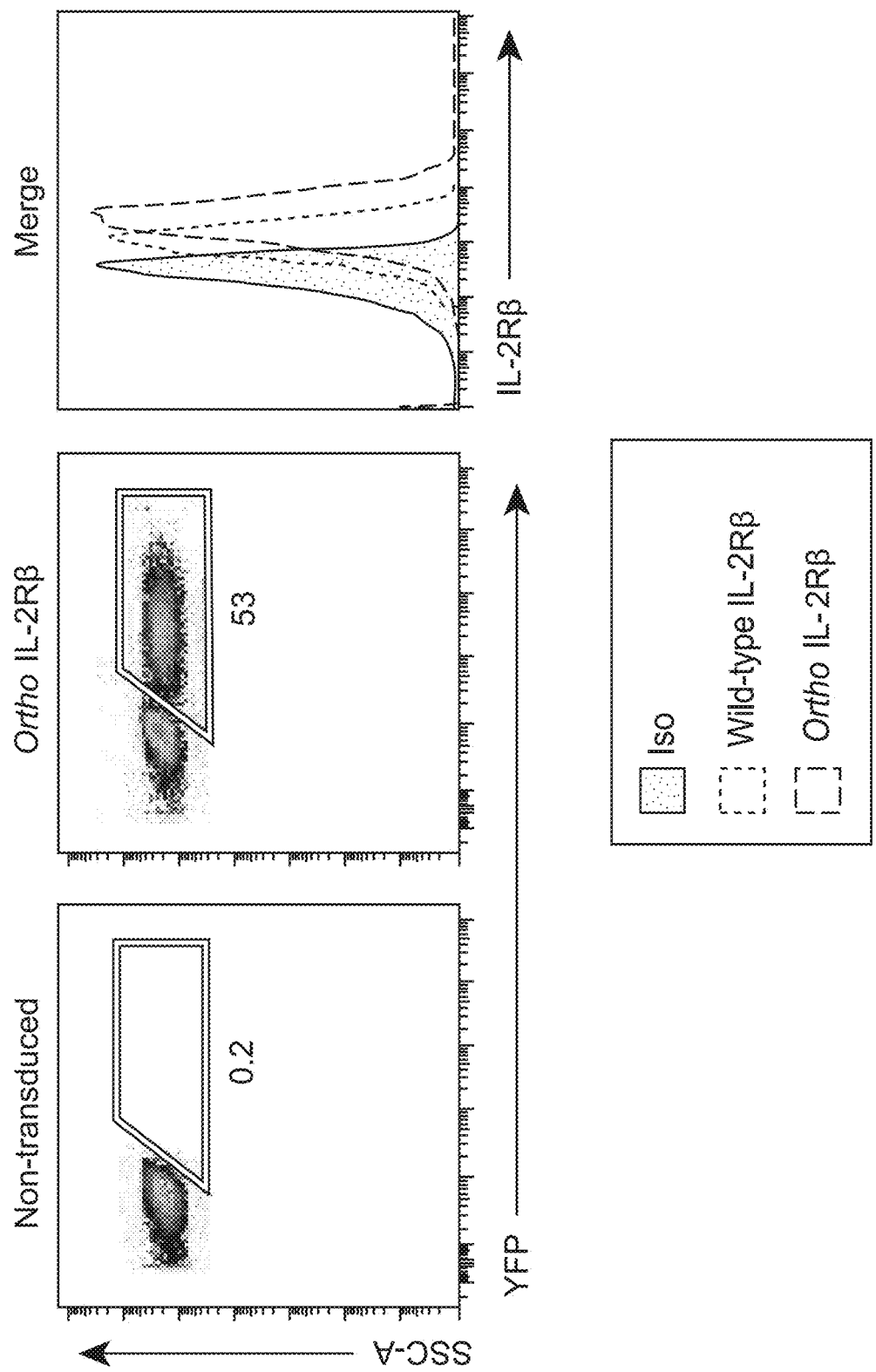

FIG. 21A
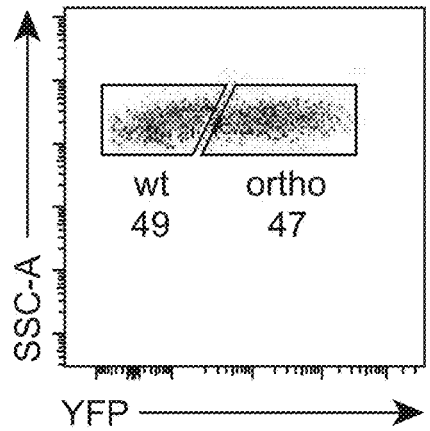
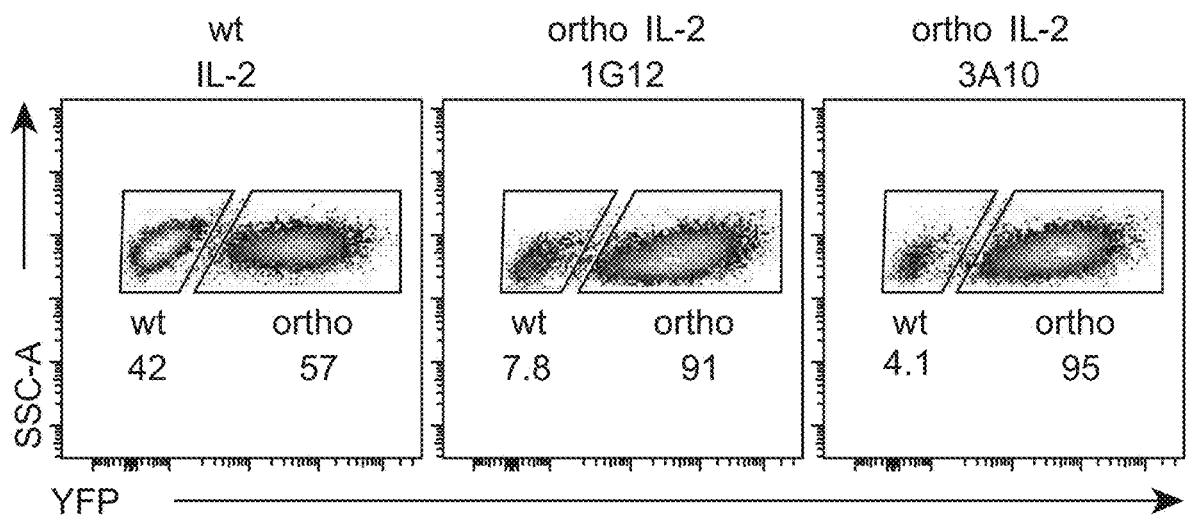

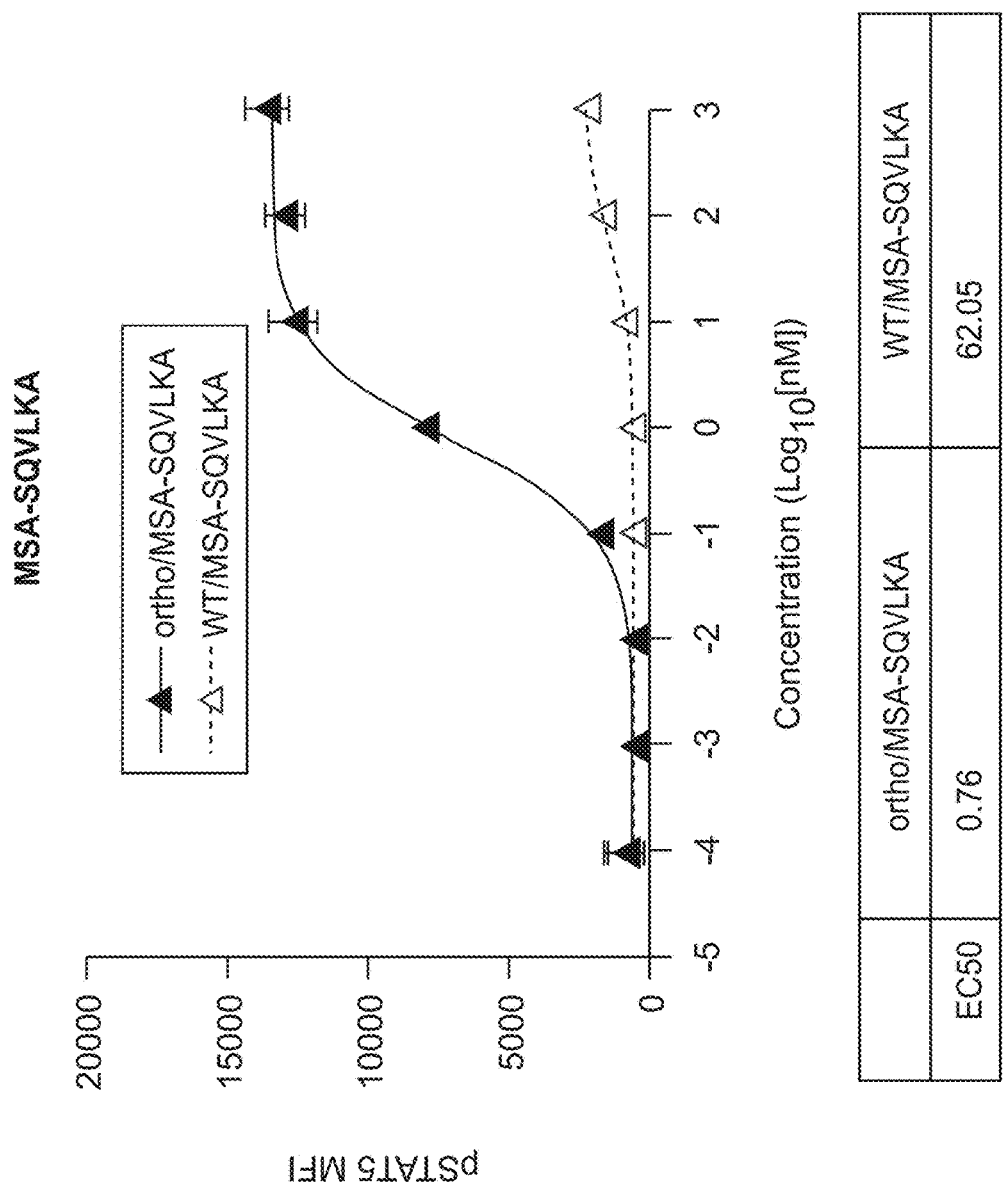

SEQUENCE LISTING

```
<160> NUMBER OF SEQ ID NOS: 26

<210> SEQ ID NO 1
<211> LENGTH: 525
<212> TYPE: PRT
<213> ORGANISM: Homo sapiens

<400> SEQUENCE: 1

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
            85                  90                  95

Asp Phe Lys Pro Phe Glu Asn Leu Arg Leu Met Ala Pro Ile Ser Leu
        100                 105                 110

Gln Val Val His Val Glu Thr His Arg Cys Asn Ile Ser Trp Glu Ile
    115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
            165                 170                 175

Gln Tyr Glu Phe Gln Val Arg Val Lys Pro Leu Gln Gly Glu Phe Thr
        180                 185                 190

Thr Trp Ser Pro Trp Ser Gln Pro Leu Ala Phe Arg Thr Lys Pro Ala
    195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
```

```
                    245                 250                 255
Pro Asp Pro Ser Lys Phe Phe Ser Gln Leu Ser Ser Glu His Gly Gly
                260                 265                 270

Asp Val Gln Lys Trp Leu Ser Ser Pro Phe Pro Ser Ser Ser Phe Ser
            275                 280                 285

Pro Gly Gly Leu Ala Pro Glu Ile Ser Pro Leu Glu Val Leu Glu Arg
        290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525

<210> SEQ ID NO 2
<211> LENGTH: 513
<212> TYPE: PRT
<213> ORGANISM: Mus musculus

<400> SEQUENCE: 2

Ala Val Lys Asn Cys Ser His Leu Glu Cys Phe Tyr Asn Ser Arg Ala
1               5                   10                  15

Asn Val Ser Cys Met Trp Ser His Glu Glu Ala Leu Asn Val Thr Thr
            20                  25                  30

Cys His Val His Ala Lys Ser Asn Leu Arg His Trp Asn Lys Thr Cys
        35                  40                  45

Glu Leu Thr Leu Val Arg Gln Ala Ser Trp Ala Cys Asn Leu Ile Leu
    50                  55                  60

Gly Ser Phe Pro Glu Ser Gln Ser Leu Thr Ser Val Asp Leu Leu Asp
65                  70                  75                  80

Ile Asn Val Val Cys Trp Glu Glu Lys Gly Trp Arg Arg Val Lys Thr
                85                  90                  95
```

```
Cys Asp Phe His Pro Phe Asp Asn Leu Arg Leu Val Ala Pro His Ser
                100                 105                 110

Leu Gln Val Leu His Ile Asp Thr Gln Arg Cys Asn Ile Ser Trp Lys
            115                 120                 125

Val Ser Gln Val Ser His Tyr Ile Glu Pro Tyr Leu Glu Phe Glu Ala
        130                 135                 140

Arg Arg Arg Leu Leu Gly His Ser Trp Glu Asp Ala Ser Val Leu Ser
145                 150                 155                 160

Leu Lys Gln Arg Gln Gln Trp Leu Phe Leu Glu Met Leu Ile Pro Ser
                165                 170                 175

Thr Ser Tyr Glu Val Gln Val Arg Val Lys Ala Gln Arg Asn Asn Thr
            180                 185                 190

Gly Thr Trp Ser Pro Trp Ser Gln Pro Leu Thr Phe Arg Thr Arg Pro
        195                 200                 205

Ala Asp Pro Met Lys Glu Ile Leu Pro Met Ser Trp Leu Arg Tyr Leu
210                 215                 220

Leu Leu Val Leu Gly Cys Phe Ser Gly Phe Phe Ser Cys Val Tyr Ile
225                 230                 235                 240

Leu Val Lys Cys Arg Tyr Leu Gly Pro Trp Leu Lys Thr Val Leu Lys
                245                 250                 255

Cys His Ile Pro Asp Pro Ser Glu Phe Phe Ser Gln Leu Ser Ser Gln
            260                 265                 270

His Gly Gly Asp Leu Gln Lys Trp Leu Ser Ser Pro Val Pro Leu Ser
        275                 280                 285

Phe Phe Ser Pro Ser Gly Pro Ala Pro Glu Ile Ser Pro Leu Glu Val
        290                 295                 300

Leu Asp Gly Asp Ser Lys Ala Val Gln Leu Leu Leu Leu Gln Lys Asp
305                 310                 315                 320

Ser Ala Pro Leu Pro Ser Pro Ser Gly His Ser Gln Ala Ser Cys Phe
                325                 330                 335

Thr Asn Gln Gly Tyr Phe Phe Phe His Leu Pro Asn Ala Leu Glu Ile
            340                 345                 350

Glu Ser Cys Gln Val Tyr Phe Thr Tyr Asp Pro Cys Val Glu Glu Glu
        355                 360                 365

Val Glu Glu Asp Gly Ser Arg Leu Pro Glu Gly Ser Pro His Pro Pro
370                 375                 380

Leu Leu Pro Leu Ala Gly Glu Gln Asp Asp Tyr Cys Ala Phe Pro Pro
385                 390                 395                 400

Arg Asp Asp Leu Leu Leu Phe Ser Pro Ser Leu Ser Thr Pro Asn Thr
                405                 410                 415

Ala Tyr Gly Gly Ser Arg Ala Pro Glu Glu Arg Ser Pro Leu Ser Leu
            420                 425                 430

His Glu Gly Leu Pro Ser Leu Ala Ser Arg Asp Leu Met Gly Leu Gln
        435                 440                 445

Arg Pro Leu Glu Arg Met Pro Glu Gly Asp Gly Glu Gly Leu Ser Ala
        450                 455                 460

Asn Ser Ser Gly Glu Gln Ala Ser Val Pro Glu Gly Asn Leu His Gly
465                 470                 475                 480

Gln Asp Gln Asp Arg Gly Gln Gly Pro Ile Leu Thr Leu Asn Thr Asp
                485                 490                 495

Ala Tyr Leu Ser Leu Gln Glu Leu Gln Ala Gln Asp Ser Val His Leu
            500                 505                 510

Ile
```

<210> SEQ ID NO 3
<211> LENGTH: 149
<212> TYPE: PRT
<213> ORGANISM: Mus musculus

<400> SEQUENCE: 3

Ala Pro Thr Ser Ser Thr Ser Ser Ser Thr Ala Glu Ala Gln Gln
1               5                   10                  15

Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
        50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 4
<211> LENGTH: 133
<212> TYPE: PRT
<213> ORGANISM: Homo sapiens

<400> SEQUENCE: 4

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 5
<211> LENGTH: 133
<212> TYPE: PRT
<213> ORGANISM: Artificial sequence
<220> FEATURE:
<223> OTHER INFORMATION: synthetic polypeptide

<400> SEQUENCE: 5

```
Ala Pro Thr Ser Ser Ser Thr Lys Lys Thr Gln Leu Gln Leu Ser Gln
1               5                   10                  15
Leu Leu Val Leu Leu Gln Gln Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Ile Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Asp Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 6
<211> LENGTH: 133
<212> TYPE: PRT
<213> ORGANISM: Artificial sequence
<220> FEATURE:
<223> OTHER INFORMATION: synthetic polypeptide

<400> SEQUENCE: 6

```
Ala Pro Thr Ser Ser Ser Thr Lys Lys Thr Gln Leu Gln Leu Ser Gln
1               5                   10                  15
Leu Leu Val Leu Leu Gln Gln Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Tyr Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 7
<211> LENGTH: 133
<212> TYPE: PRT
<213> ORGANISM: Artificial sequence
<220> FEATURE:
<223> OTHER INFORMATION: synthetic polypeptide

<400> SEQUENCE: 7

Ala Pro Thr Ser Ser Ser Thr Lys Lys Thr Gln Leu Gln Leu Ser Gln
1               5                   10                  15

Leu Leu Val Leu Leu Lys Ala Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
                115                 120                 125

Ile Ser Thr Leu Thr
        130

<210> SEQ ID NO 8
<211> LENGTH: 133
<212> TYPE: PRT
<213> ORGANISM: Artificial sequence
<220> FEATURE:
<223> OTHER INFORMATION: synthetic polypeptide

<400> SEQUENCE: 8

Ala Pro Thr Ser Ser Ser Thr Lys Lys Thr Gln Leu Gln Leu Ser Gln
1               5                   10                  15

Leu Leu Val Leu Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
                115                 120                 125

Ile Ser Thr Leu Thr
        130

<210> SEQ ID NO 9
<211> LENGTH: 525
<212> TYPE: PRT
<213> ORGANISM: Homo sapiens

<400> SEQUENCE: 9

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys

```
            35                  40                  45
Glu Leu Leu Pro Val Ser Gln Ala Ser Trp Ala Cys Asn Leu Ile Leu
 50                  55                  60
Gly Ala Pro Asp Ser Gln Lys Leu Thr Thr Val Asp Ile Val Thr Leu
 65                  70                  75                  80
Arg Val Leu Cys Arg Glu Gly Val Arg Trp Arg Val Met Ala Ile Gln
                 85                  90                  95
Asp Phe Lys Pro Phe Glu Asn Leu Arg Leu Met Ala Pro Ile Ser Leu
                100                 105                 110
Gln Val Val His Val Glu Thr His Arg Cys Asn Ile Ser Trp Glu Ile
                115                 120                 125
Ser Gln Ala Ser Asp Phe Phe Glu Arg His Leu Glu Phe Glu Ala Arg
                130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
                180                 185                 190
Thr Trp Ser Pro Trp Ser Gln Pro Leu Ala Phe Arg Thr Lys Pro Ala
                195                 200                 205
Ala Leu Gly Lys Asp Thr Ile Pro Trp Leu Gly His Leu Leu Val Gly
                210                 215                 220
Leu Ser Gly Ala Phe Gly Phe Ile Ile Leu Val Tyr Leu Leu Ile Asn
225                 230                 235                 240
Cys Arg Asn Thr Gly Pro Trp Leu Lys Lys Val Leu Lys Cys Asn Thr
                245                 250                 255
Pro Asp Pro Ser Lys Phe Phe Ser Gln Leu Ser Ser Glu His Gly Gly
                260                 265                 270
Asp Val Gln Lys Trp Leu Ser Ser Pro Phe Pro Ser Ser Ser Phe Ser
                275                 280                 285
Pro Gly Gly Leu Ala Pro Glu Ile Ser Pro Leu Glu Val Leu Glu Arg
                290                 295                 300
Asp Lys Val Thr Gln Leu Leu Leu Gln Gln Asp Lys Val Pro Glu Pro
305                 310                 315                 320
Ala Ser Leu Ser Ser Asn His Ser Leu Thr Ser Cys Phe Thr Asn Gln
                325                 330                 335
Gly Tyr Phe Phe Phe His Leu Pro Asp Ala Leu Glu Ile Glu Ala Cys
                340                 345                 350
Gln Val Tyr Phe Thr Tyr Asp Pro Tyr Ser Glu Glu Asp Pro Asp Glu
                355                 360                 365
Gly Val Ala Gly Ala Pro Thr Gly Ser Ser Pro Gln Pro Leu Gln Pro
                370                 375                 380
Leu Ser Gly Glu Asp Asp Ala Tyr Cys Thr Phe Pro Ser Arg Asp Asp
385                 390                 395                 400
Leu Leu Leu Phe Ser Pro Ser Leu Leu Gly Gly Pro Ser Pro Pro Ser
                405                 410                 415
Thr Ala Pro Gly Gly Ser Gly Ala Gly Glu Glu Arg Met Pro Pro Ser
                420                 425                 430
Leu Gln Glu Arg Val Pro Arg Asp Trp Asp Pro Gln Pro Leu Gly Pro
                435                 440                 445
Pro Thr Pro Gly Val Pro Asp Leu Val Asp Phe Gln Pro Pro Pro Glu
                450                 455                 460
```

```
Leu Val Leu Arg Glu Ala Gly Glu Val Pro Asp Ala Gly Pro Arg
465                 470                 475                 480

Glu Gly Val Ser Phe Pro Trp Ser Arg Pro Gly Gln Gly Glu Phe
            485                 490                 495

Arg Ala Leu Asn Ala Arg Leu Pro Leu Asn Thr Asp Ala Tyr Leu Ser
        500                 505                 510

Leu Gln Glu Leu Gln Gly Gln Asp Pro Thr His Leu Val
    515                 520                 525

<210> SEQ ID NO 10
<211> LENGTH: 98
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (33)..(33)
<223> OTHER INFORMATION: N at position 33 may be a, c, g, or t
<220> FEATURE:
<221> NAME/KEY: misc_feature
<222> LOCATION: (34)..(34)
<223> OTHER INFORMATION: N at position 34 may be a, c, or t
<220> FEATURE:
<221> NAME/KEY: misc_feature
<222> LOCATION: (35)..(35)
<223> OTHER INFORMATION: N at position 35 may be g or t
<220> FEATURE:
<221> NAME/KEY: misc_feature
<222> LOCATION: (36)..(36)
<223> OTHER INFORMATION: N at position 36 may a, c, g, or t
<220> FEATURE:
<221> NAME/KEY: misc_feature
<222> LOCATION: (37)..(37)
<223> OTHER INFORMATION: N at position 37 may be a, c, or t
<220> FEATURE:
<221> NAME/KEY: misc_feature
<222> LOCATION: (38)..(38)
<223> OTHER INFORMATION: N at position 38 may be g or t
<220> FEATURE:
<221> NAME/KEY: misc_feature
<222> LOCATION: (45)..(45)
<223> OTHER INFORMATION: N at position 45 may be a, c, g, or t
<220> FEATURE:
<221> NAME/KEY: misc_feature
<222> LOCATION: (46)..(46)
<223> OTHER INFORMATION: N at position 46 may be a, c, or t
<220> FEATURE:
<221> NAME/KEY: misc_feature
<222> LOCATION: (47)..(47)
<223> OTHER INFORMATION: N at position 47 may be g or t
<220> FEATURE:
<221> NAME/KEY: misc_feature
<222> LOCATION: (48)..(48)
<223> OTHER INFORMATION: N at position 48 may be a, c, or t
<220> FEATURE:
<221> NAME/KEY: misc_feature
<222> LOCATION: (49)..(49)
<223> OTHER INFORMATION: N at position 49 may be a, c, or t
<220> FEATURE:
<221> NAME/KEY: misc_feature
<222> LOCATION: (50)..(50)
<223> OTHER INFORMATION: N at position 50 may be g or t
<220> FEATURE:
<221> NAME/KEY: misc_feature
<222> LOCATION: (54)..(54)
<223> OTHER INFORMATION: N at position 54 may be a, c, g, or t
<220> FEATURE:
<221> NAME/KEY: misc_feature
<222> LOCATION: (55)..(55)
<223> OTHER INFORMATION: N at position 55 may be a, c, or t
<220> FEATURE:
<221> NAME/KEY: misc_feature
<222> LOCATION: (56)..(56)
```

<223> OTHER INFORMATION: N at position 56 may be g or t
<220> FEATURE:
<221> NAME/KEY: misc_feature
<222> LOCATION: (57)..(59)
<223> OTHER INFORMATION: n is a, c, g, or t

<400> SEQUENCE: 10
caagttctac aaagaaaaca cagctacaac tgnnnnnntt acttnnnnnn ttannnnnna    60
ttttgaatgg aattaataat tacaagaatc ccaaactc                           98

<210> SEQ ID NO 11
<211> LENGTH: 88
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (30)..(30)
<223> OTHER INFORMATION: N at position 30 is a, c, g, or t
<220> FEATURE:
<221> NAME/KEY: misc_feature
<222> LOCATION: (31)..(31)
<223> OTHER INFORMATION: N at position 31 is a, c, or t
<220> FEATURE:
<221> NAME/KEY: misc_feature
<222> LOCATION: (32)..(32)
<223> OTHER INFORMATION: N at position 32 is g or t
<220> FEATURE:
<221> NAME/KEY: misc_feature
<222> LOCATION: (33)..(33)
<223> OTHER INFORMATION: N at position 33 is a, c, g, or t
<220> FEATURE:
<221> NAME/KEY: misc_feature
<222> LOCATION: (34)..(34)
<223> OTHER INFORMATION: N at position 34 is a, c, or t
<220> FEATURE:
<221> NAME/KEY: misc_feature
<222> LOCATION: (35)..(35)
<223> OTHER INFORMATION: N at position 35 is g or t
<220> FEATURE:
<221> NAME/KEY: misc_feature
<222> LOCATION: (42)..(42)
<223> OTHER INFORMATION: N at position 42 is a, c, g, or t
<220> FEATURE:
<221> NAME/KEY: misc_feature
<222> LOCATION: (43)..(43)
<223> OTHER INFORMATION: N at position 43 is a, c, or t
<220> FEATURE:
<221> NAME/KEY: misc_feature
<222> LOCATION: (44)..(44)
<223> OTHER INFORMATION: N at position 44 g or t
<220> FEATURE:
<221> NAME/KEY: misc_feature
<222> LOCATION: (45)..(45)
<223> OTHER INFORMATION: N at position 45 is a, c, g, or t
<220> FEATURE:
<221> NAME/KEY: misc_feature
<222> LOCATION: (46)..(46)
<223> OTHER INFORMATION: N at position 46 is a, c, or t
<220> FEATURE:
<221> NAME/KEY: misc_feature
<222> LOCATION: (47)..(47)
<223> OTHER INFORMATION: N at position 47 is g or t
<220> FEATURE:
<221> NAME/KEY: misc_feature
<222> LOCATION: (54)..(54)
<223> OTHER INFORMATION: N at position 54 is a, c, g, or t
<220> FEATURE:
<221> NAME/KEY: misc_feature
<222> LOCATION: (55)..(55)
<223> OTHER INFORMATION: N at position 55 a, c, or t
<220> FEATURE:
<221> NAME/KEY: misc_feature
<222> LOCATION: (56)..(56)
<223> OTHER INFORMATION: N at position 56 is g or t

<400> SEQUENCE: 11
gttctacaaa gaaaacacag ctacaactgn nnnnnttact tnnnnnntta cagnnnattt          60
tgaatggaat taataattac aagaatcc          88

<210> SEQ ID NO 12
<211> LENGTH: 50
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (19)..(19)
<223> OTHER INFORMATION: N at position 19 is a, c, g, or t
<220> FEATURE:
<221> NAME/KEY: misc_feature
<222> LOCATION: (20)..(20)
<223> OTHER INFORMATION: N at position 20 is a, c, or t
<220> FEATURE:
<221> NAME/KEY: misc_feature
<222> LOCATION: (21)..(21)
<223> OTHER INFORMATION: N at position 21 is g or t

<400> SEQUENCE: 12
cccagggact taatcagcnn natcaacgta atagttctgg aactaaaggg          50

<210> SEQ ID NO 13
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 13
cggtagcggt gggggcggtt ctctggaagt tctgttccag ggtccgagcg gcgga          55

<210> SEQ ID NO 14
<211> LENGTH: 59
<212> TYPE: DNA
<213> ORGANISM: Artificial sequence
<220> FEATURE:
<223> OTHER INFORMATION: synthetic polynucleotide

<400> SEQUENCE: 14
gtagctgtgt tttctttgta gaacttgaag taggtgcgga tccgccgctc ggaccctgg          59

<210> SEQ ID NO 15
<211> LENGTH: 60
<212> TYPE: DNA
<213> ORGANISM: Artificial sequence
<220> FEATURE:
<223> OTHER INFORMATION: synthetic polynucleotide

<400> SEQUENCE: 15
cttaaatgtg agcatcctgg tgagtttggg attcttgtaa ttattaattc cattcaaaat          60

<210> SEQ ID NO 16
<211> LENGTH: 45
<212> TYPE: DNA
<213> ORGANISM: Artificial sequence
<220> FEATURE:
<223> OTHER INFORMATION: synthetic polynucleotide

<400> SEQUENCE: 16
ccaggatgct cacatttaag ttttacatgc ccaagaaggc cacag          45

<210> SEQ ID NO 17
<211> LENGTH: 59
<212> TYPE: DNA
<213> ORGANISM: Artificial sequence
<220> FEATURE:
<223> OTHER INFORMATION: synthetic polynucleotide

<400> SEQUENCE: 17
gaggtttgag ttcttcttct agacactgaa gatgtttcag ttctgtggcc ttcttgggc      59

<210> SEQ ID NO 18
<211> LENGTH: 57
<212> TYPE: DNA
<213> ORGANISM: Artificial sequence
<220> FEATURE:
<223> OTHER INFORMATION: synthetic polynucleotide

<400> SEQUENCE: 18
cagtgtctag aagaagaact caaacctctg gaggaagtgc taaatttagc tcaaagc        57

<210> SEQ ID NO 19
<211> LENGTH: 60
<212> TYPE: DNA
<213> ORGANISM: Artificial sequence
<220> FEATURE:
<223> OTHER INFORMATION: synthetic polynucleotide

<400> SEQUENCE: 19
gattaagtcc ctgggtctta agtgaaagtt tttgctttga gctaaattta gcacttcctc    60

<210> SEQ ID NO 20
<211> LENGTH: 59
<212> TYPE: DNA
<213> ORGANISM: Artificial sequence
<220> FEATURE:
<223> OTHER INFORMATION: synthetic polynucleotide

<400> SEQUENCE: 20
cagcatattc acacatgaat gttgtttcag atcccttag ttccagaact attacgttg       59

<210> SEQ ID NO 21
<211> LENGTH: 60
<212> TYPE: DNA
<213> ORGANISM: Artificial sequence
<220> FEATURE:
<223> OTHER INFORMATION: synthetic polynucleotide

<400> SEQUENCE: 21
gaaacaacat tcatgtgtga atatgctgat gagacagcaa ccattgtaga atttctgaac    60

<210> SEQ ID NO 22
<211> LENGTH: 58
<212> TYPE: DNA
<213> ORGANISM: Artificial sequence
<220> FEATURE:
<223> OTHER INFORMATION: synthetic polynucleotide

<400> SEQUENCE: 22
gagatgatgc tttgacaaaa ggtaatccat ctgttcagaa attctacaat ggttgctg      58

<210> SEQ ID NO 23
<211> LENGTH: 59
<212> TYPE: DNA
<213> ORGANISM: Artificial sequence
<220> FEATURE:
<223> OTHER INFORMATION: synthetic polynucleotide

```
<400> SEQUENCE: 23
gattaccttt tgtcaaagca tcatctcaac actaactgcg gccgcttctg gtggcgaac        59

<210> SEQ ID NO 24
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 24
gatctcgagc aagtcttctt cggagataag cttttgttcg ccaccagaag cgg              53

<210> SEQ ID NO 25
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 25
cggtagcggt gggggcggtt c                                                 21

<210> SEQ ID NO 26
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 26
cgaagaagac ttgctcgaga tc                                                22
```

BIOLOGICALLY RELEVANT ORTHOGONAL CYTOKINE/RECEPTOR PAIRS

CROSS REFERENCE

This application claims benefit and is a Continuation of U.S. patent application Ser. No. 15/916,689, filed Mar. 9, 2018, which is a Continuation in Part of PCT Application No. PCT/US2016/050511, filed Sep. 7, 2016, which claims benefit of U.S. Provisional Patent Application No. 62/217,364, filed Sep. 11, 2015, and U.S. Provisional Patent Application No. 62/375,089, filed Aug. 15, 2016 which applications are incorporated herein by reference in their entirety.

FEDERALLY SPONSORED RESEARCH AND DEVELOPMENT

This invention was made with Government support under contract AI513210 awarded by the National Institutes of Health. The Government has certain rights in the invention.

BACKGROUND OF THE INVENTION

The manipulation of cells, particularly immune cells, to differentiate, develop specialized functions and expand in numbers is of great clinical interest. Many protein factors that affect these activities are known in the art, including in particular cytokines and chemokines. However, these signaling molecules also have pleiotropic effects on cells not targeted for manipulation, and thus methods of selectively activating signaling in a targeted cell population are desirable. In particular, engineering of T cells to carry out controlled behaviors is of interest. For example, in adoptive immunotherapy T cells are isolated from blood, processed ex vivo, and re-infused into patients. T cells have been engineered for use in therapeutic applications such as the recognition and killing of cancer cells, intracellular pathogens and cells involved in auto-immunity.

A critical challenge in cell based therapies is engineering into adoptively transferred cells a desired behavior, such as activation, expansion, etc., that is protected from endogenous signaling pathways, that does not affect non-targeted endogenous cells, and that can be controlled once administered to a patient. This is particularly relevant for T cell engineering because of developmental plasticity and the immense impact that environmental factors play in determining T cell fate, function, and localization.

The ability to manipulate proteins to bind and respond to modified ligands in a manner independent, or orthogonal, from the influence of the native proteins or ligands, constitutes a significant challenge in protein engineering. To date, numerous synthetic ligand-ortholog receptor pairs have been created that are orthogonal to the analogous natural interaction. Among the proteins used for this work, are included nuclear hormone receptors and G-protein coupled receptors. Despite the extensive work carried out to engineer receptors that are activated by synthetic small molecule ligands, the engineering of pairs of biologically relevant proteins remains a significant challenge.

SUMMARY OF THE INVENTION

Engineered orthogonal cytokine receptor/ligand pairs, and methods of use thereof, are provided. An engineered (orthogonal) cytokine specifically binds to a counterpart engineered (orthogonal) receptor. Upon binding, the orthogonal receptor activates signaling that is transduced through native cellular elements to provide for a biological activity that mimics that native response, but which is specific to an engineered cell expressing the orthogonal receptor. The orthogonal receptor does not bind to the endogenous counterpart cytokine, including the native counterpart of the orthogonal cytokine, while the orthogonal cytokine does not bind to any endogenous receptors, including the native counterpart of the orthogonal receptor. In some embodiments, the affinity of the orthogonal cytokine for the orthogonal receptor is comparable to the affinity of the native cytokine for the native receptor.

The process for engineering an orthogonal cytokine receptor pair may comprise the steps of (a) engineering amino acid changes into a native receptor to disrupt binding to the native cytokine; (b) engineering amino acid changes into the native cytokine at contact residues for receptor binding, (c) selecting for cytokine orthologs that bind to the ortholog receptor; (d) discarding ortholog cytokines that bind to the native receptor, or alternatively to steps (c) and (d); (e) selecting for receptor orthologs that bind the ortholog cytokine; (f) discarding ortholog receptors that bind to the native cytokine. In preferred embodiments, knowledge of the structure of the cytokine/receptor complex is used to select amino acid positions for site-directed or error prone mutagenesis. Conveniently a yeast display system can be used for the selection process, although other display and selection methods are also useful.

In some embodiments, an engineered cell is provided, in which the cell has been modified by introduction of an orthologous receptor of the invention. Any cell can be used for this purpose. In some embodiments the cell is a T cell, including without limitation naïve CD8$^+$ T cells, cytotoxic CD8$^+$ T cells, naïve CD4$^+$ T cells, helper T cells, e.g. $T_H1$, $T_H2$, $T_H9$, $T_H11$, $T_H22$, $T_{FH}$; regulatory T cells, e.g. $T_R1$, natural $T_{Reg}$, inducible $T_{Reg}$; memory T cells, e.g. central memory T cells, effector memory T cells, NKT cells, γδ T cells; etc. In other embodiments the engineered cell is a stem cell, e.g. a hematopoietic stem cell, an NK cell, a macrophage, or a dendritic cell. In some embodiments the cell is genetically modified in an ex vivo procedure, prior to transfer into a subject. The engineered cell can be provided in a unit dose for therapy, and can be allogeneic, autologous, etc. with respect to an intended recipient.

In some embodiments a vector comprising a coding sequence that encodes the orthogonal receptor is provided, where the coding sequence is operably linked to a promoter active in the desired cell. Various vectors are known in the art and can be used for this purpose, e.g. viral vectors, plasmid vectors, minicircle vectors, which vectors can be integrated into the target cell genome, or can be episomally maintained. The receptor encoding vector may be provided in a kit, combined with a vector encoding an orthologous cytokine that binds to and activates the receptor. In some embodiments the coding sequence for the orthologous cytokine is operably linked to a high expression promoter, and may be optimized for production. In other embodiments, a kit is provided in which the vector encoding the orthologous receptor is provided with a purified composition of the orthologous cytokine, e.g. in a unit dose, packaged for administration to a patient. In still some other embodiments, a kit is provided in which the vector encoding the orthologous receptor is provided with a vector encoding the orthologous cytokine to enable expression of the orthologous receptor in a cell and also expression of the orthologous cytokine intended for secretion by the same cell to enable autocrine orthogonal cytokine-receptor signaling.

In some embodiments a therapeutic method is provided, the method comprising introducing into a recipient in need thereof of an engineered cell population, wherein the cell population has been modified by introduction of a sequence encoding an orthologous receptor of the invention. The cell population may be engineered ex vivo, and is usually autologous or allogeneic with respect to the recipient. In some embodiments, the introduced cell population is contacted with the cognate orthologous cytokine in vivo, following administration of the engineered cells. An advantage of the present invention is a lack of cross-reactivity between the orthologous cytokine and the native receptor.

Figure 1B:
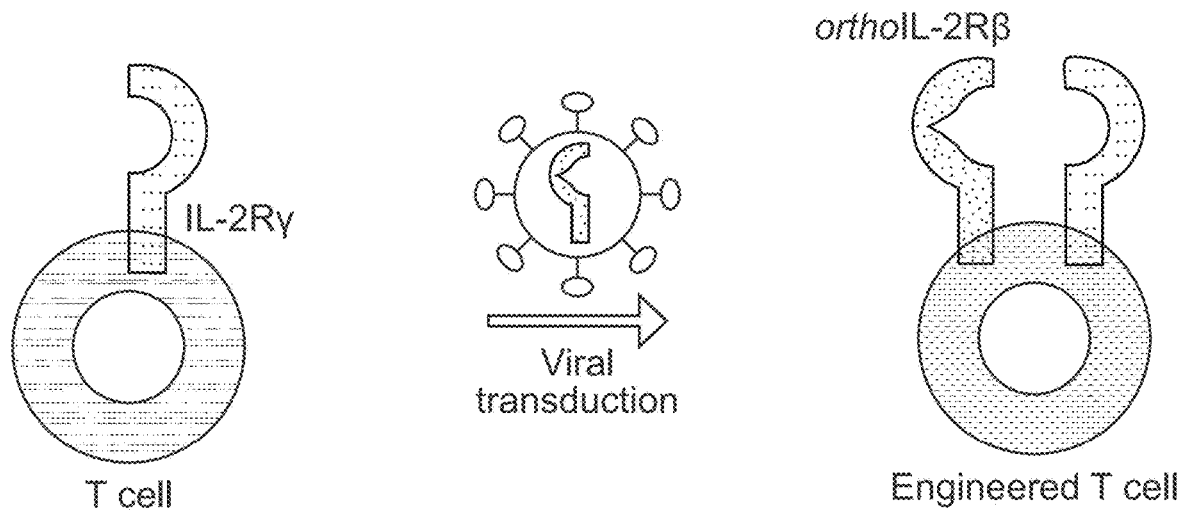
Figure 1C:
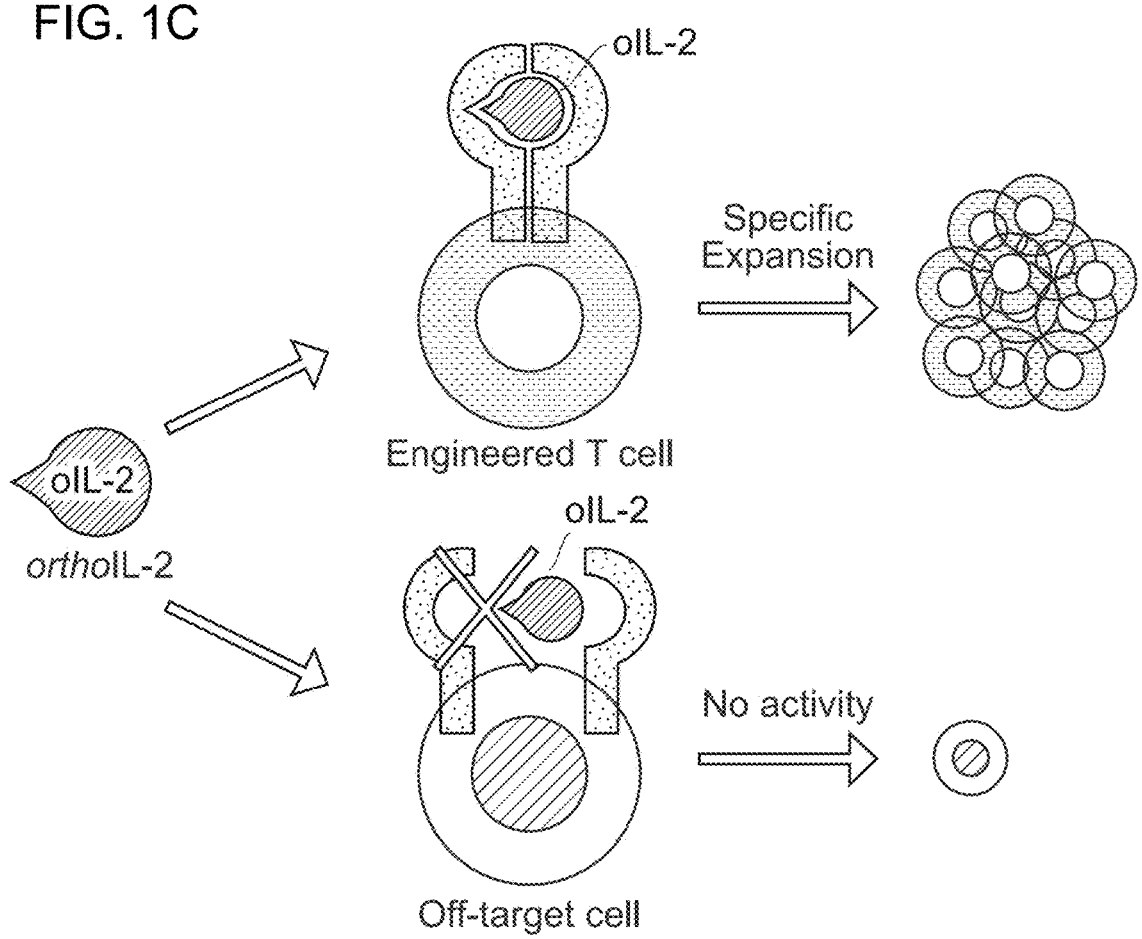

BRIEF DESCRIPTION OF THE DRAWINGS 1A-1C. FIG. 1A. Orthogonal IL-2/1L-2 receptor pairs to control T cell expansion. FIGS. 1B-1C. Application: adoptive T cell therapy.

Figure 2A:
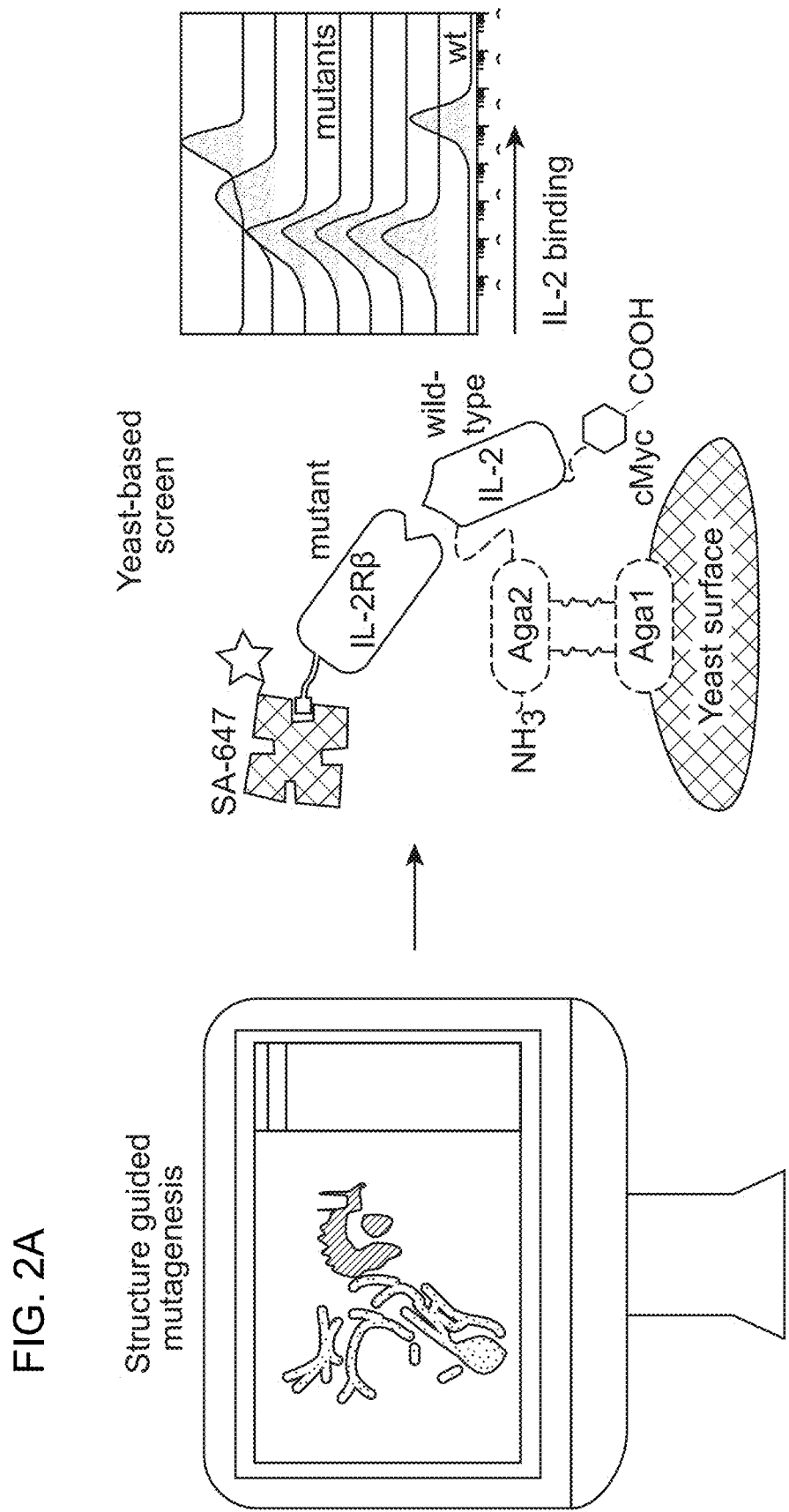
Figure 2B:
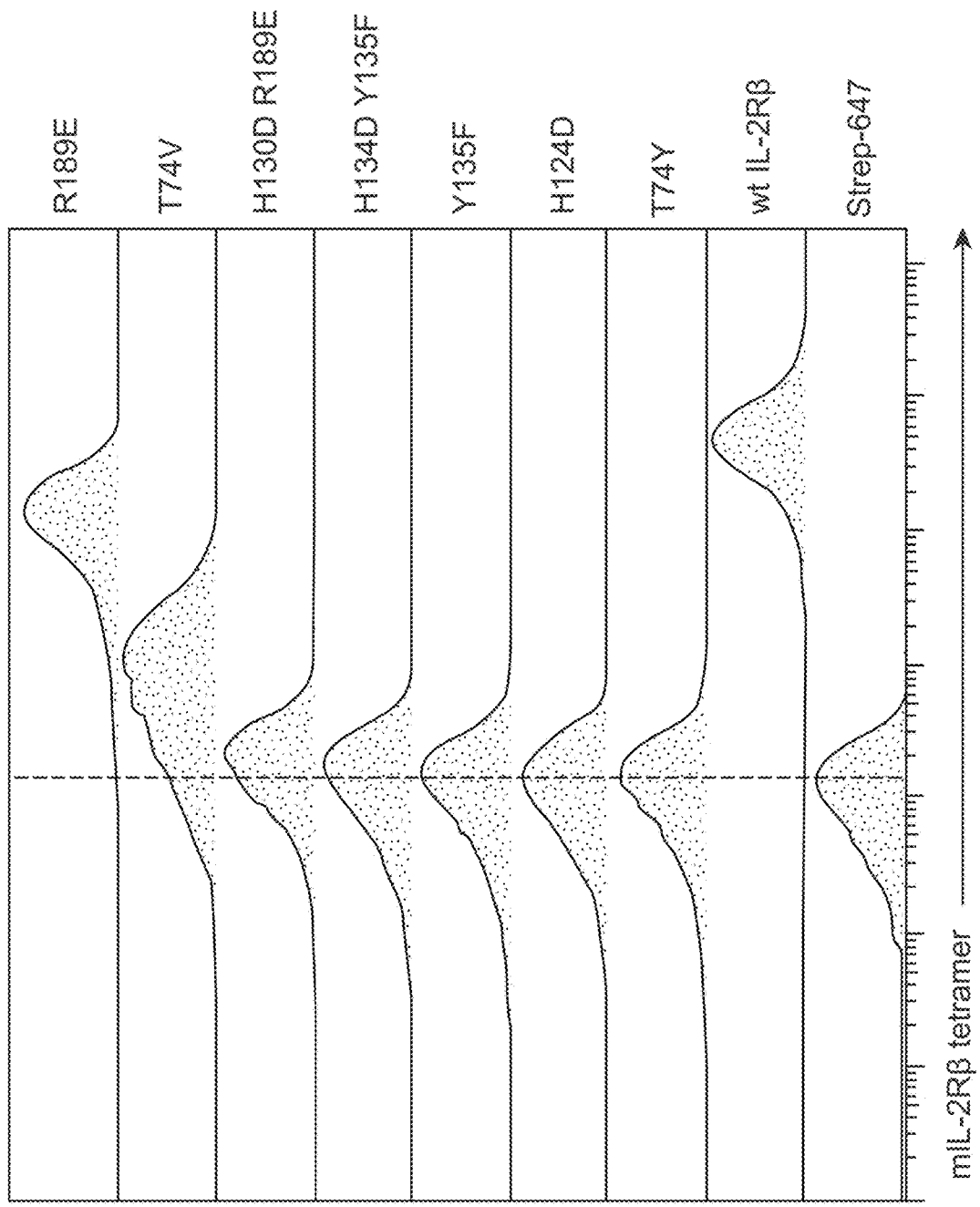

FIG. 2A-FIG. 2B: FIG. 2A Work flow for engineering orthogonal 1L-2/1L-2Rβ pairs. FIG. 2B. Graph of tetramer binding.

FIG. 3. Sequences of orthogonal mouse 1L-2Rβ variants.

Figure 4B:
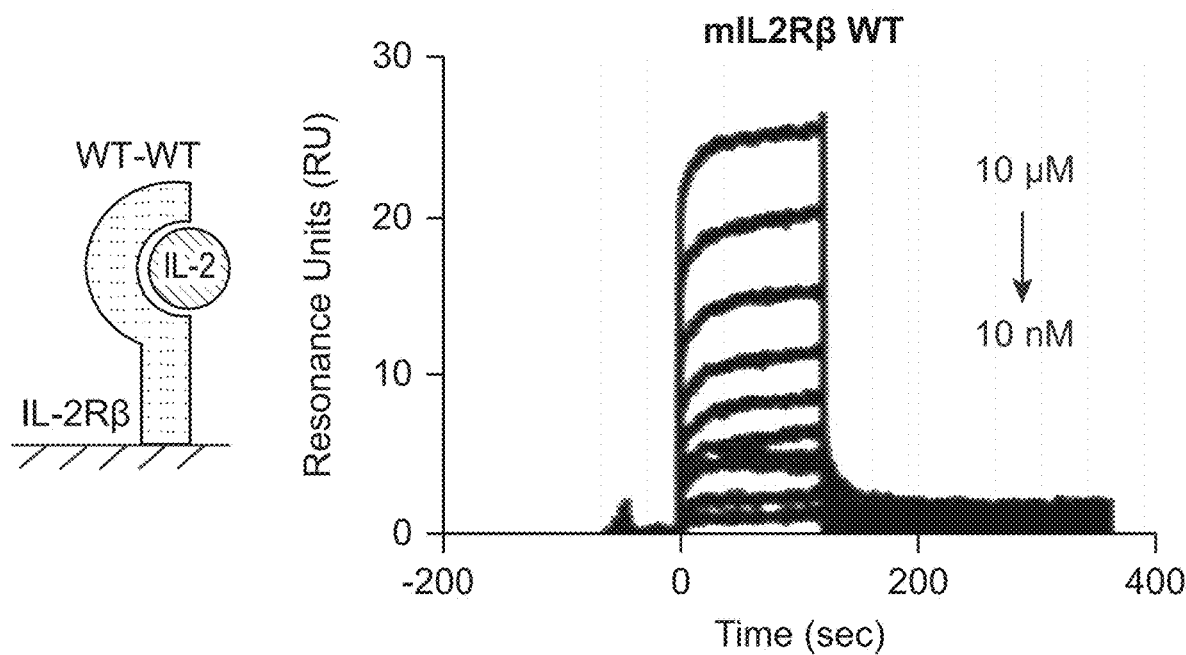
Figure 4C:
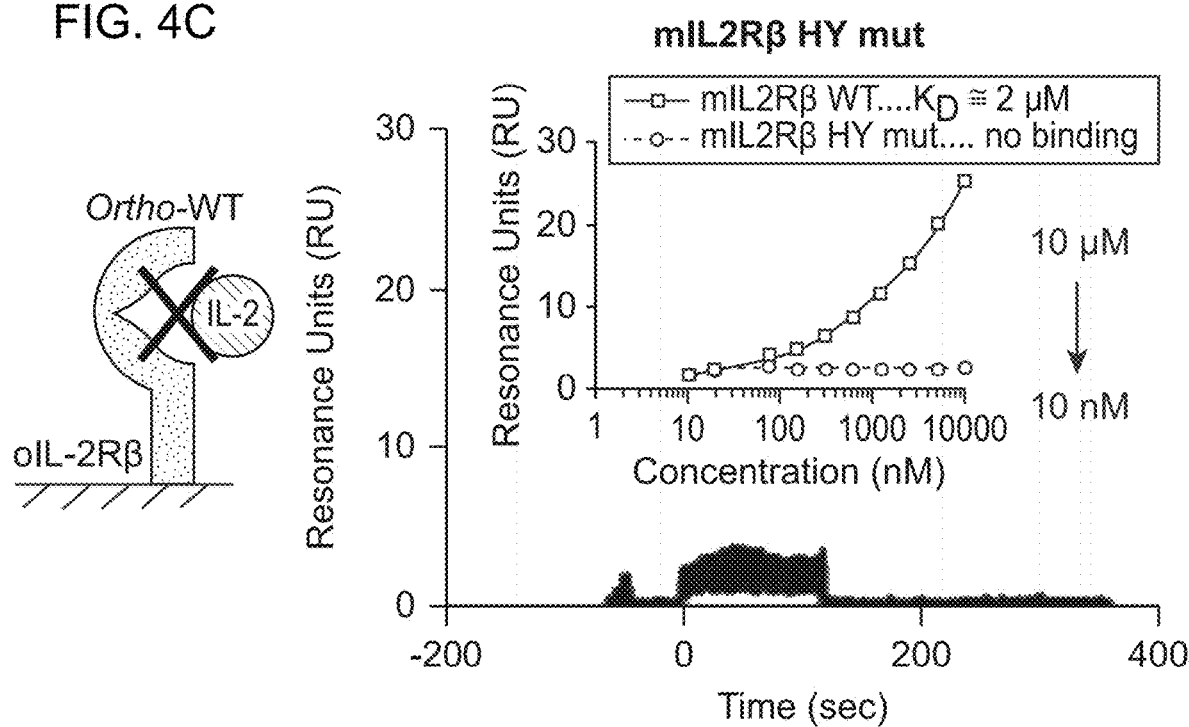

FIG. 4A-FIG. 4C. mIL-2Rβ H134D Y135F mutations abrogate wt mIL-2 binding. FIG. 4A. Structure model. FIG. 4B-FIG. 4C. Binding of IL-2 and IL-2β.

Figure 5A:
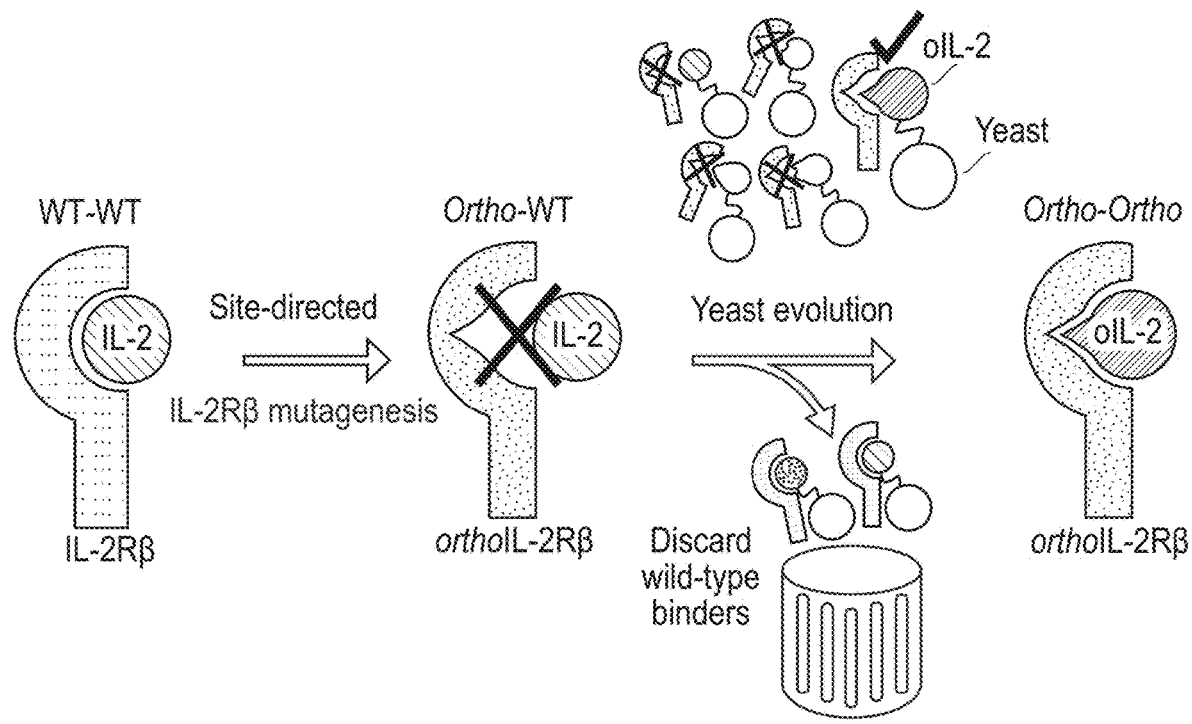
Figure 5B:
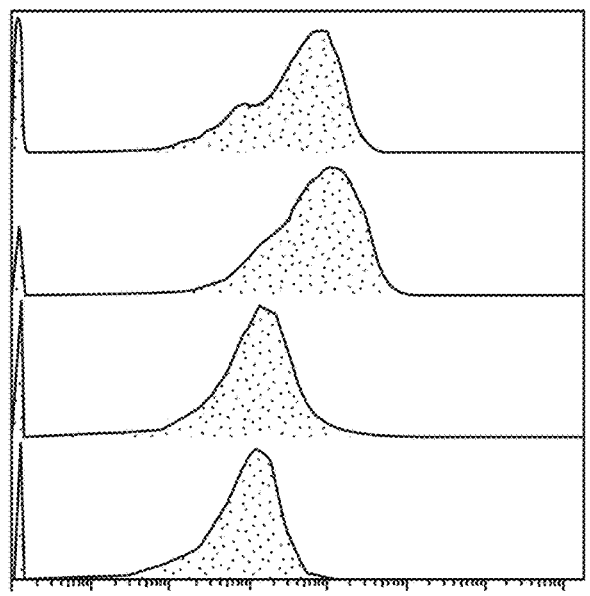

FIG. 5A-FIG. 5B. FIG. 5A. Work flow for engineering orthogonal IL-2/1L-2Rβ pairs. FIG. 5B. Graph of binding.

FIG. 6. Sequences of characterized orthogonal mouse IL-2 variants.

Figure 7A:
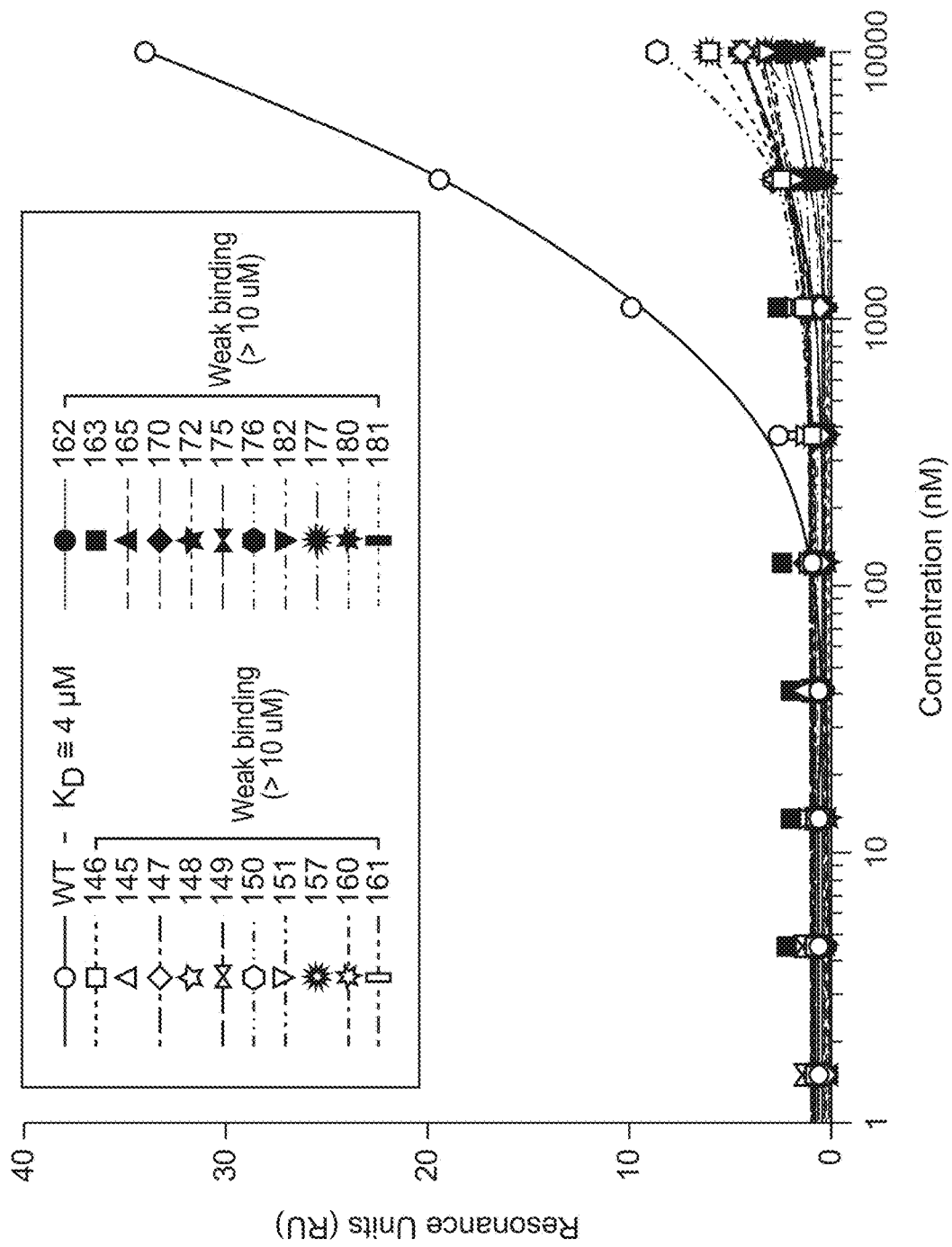

FIG. 7A-FIG. 7B. FIG. 7A-FIG. 7B. OrthoIL-2 variants bind orthoIL-2Rβ with affinity similar to or greater than the wild-type IL-2 and IL-2Rβ interaction.

Figure 8A:
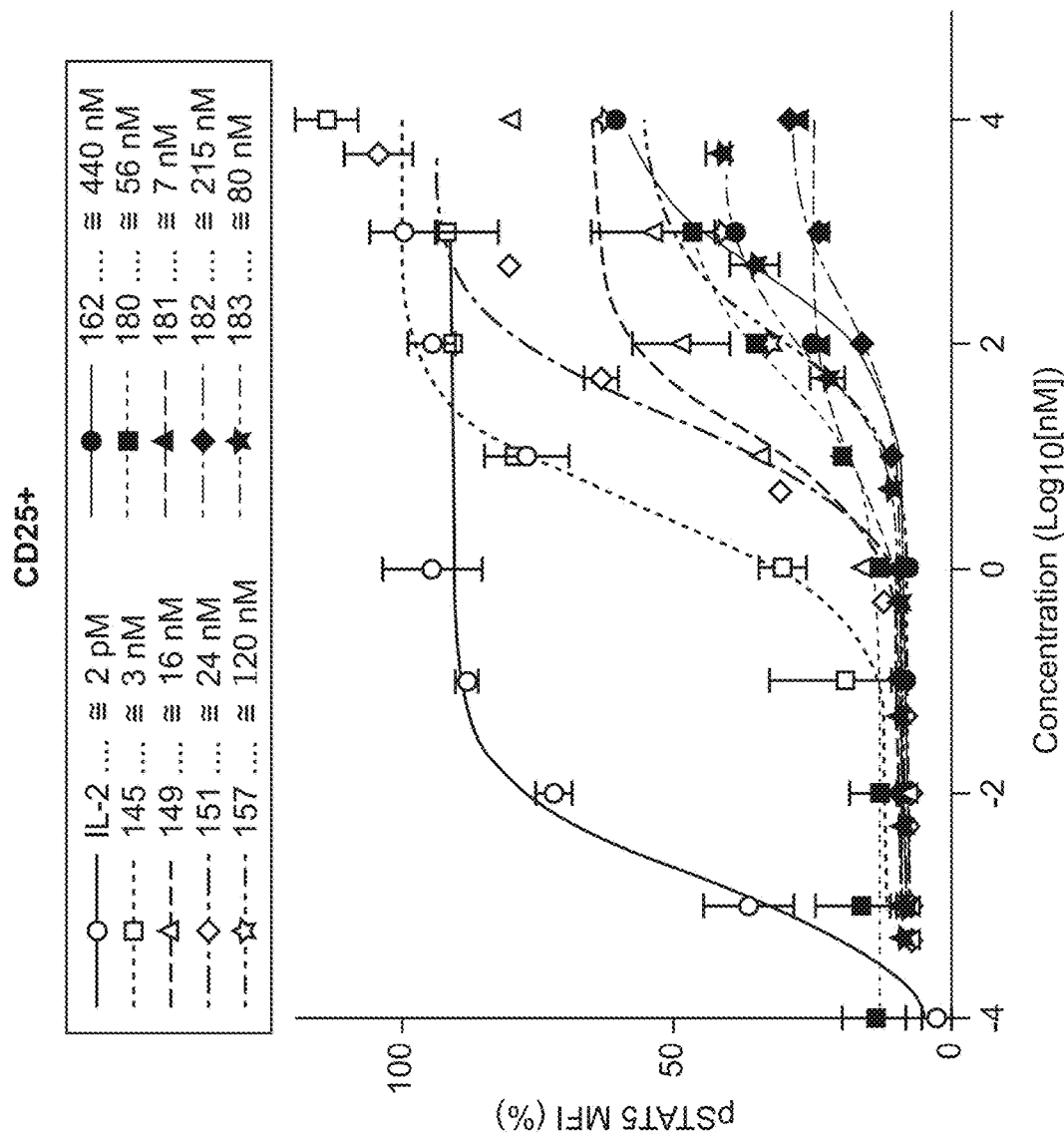
Figure 8B:
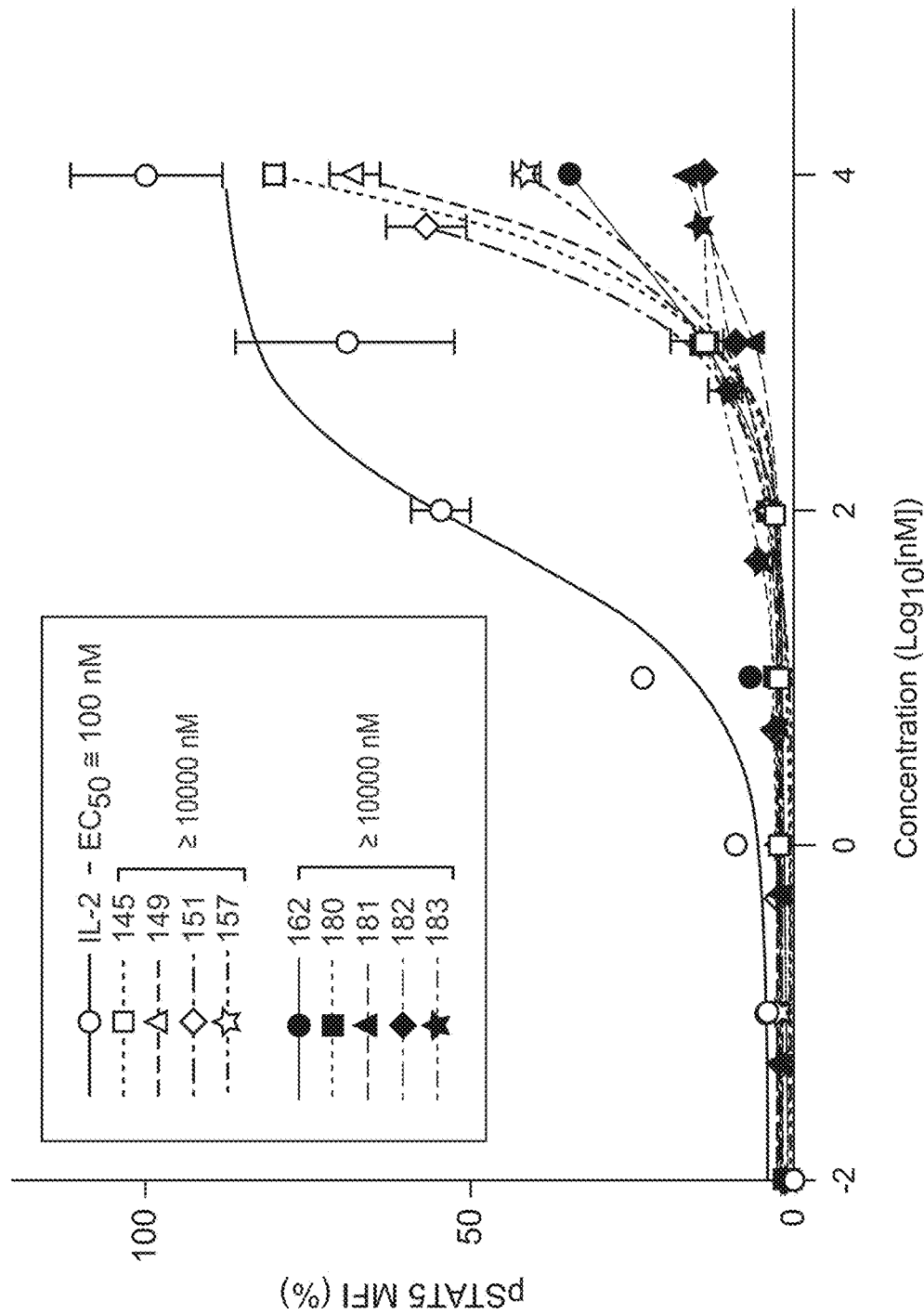

FIG. 8A-FIG. 8B. FIG. 8A-FIG. 8B. OrthoIL-2 variants exhibit blunted activity (phosphoSTAT5) on wild-type CD25 positive and CD25 negative Splenocytes FIG. 9. Generation of orthoIL-2R expressing mouse CTLL-2 T cells.

Figures 9, 10:
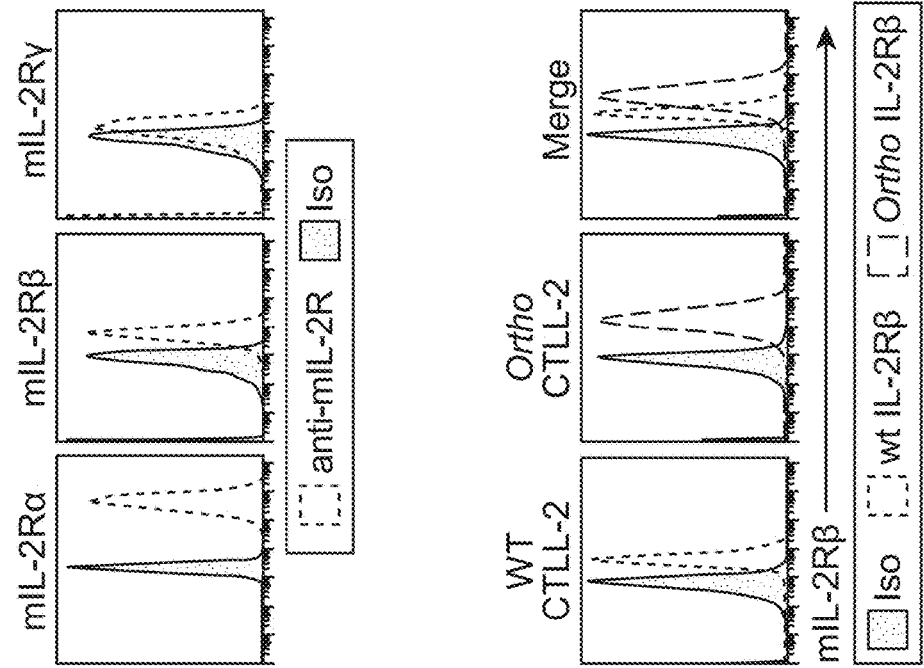
Figure 11E:
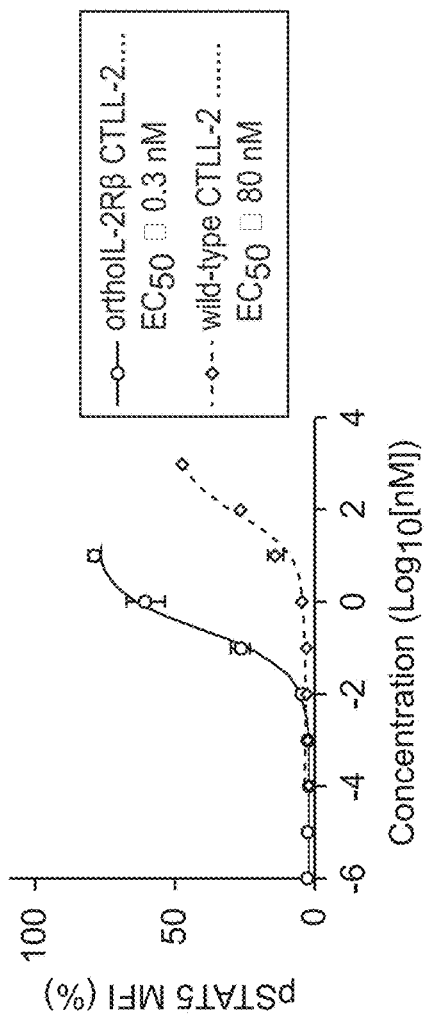
Figure 11F:
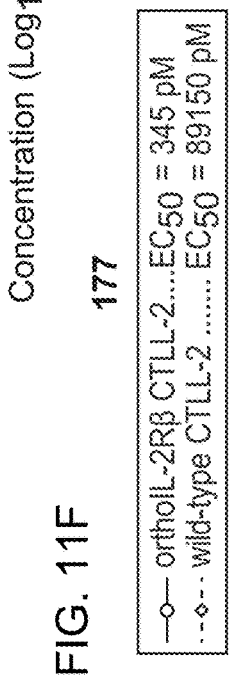
Figure 11G:
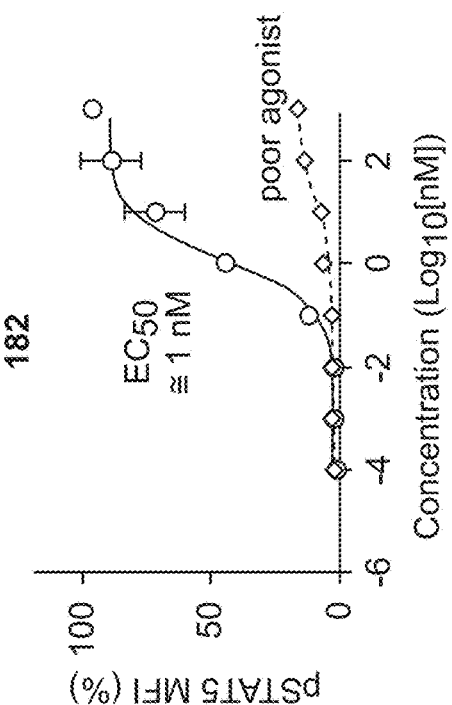

FIG. 10. First set of orthoIL-2 variants are selective for ortho T cells.

FIG. 11A-FIG. 11G. FIG. 11A-FIG. 11G. OrthoIL-2 variants induce selective STAT5 phosphorylation on orthoIL-2Rβ expressing CTLL-2 cells.

Figure 12A:
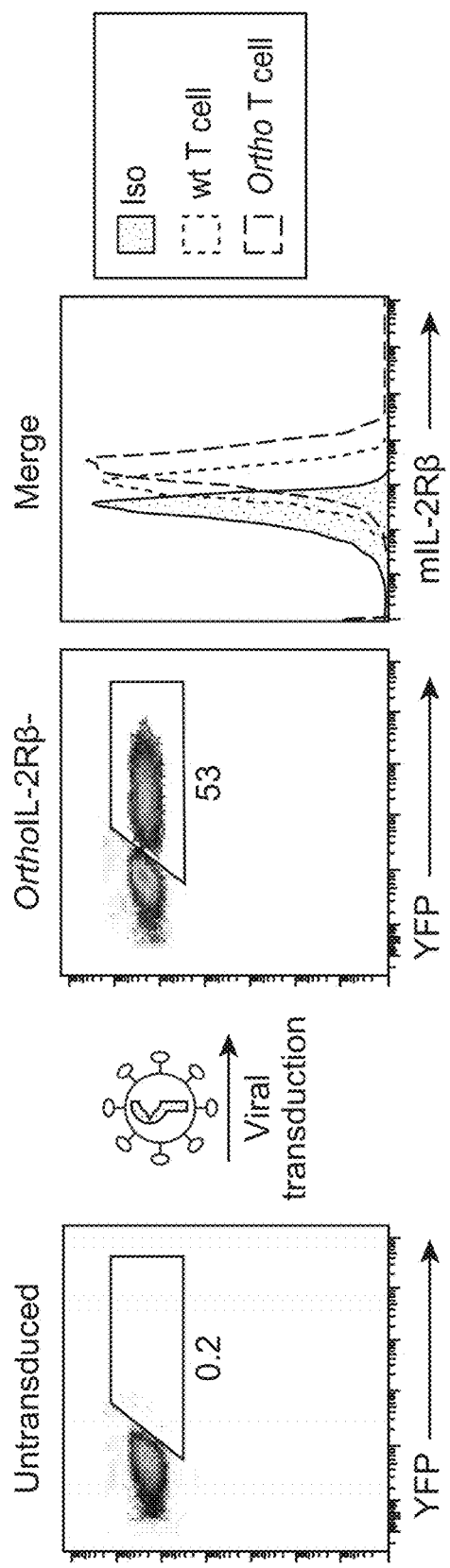
Figure 12B:
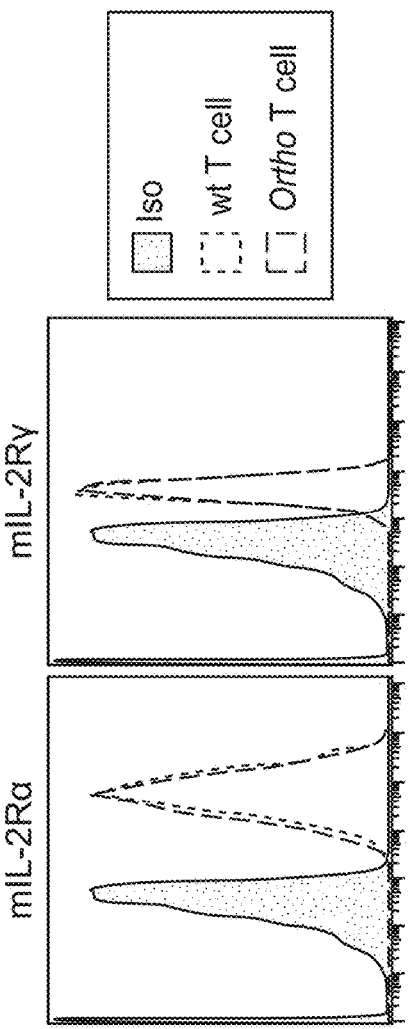

FIG. 12A-FIG. 12B. FIG. 12A-FIG. 12B. Primary lymph node derived T cells engineered to express orthoIL-2Rβ (H134D Y135F).

FIG. 13A-FIG. 13D FIG. 13A-FIG. 13D. OrthoIL-2 variants induce selective STAT5 phosphorylation on orthoIL-2Rβ expressing primary mouse T cells.

Figure 14A:
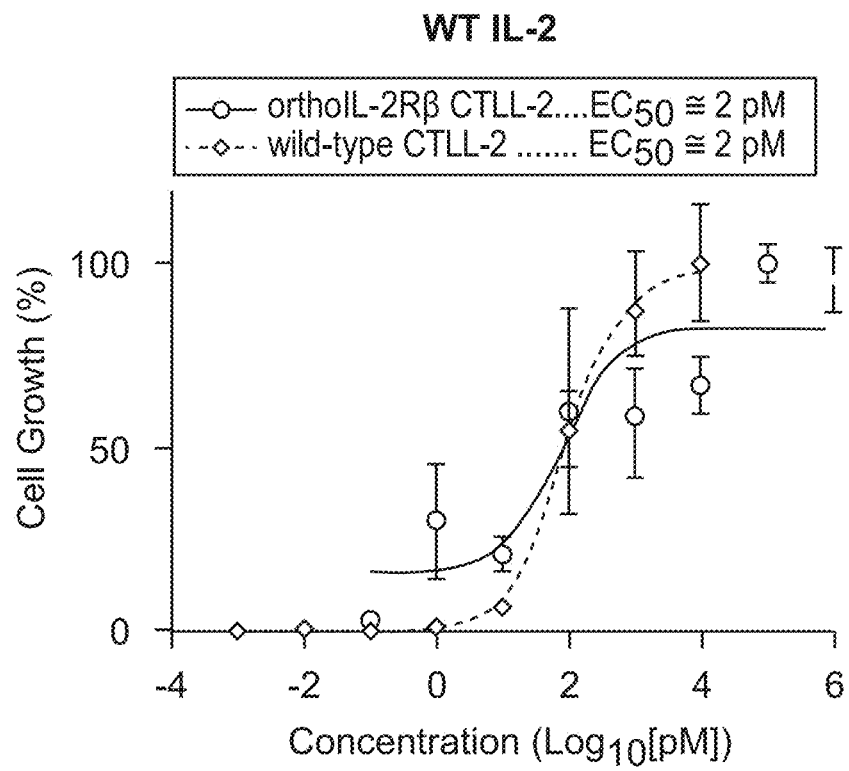
Figure 14B:
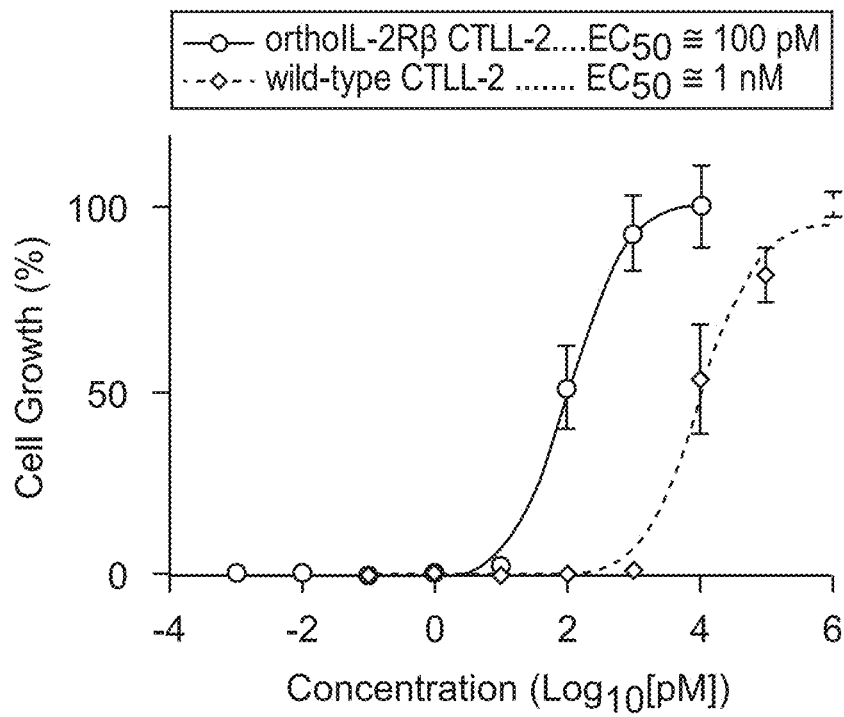
Figure 16A:
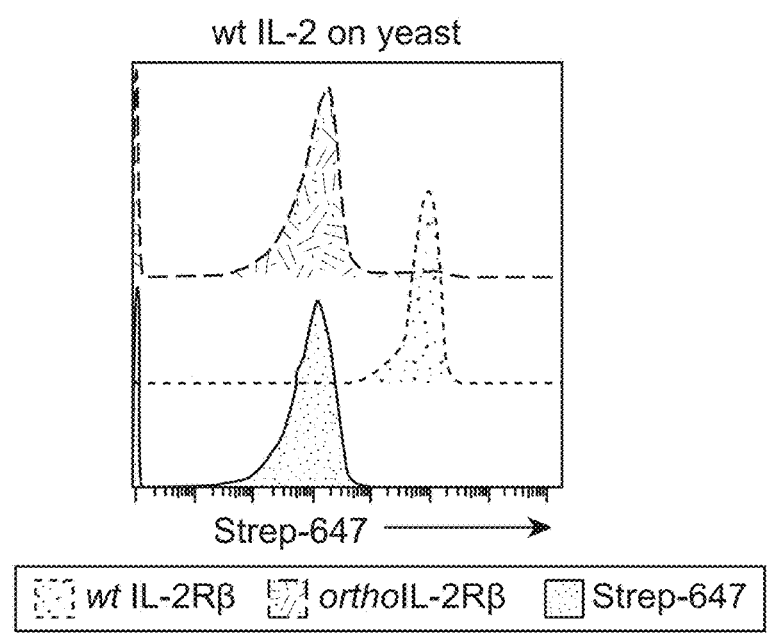
Figure 16B:
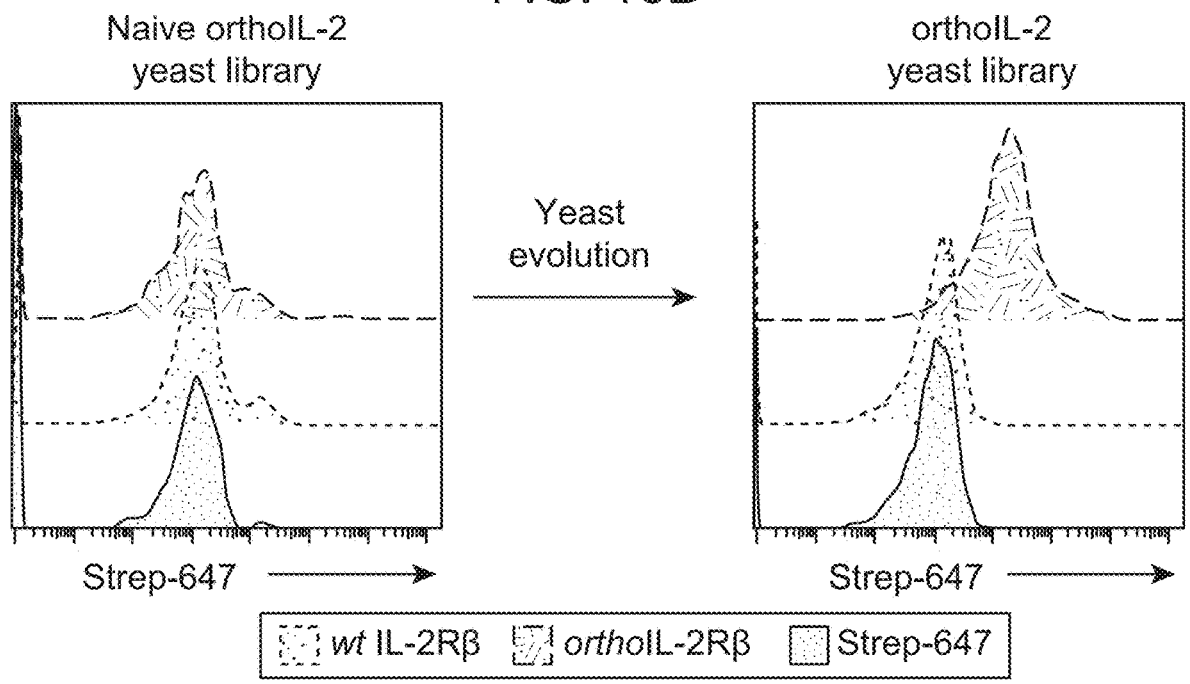

FIG. 14A-FIG. 14B. FIG. 14A-FIG. 14B. OrthoIL-2 variants induce selective cell growth of orthoIL-2Rβ expressing CTLL-2 cells compared to wild-type T cells.

FIG. 15. Alignment of mouse and human reference IL-2Rβ/IL-2 sequences. A partial sequence of human IL-2Rβ is provided as SEQ ID NO:1, residues 1-235; a partial sequence of mouse IL-2Rβ is provided as SEQ ID NO:2, residues 1-238. Mouse IL-2 is provided as SEQ ID NO:3. Human IL-2 is provided as SEQ ID NO:4.

FIG. 16A-16D. Yeast evolution of orthogonal human IL-2 pairs. (FIG. 16A) FACS analysis of yeast-displayed wild-type human IL-2 binding to wild-type but not the ortho human IL-2Rβ H133D Y134F mutant tetramers. (FIG. 16B) Libraries of human IL-2 mutants (~$1^8$ mutants) that randomize IL-2 residues predicted to be in proximity to or contacting the human IL-2Rβ HY mutant were displayed on the surface of yeast. After successive rounds of rounds of both positive (against ortho hIL-2Rβ) and negative (against wild-type hIL-2Rβ) selection, we obtained yeast-displayed human IL-2 mutants that bind ortho but not wild-type human IL-2Rβ tetramers. (FIG. 16C, 16D) ortho hIL-2 mutants were subsequently isolated and sequenced from the yeast library. A consensus set of mutations were identified indicating a convergence of ortho hIL-2 sequences capable of binding the ortho hIL-2Rβ.

Figure 17:
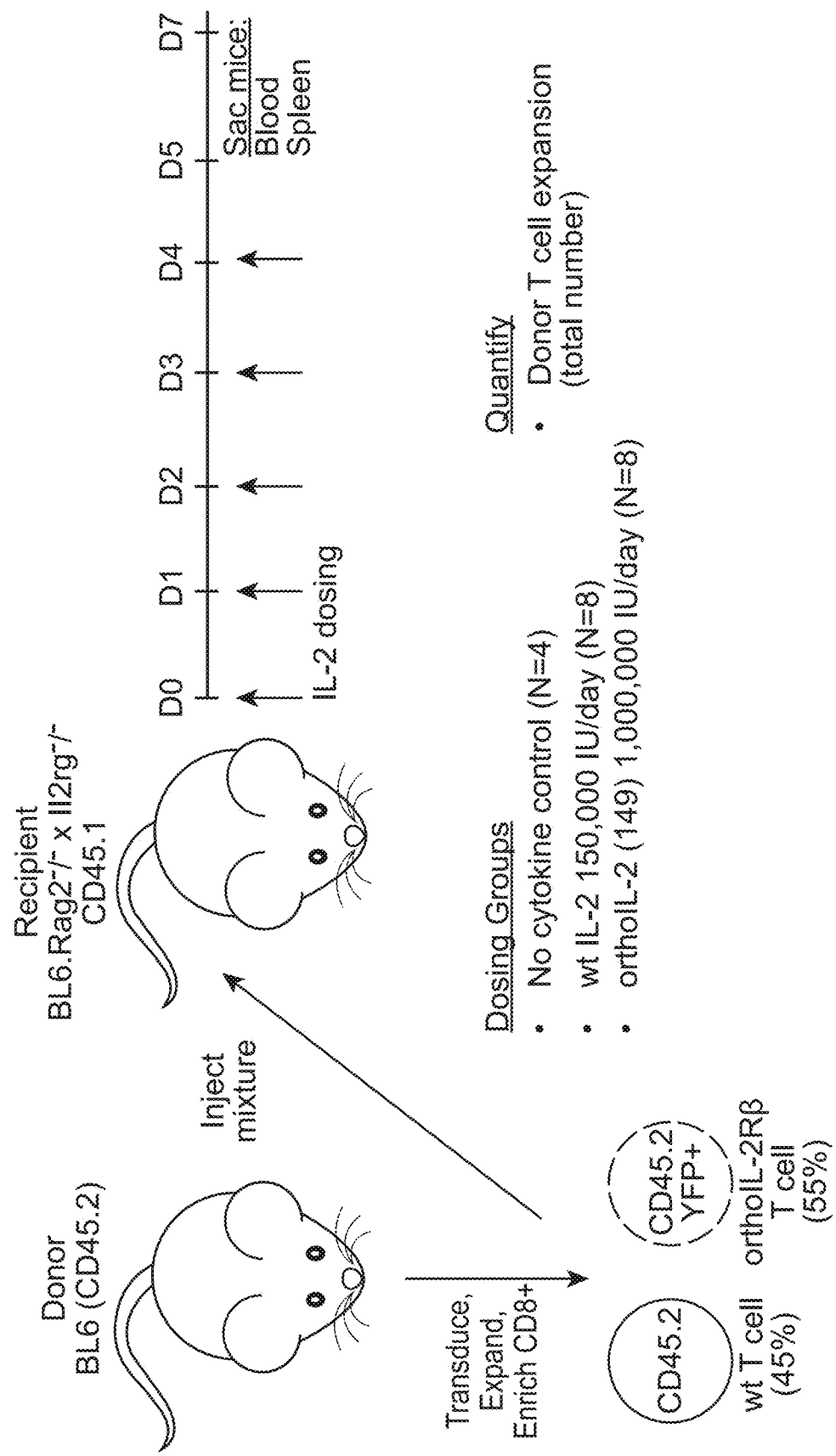

FIG. 17. In vivo mouse model used to demonstrate selective expansion or increased survival of orthogonal IL-2Rb expressing T cells in mice. Donor cells were isolated from the spleen of wild-type C57BL/6J mice that express CD45.2, activated ex vivo with CD3/CD28, transduced with retrovirus encoding orthogonal IL-2Rb-IRES-YFP, expanded for 2 days in 100 IU/mL mIL-2, and purified using a mouse CD8 T cell isolation kit (Miltenyi). An ~1:1 mixture of wild-type (CD45.2 positive, YFP negative) and orthogonal IL-2Rb expressing T cells (CD45.2 positive, YFP positive) were adoptively transferred into recipient BL6.Rag2$^{-/-}$×IL2rg$^{-/-}$ CD45.1 mice via retro-orbital injection. PBS, wild-type mIL-2 (150,000 IU/mouse), or orthoIL-2 clone 1G12/149 (1,000,000 IU/mouse), were injected IP daily beginning immediately after T cell transfer (d0) and at 24 hr intervals for 5 consecutive days (up to d4). Mice were sacrificed on d5 and d7 and total donor T cell counts in the blood and spleen of mice were quantified by flow cytometry.

Figure 18A:
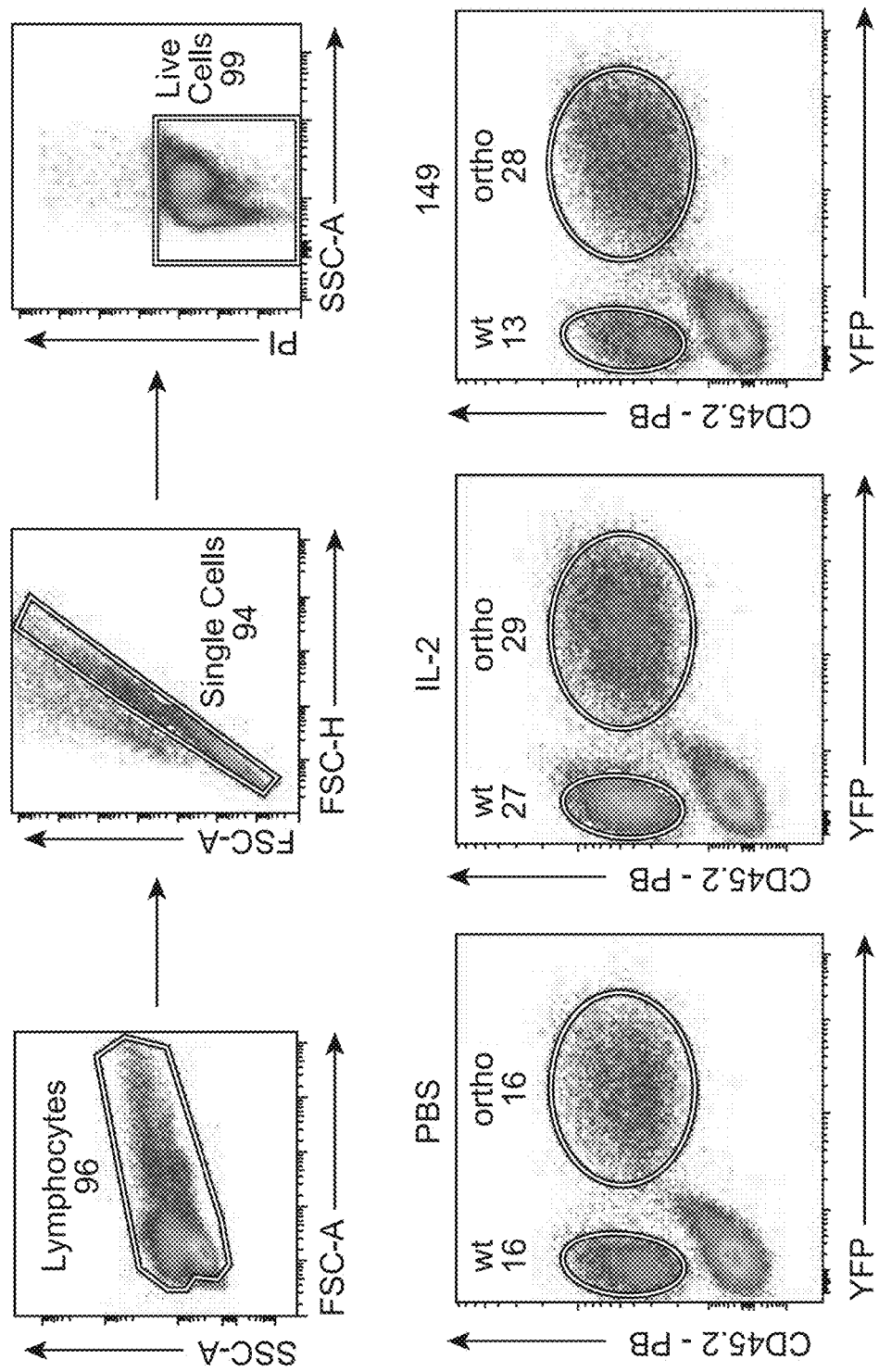
Figure 18B:
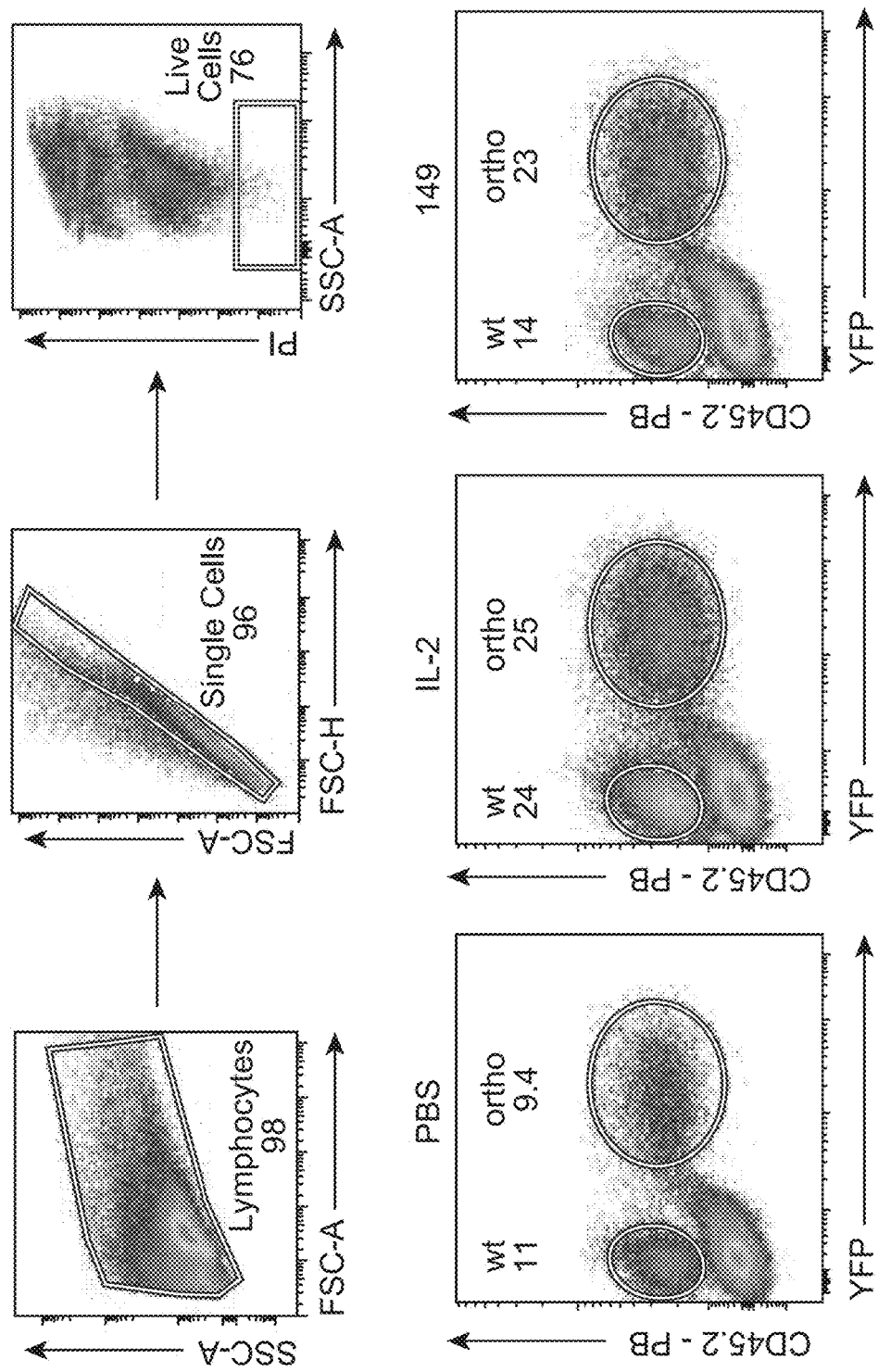

FIG. 18A-18B. Gating strategy used to quantify donor T cell expansion in recipient mice. Single cell suspension from mouse blood and spleen were prepared and stained with CD45.2-pacific blue for 1 hr at 4C for identification of donor T cells. Immediately prior to flow cytometry cells were incubated with a 1:2000 dilution of propidium iodide (PI) for live/dead exclusion. Cells were gated based on forward and side scatter (SSC-A v FSC-A), singlets (FSC-A v FSC-H), live cells (PI negative), and the total number of wild-type T cells (CD45.2 positive, YFP-negative) and orthogonal T cells (CD45.2 positive, YFP-positive) was quantified via FACS.  p<0.01, * p<0.001, **** p<0.0001, determined by one-way ANOVA using Prism.

Figure 19:
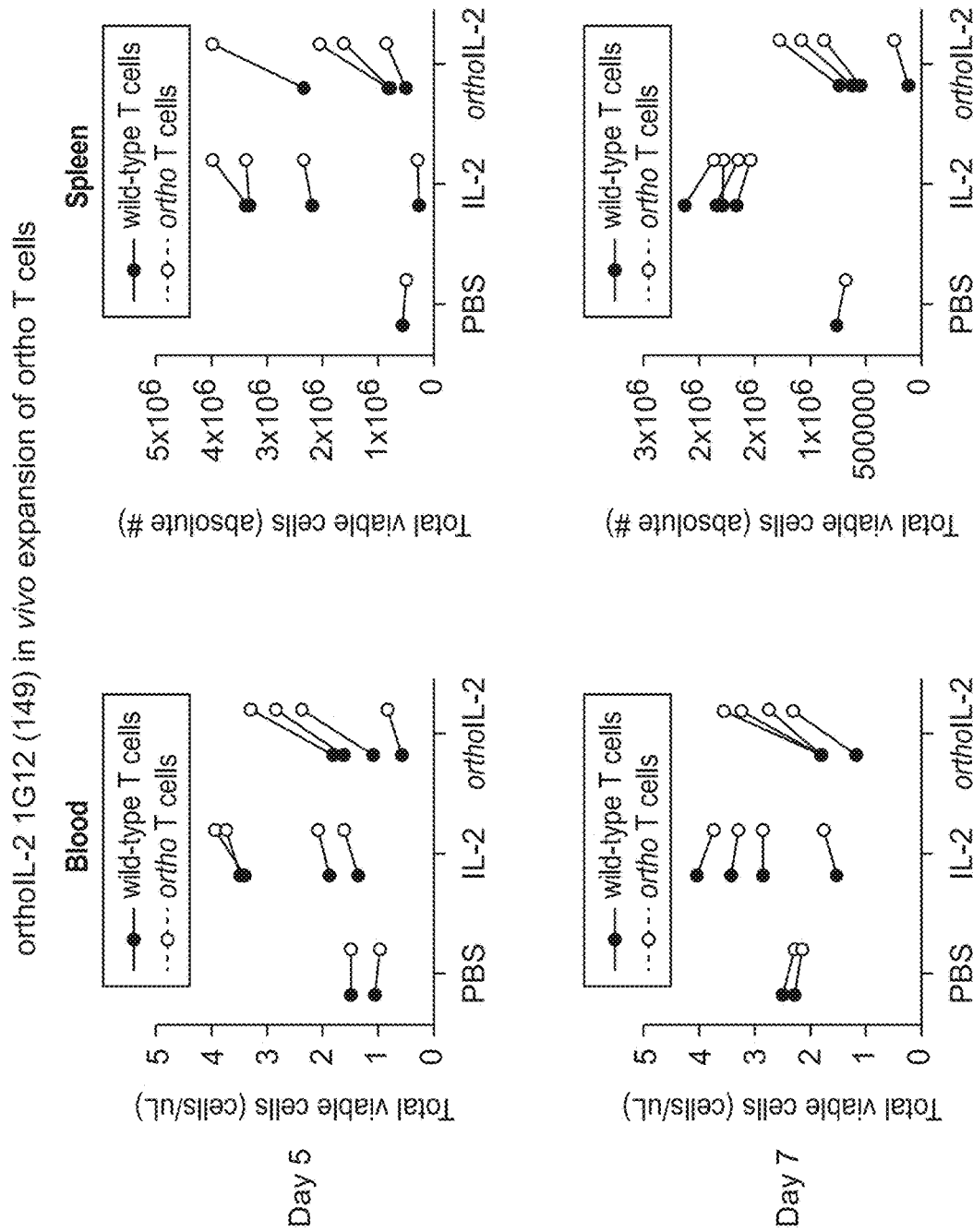

FIG. 19. orthoIL-2 clone 1G12/149 selectively expands orthogonal but not wild-type T cells in mice. The number of wild-type and orthogonal T cells in blood ($10^3$ cells/uL) and spleen (total number of cells per spleen) were quantified via flow cytometry as described in FIG. 18. The ratio of orthogonal T cells to wild-type T cells was determined by dividing the total number orthogonal T cells by the total number of wild-type T cells in the blood and spleen. A ratio greater than 1 indicates selective expansion of orthogonal T cells, which is achieved with orthoIL-2 clone 1G12/149. Total number of viable cells in the blood (left) and spleen (right) at day 5 (top) and day 7 (bottom) were quantified via flow cytometry. Treatment with wild-type IL-2 results in expansion of both wild-type and ortho T cells compared to a PBS control, whereas treatment with orthoIL-2 clone 1G12/149 selectively expands ortho T cells with limited activity on wild-type T cells.

Figure 20B:
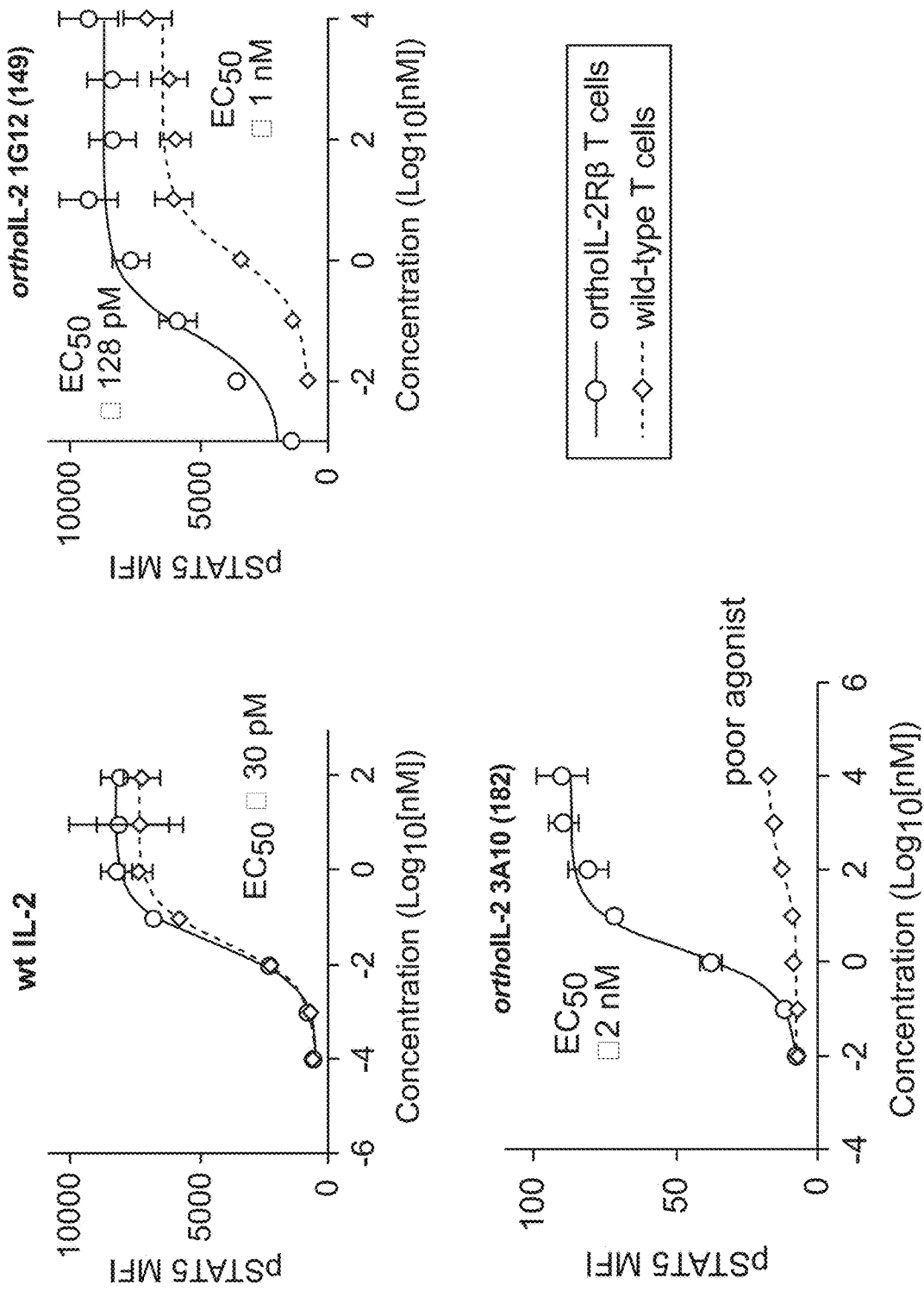

FIG. 20A-20B. Orthogonal IL-2 has selective activity on orthogonal IL-2Rβ T cells. (FIG. 20A) FACS analysis of primary, spleen derived mouse T cells isolated from IL-2 KO NOD mice and virally transduced to express orthoIL-2Rβ, which can be confirmed using an IRES-YFP reporter and surface staining for IL-2Rβ. The T cells also retain expression of wild-type IL-2Rβ (FIG. 20B) orthoIL-2 induces selective STAT5 phosphorylation on orthoIL-2Rβ expressing T cells with blunted to no activity on wild-type T cells.

Figure 21B:
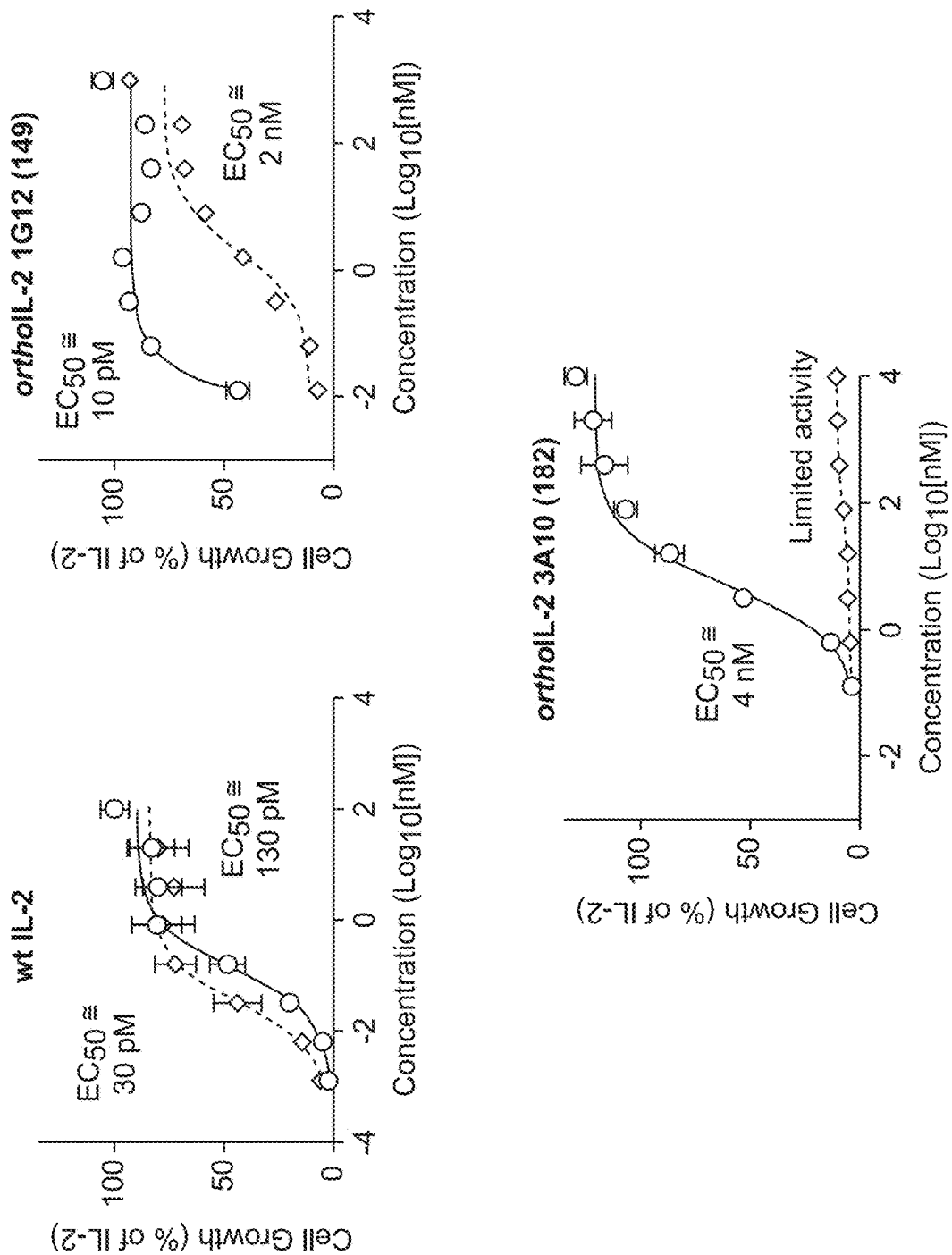
Figure 22A:
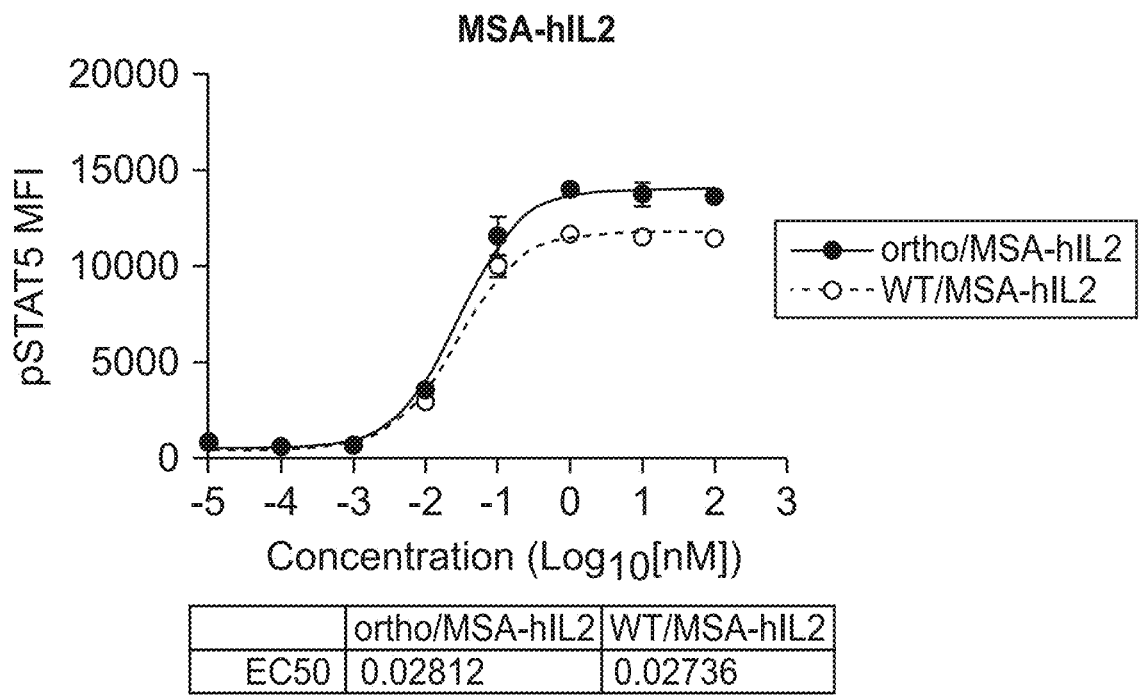
Figure 22B:
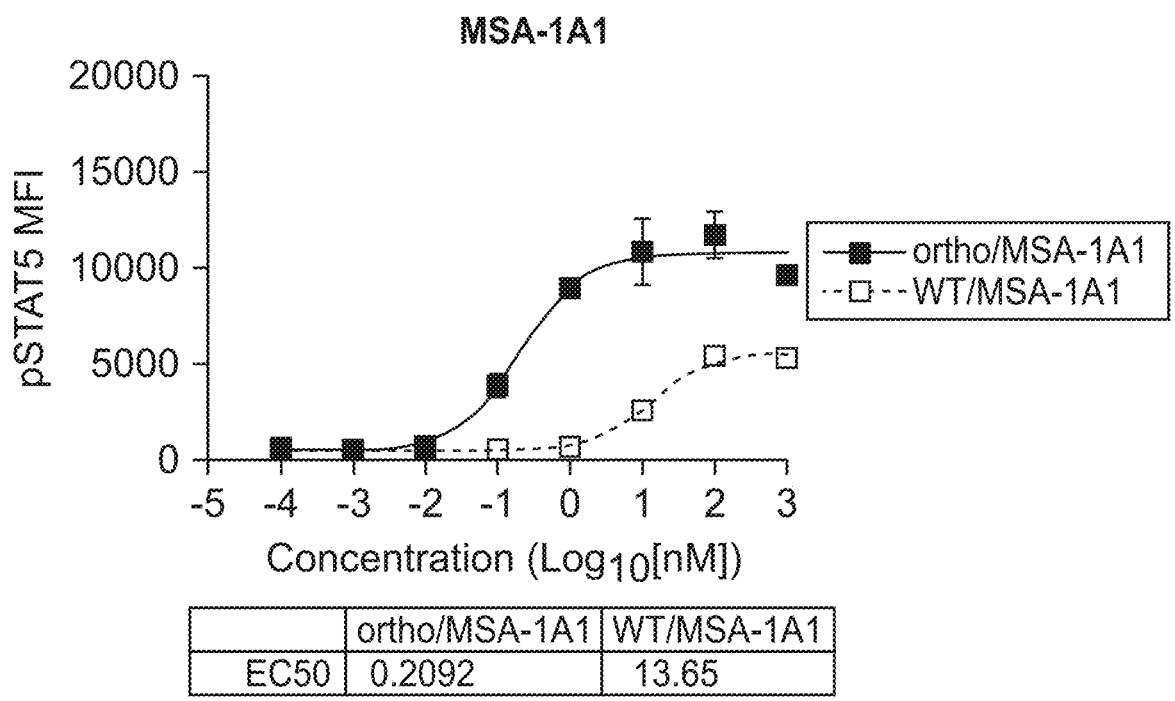
Figure 22C:
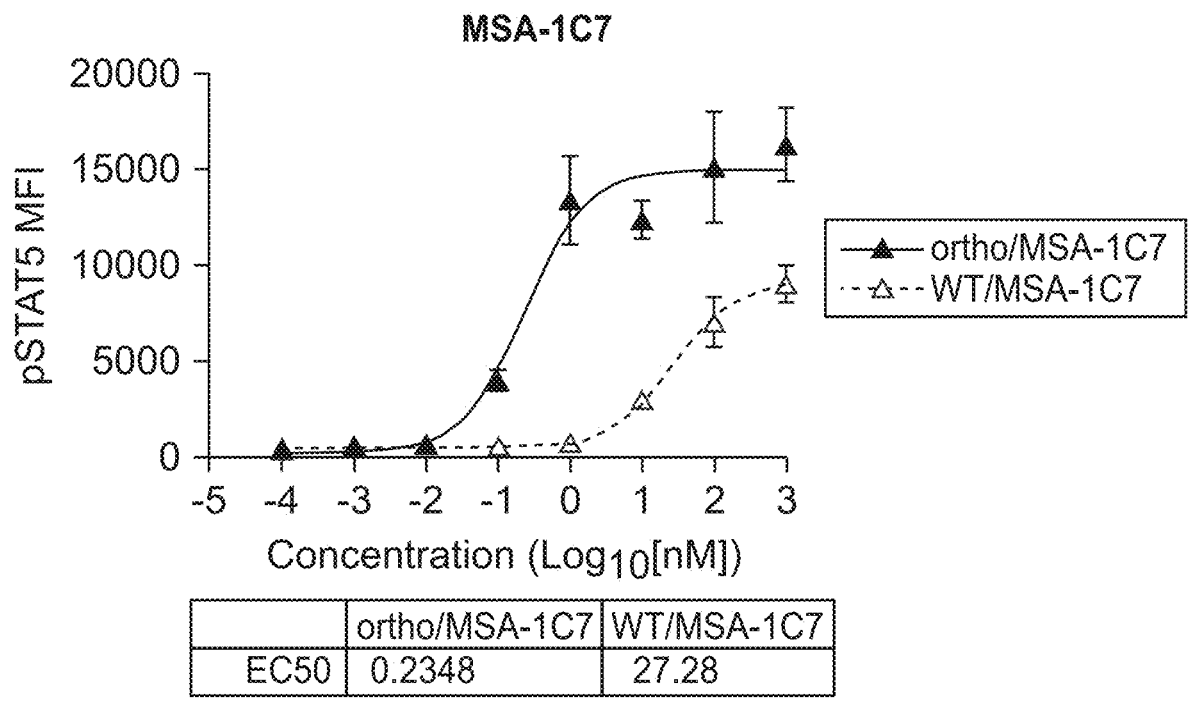
Figure 22D:
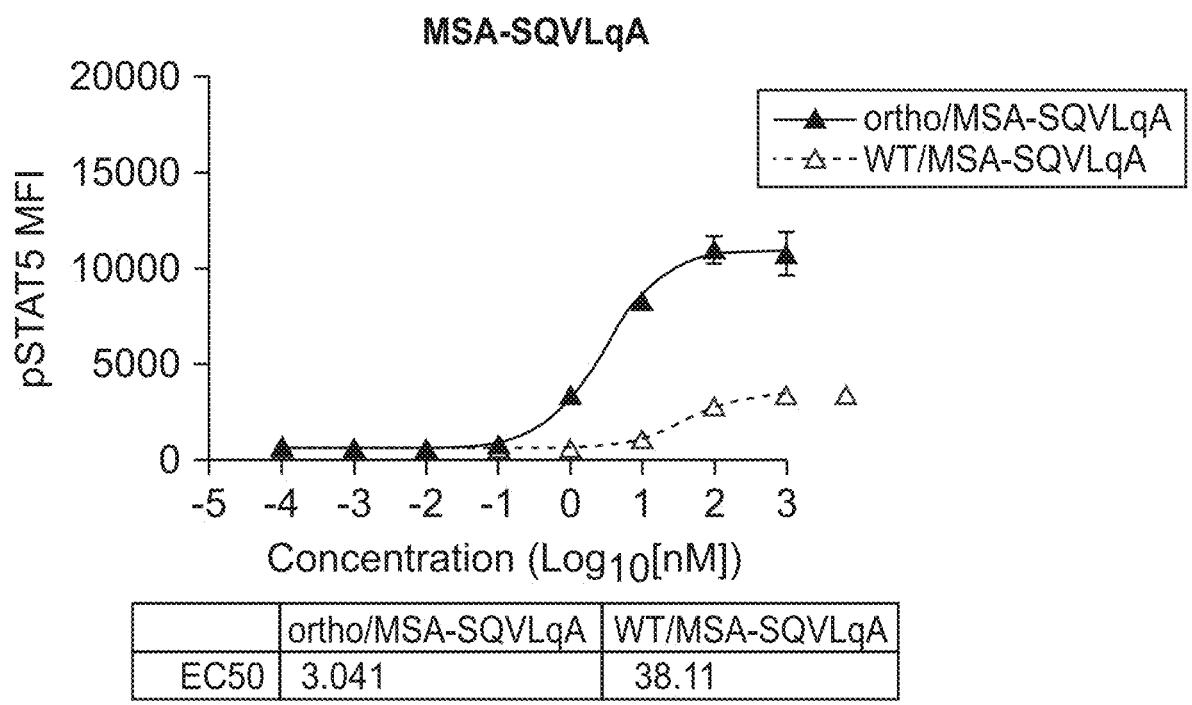

FIG. 21A-21B. Orthogonal IL-2 selectively expands orthogonal IL-2Rβ T cells in vitro. (FIG. 21A) FACS analysis of primary, spleen derived mouse T cells virally transduced to express orthoIL-2Rβ, which can be confirmed using an IRES-YFP. The mixture of transduced and un-transduced T cells were cultured for 5 days in various concentrations of wild-type, orthoIL-2 clone 1G12, or 3A10 and analyzed by FACS. IL-2 expands both wild-type and ortho T cells, whereas only ortho T cells expand when cultured in orthoIL-2 3A10 whereas orthoIL-2 1G12 selectively expands ortho T cells with significantly reduced activity on wild-type T cells. The FACS plot show correspond to culture in 100 nM IL-2, 64 pM orthoIL-2 1G12, and 10 uM orthoIL-2 3A10. (FIG. 21B) Wild-type and ortho T cell proliferation dose-response to wild-type and orthoIL-2 clones 1G12 and 3A10 after 5 days of culture in increasing concentrations of cytokine. IL-2 expands both wild-type and ortho T cells with equal potency, orthoIL-2 1G12 selectively expands ortho T cells, and orthoIL-2 3A10 specifically expands ortho T cells.

FIG. 22A-22E. Ortho human IL-2 signals through the orthoIL-2R expressed in YT cells in vitro. Dose-response of STAT5 phosphorylation after 20 min of stimulation. The phosphorylation of Stat5 was measured in the YT human NK cell line, expressing human CD25 (YT+), without (YFP−, WT) or with (YFP+, ortho) human ortho IL-2Rb. (FIG. 22A) Mouse serum albumin (MSA) fusions of human IL-2, or orthogonal variants (FIG. 22B) 1A1, (FIG. 22C) 1C7, (FIG. 22D) SQVLKA or (FIG. 22E) SQVKqA were titrated in RPMI complete media and added to the cells. The mean fluorescence intensities (MFI) of APC-pStat5 staining for WT (YFP−) and ortho Rb (YFP+) cells were plotted versus the concentration of cytokine, and fit to a log(agonist) vs. response (three parameters) model using Prism 5 (GraphPad). 1C7 was run on a separate day from the other proteins, and was normalized to wild type IL-2 staining run on both days. All data are presented as mean (n=3)±SD.

Figure 23A:
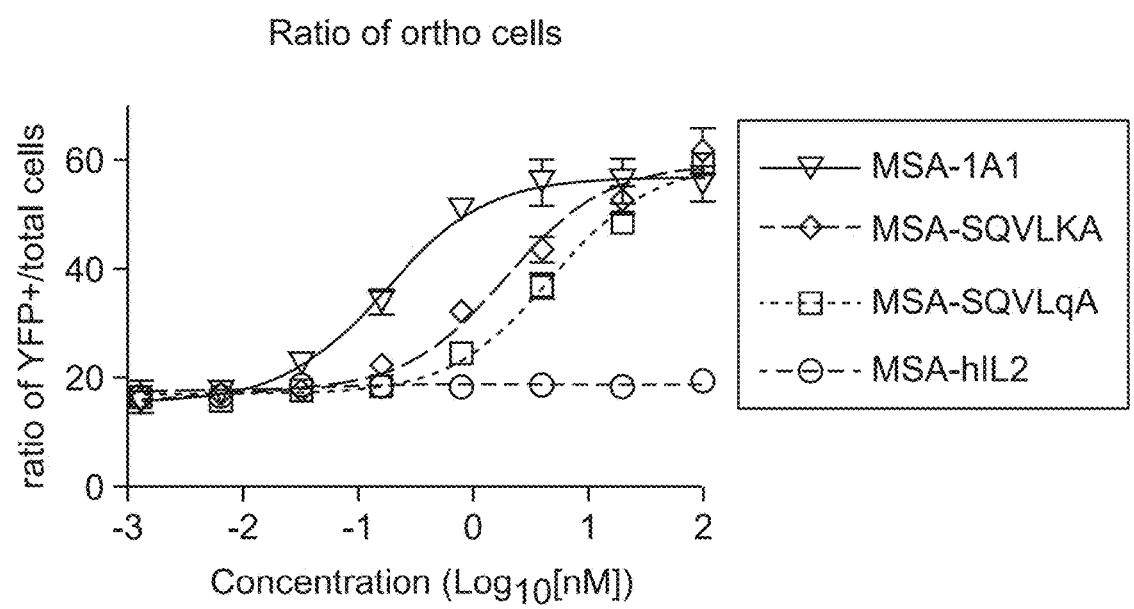
Figure 23B:
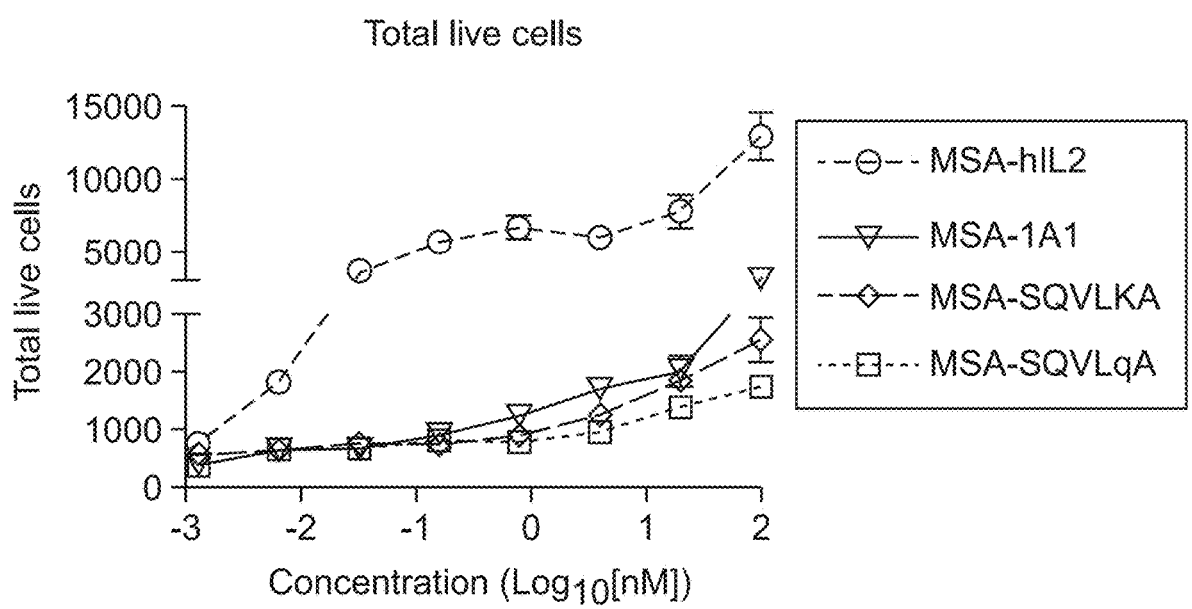

FIG. 23A-23B. Ortho human IL-2 preferentially expands human PBMCs expressing the ortho IL-2R. Human PBMCs were isolated, activated and transformed with retrovirus containing ortho human IL-2Rβ with an IRES YFP (YFP+). Initial ratio of YFP+ cells to total live cells was 20%. $5 \times 10^5$ cells were plated with the indicated concentrations of MSA-human IL-2 or ortho variants MSA-SQVLKA, MSA-SQVLqA or MSA-1A1 (black triangles) on day 1, and re-fed the same concentration on day 3. On day 5 the plate was read by flow cytometry. (FIG. 23A) The ratio of YFP+(ortho expressing) cells to total live cells was calculated, and the mean (n=4)±SD was plotted versus the concentration (left). (FIG. 23B) Total live cell counts (mean (n=4)±SD) were also plotted versus the cytokine concentration (right). The orthogonal cytokines were unable to support as much total cell growth as wild type MSA-hIL-2 at the same concentration.

DETAILED DESCRIPTION OF THE EMBODIMENTS

In order for the present disclosure to be more readily understood, certain terms and phrases are defined below as well as throughout the specification. The definitions provided herein are non-limiting and should be read in view of what one of skill in the art would know at the time of invention.

Definitions

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Cytokine receptor and ligand pairs include, without limitation, the following receptors:

| Cytokine | Receptor subunits |
|---|---|
| IL-1-like | |
| IL-1α | CD121a, CDw121b |
| IL-1β | CD121a, CDw121b |
| IL-1RA | CD121a |
| IL-18 | IL-18Rα, β |
| IL-2 | CD25, 122,132 |
| IL-4 | CD124,213a13, 132 |
| IL-7 | CD127, 132 |
| IL-9 | IL-9R, CD132 |
| IL-13 | CD213a1, 213a2, CD1243, 132 |
| IL-15 | IL-15Rα, CD122, 132 |
| IL-3 | CD123, CDw131 |
| IL-5 | CDw125, 131 |
| GM-CSF | CD116, CDw131 |

-continued

| Cytokine | Receptor subunits |
| --- | --- |
| IL-6 | CD126, 130 |
| IL-11 | IL-11Ra, CD130 |
| G-CSF | CD114 |
| IL-12 | CD212 |
| LIF | LIFR, 0D130 |
| OSM | OSMR, CD130 |
| IL-10 | CDw210 |
| IL-20 | IL-20Rα, β |
| IL-14 | IL-14R |
| IL-16 | CD4 |
| IL-17 | CDw217 |
| IFN-α | CD118 |
| IFN-β | CD118 |
| IFN-γ | CDw119 |
| CD154 | CD40 |
| LT-β | LTβR |
| TNF-α | CD120a, b |
| TNF-β | CD120a, b |
| 4-1BBL | CDw137 (4-1BB) |
| APRIL | BCMA, TACI |
| CD70 | CD27 |
| CD153 | CD30 |
| CD178 | CD95 (Fas) |
| GITRL | GITR |
| LIGHT | LTbR, HVEM |
| OX4OL | OX40 |
| TALL-1 | BCMA, TACI |
| TRAIL | TRAILR1-4 |
| TWEAK | Apo3 |
| TRANCE | RANK, OPG |
| TGF-β1 | TGF-βR1 |
| TGF-β2 | TGF-βR2 |
| TGF-β3 | TGF-βR3 |
| Epo | EpoR |
| Tpo | TpoR |
| Flt-3L | Flt-3 |
| SCF | CD117 |
| M-CSF | CD115 |
| MSP | CDw136 |

An "ortholog", or "orthologous cytokine/receptor pair" refers to a genetically engineered pair of proteins that are modified by amino acid changes to (a) lack binding to the native cytokine or cognate receptor; and (b) to specifically bind to the counterpart engineered (orthogonal) ligand or receptor. Upon binding, the orthogonal receptor activates signaling that is transduced through native cellular elements to provide for a biological activity that mimics that native response, but which is specific to an engineered cell expressing the orthogonal receptor. The orthogonal receptor does not bind to the endogenous counterpart cytokine, including the native counterpart of the orthogonal cytokine, while the orthogonal cytokine does not bind to any endogenous receptors, including the native counterpart of the orthogonal receptor. In some embodiments, the affinity of the orthogonal cytokine for the orthogonal receptor is comparable to the affinity of the native cytokine for the native receptor, e.g. having an affinity that is least about 1% of the native cytokine receptor pair affinity, at least about 5%, at least about 10%, at least about 25%, at least about 50%, at least about 75%, at least about 100%, and may be higher, e.g. 2×, 3×, 4×, 5×, 10× or more of the affinity of the native cytokine for the native receptor As used herein, "do not bind" or "incapable of binding" refers to no detectable binding, or an insignificant binding, i.e., having a binding affinity much lower than that of the natural ligand. The affinity can be determined with competitive binding experiments that measure the binding of a receptor with a single concentration of labeled ligand in the presence of various concentrations of unlabeled ligand. Typically, the concentration of unlabeled ligand varies over at least six orders of magnitude. Through competitive binding experiments, $IC_{50}$ can be determined. As used herein, "$IC_{50}$" refers to the concentration of the unlabeled ligand that is required for 50% inhibition of the association between receptor and the labeled ligand. $IC_{50}$ is an indicator of the ligand-receptor binding affinity. Low $IC_{50}$ represents high affinity, while high $IC_{50}$ represents low affinity.

Interleukin 2 (IL-2) is a pluripotent cytokine produced primarily by activated CD4$^+$ T cells and plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer (aldesleukin, Proleukin®). In eukaryotic cells human IL-2 is synthesized as a precursor polypeptide of 153 amino acids, from which 20 amino acids are removed to generate mature secreted IL-2.

As used herein, "IL-2" refers to the native, or wild-type IL-2. Mature human IL-2 occurs as a 133 amino acid sequence (less the signal peptide, consisting of an additional 20 N-terminal amino acids), as described in Fujita, et. al, PNAS USA, 80, 7437-7441 (1983). The amino acid sequence of human IL-2 is found in Genbank under accession locator NP 000577.2. Reference sequences of the human and mouse IL-2 and IL-2Rβ are provided in FIG. 15.

IL-2 supports the survival and differentiation of T lymphocytes by initiating cell signaling pathways upon interaction with the IL-2 receptor (IL-2R). IL-2 is used clinically to treat a number of human diseases including cancer and autoimmunity, and as an adjuvant to adoptive T cell therapies to promote the survival of transplanted T cells. However, IL-2 can also have apposing effects by activating off-target cell types. To direct the activity of IL-2 towards a specific T cell subset, the present invention provides engineered orthogonal IL-2 and IL-2 receptor pairs. Orthogonal IL-2 recapitulates the activity of wild-type IL-2 by inducing potent STAT5 phosphorylation and in vitro proliferation of T cells engineered to express the orthogonal IL-2Rbeta. Orthogonal IL-2 has limited or no activity on ex vivo cultured wild-type CD25 positive or negative mouse T cells, respectively. These studies indicate that remodeling cytokine receptor interfaces to create interactions that are not present in nature is a viable strategy to direct the activity of a promiscuous cytokine to a T cell subset of interest, thereby enabling precise control over T cell function though genetic engineering.

In addition to IL-2, IL-15 and IL-7 also regulate lymphoid homeostasis and have also been used as adjuvants to potentiate adoptive T cell therapy. IL-2 and IL-15 share the same IL-2R-beta chain. Orthogonal IL-15 can be selected against the identical orthogonal IL-2R-beta used to orthgonalize IL-2. IL-7 utilizes a distinct IL-7R-alpha chain that is a target for orthogonalization.

Orthogonal IL-2 can be fused to the Fc domain of IgG, albumin, or other molecules to extend its half-life, e.g. by pegylation, glycosylation, and the like as known in the art. Fc-fusion can also endow alternative Fc receptor mediated properties in vivo. The "Fc region" can be a naturally occurring or synthetic polypeptide that is homologous to an IgG C-terminal domain produced by digestion of IgG with papain. IgG Fc has a molecular weight of approximately 50 kDa. The ortholog IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

In other embodiments, an orthologous polypeptide can comprise polypeptide that functions as an antigenic tag, such as a FLAG sequence. FLAG sequences are recognized by biotinylated, highly specific, anti-FLAG antibodies, as described herein (see also Blanar et al., Science 256: 1014, 1992; LeClair et al., Proc. Natl. Acad. Sci. USA 89:8145, 1992). In some embodiments, the chimeric polypeptide further comprises a C-terminal c-myc epitope tag.

As described above, the orthologous proteins of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^1$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

Orthogonal cytokines and receptors may also include conservative modifications and substitutions at other positions of the cytokine (e.g. positions other than those involved in the orthogonal engineering). Such conservative substitutions include those described by Dayhoff in The Atlas of Protein Sequence and Structure 5 (1978), and by Argos in EMBO J., 8:779-785 (1989). For example, amino acids belonging to one of the following groups represent conservative changes: Group I: ala, pro, gly, gin, asn, ser, thr; Group II: cys, ser, tyr, thr; Group III: val, ile, leu, met, ala, phe; Group IV: lys, arg, his; Group V: phe, tyr, trp, his; and Group VI: asp, glu.

The term "T cells" refers to mammalian immune effector cells that may be characterized by expression of CD3 and/or T cell antigen receptor, which cells may be engineered to express an orthologous cytokine receptor. In some embodiments the T cells are selected from naïve CD8$^+$ T cells, cytotoxic CD8$^+$ T cells, naïve CD4$^+$ T cells, helper T cells, e.g. $T_H1$, $T_H2$, $T_H9$, $T_H11$, $T_H22$, $T_{FH}$; regulatory T cells, e.g. $T_R1$, natural $T_{Reg}$, inducible $T_{Reg}$; memory T cells, e.g. central memory T cells, effector memory T cells, NKT cells, γδ T cells.

In some embodiments the T cells are contacted with the orthologous IL-2 in vivo, i.e. where the engineered T cells are transferred to a recipient, and an effective dose of the orthologous IL-2 is injected into the recipient and allowed to contact T cells in their native environment, e.g. in lymph nodes, etc. In other embodiments the contacting is performed in vitro.

T cells collected from a subject may be separated from a mixture of cells by techniques that enrich for desired cells. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The collected and optionally enriched cell population may be used immediately, or may be frozen at liquid nitrogen temperatures and stored, being thawed and capable of being reused. The cells will usually be stored in 10% DMSO, 50% FCS, 40% RPMI 1640 medium.

The engineered T cells may be infused to the subject in any physiologically acceptable medium, normally intravascularly, although they may also be introduced into any other convenient site, where the cells may find an appropriate site for growth. Usually, at least 1×10$^6$ cells/kg will be administered, at least 1×10$^7$ cells/kg, at least 1×10$^8$ cells/kg, at least 1×10$^9$ cells/kg, at least 1×10$^{10}$ cells/kg, or more, usually being limited by the number of T cells that are obtained during collection.

Expression construct: In the present methods, an orthologous protein, particularly the orthologous cytokine, may be produced by recombinant methods. The orthologous receptor may be introduced on an expression vector into the cell to be engineered. DNA encoding an orthologous protein may be obtained from various sources as designed during the engineering process.

Amino acid sequence variants are prepared by introducing appropriate nucleotide changes into the coding sequence, as described herein. Such variants represent insertions, substitutions, and/or specified deletions of, residues as noted. Any combination of insertion, substitution, and/or specified deletion is made to arrive at the final construct, provided that the final construct possesses the desired biological activity as defined herein.

The nucleic acid encoding an orthologous protein is inserted into a replicable vector for expression. Many such vectors are available. The vector components generally include, but are not limited to, one or more of the following: an origin of replication, one or more marker genes, an enhancer element, a promoter, and a transcription termination sequence. Vectors include viral vectors, plasmid vectors, integrating vectors, and the like.

An orthologous protein may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In mammalian cell expression the native signal sequence may be used, or other mammalian signal sequences may be suitable, such as signal sequences from secreted polypeptides of the same or related species, as well as viral secretory leaders, for example, the herpes simplex gD signal.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to an orthologous protein coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

Suitable host cells for cloning or expressing the DNA in the vectors herein are the prokaryote, yeast, or higher eukaryote cells described above. Examples of useful mammalian host cell lines are mouse L cells (L-M[TK-], ATCC #CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells, including engineered T cells, can be transfected with the above-described expression vectors for orthologous IL-2, or IL-2R expression. Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Recombinantly produced orthologous cytokines can be recovered from the culture medium as a secreted polypeptide, although it can also be recovered from host cell lysates. A protease inhibitor, such as phenyl methyl sulfonyl fluoride (PMSF) also may be useful to inhibit proteolytic degradation during purification, and antibiotics may be included to prevent the growth of adventitious contaminants. Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column. Also of interest is cation exchange chromatography.

The final orthologous cytokine composition may be concentrated, filtered, dialyzed, etc., using methods known in the art. For therapeutic applications, the cytokines can be administered to a mammal comprising the appropriate engineered orthologous receptor. Administration may be intravenous, as a bolus or by continuous infusion over a period of time. Alternative routes of administration include intramuscular, intraperitoneal, intra-cerobrospinal, subcutaneous, intra-articular, intrasynovial, intrathecal, oral, topical, or inhalation routes. The orthologous cytokines also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The polypeptide will typically be formulated in such vehicles at a concentration of about 0.1 µg/ml to 100 µg/ml.

In the event the ortholog IL-2 polypeptides of the disclosure are "substantially pure," they can be at least about 60% by weight (dry weight) the polypeptide of interest, for example, a polypeptide containing the ortholog IL-2 amino acid sequence. For example, the polypeptide can be at least about 75%, about 80%, about 85%, about 90%, about 95% or about 99%, by weight, the polypeptide of interest. Purity can be measured by any appropriate standard method, for example, column chromatography, polyacrylamide gel electrophoresis, or HPLC analysis.

In another embodiment of the invention, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the orthologous cytokine. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

The term "identity," as used herein in reference to polypeptide or DNA sequences, refers to the subunit sequence identity between two molecules. When a subunit position in both of the molecules is occupied by the same monomeric subunit (e.g., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "polypeptide," "protein" or "peptide" refer to any chain of amino acid residues, regardless of its length or post-translational modification (e.g., glycosylation or phosphorylation).

By "protein variant" or "variant protein" or "variant polypeptide" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild-type (or native) polypeptide, or a variant or engineered version of a wild-type polypeptide. Parent polypeptide may refer to the polypeptide itself, compositions that comprise the parent polypeptide, or the amino acid sequence that encodes it.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

As used herein, a "therapeutically effective amount" refers to that amount of the therapeutic agent, e.g. adoptive T cell and orthogonal cytokine combinations, sufficient to treat or manage a disease or disorder. A therapeutically effective amount may refer to the amount of therapeutic agent sufficient to delay or minimize the onset of disease, e.g., delay or minimize the spread of cancer, or the amount effect to decrease or increase signaling from a receptor of interest. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

As used herein, the terms "cancer" (or "cancerous"), "hyperproliferative," and "neoplastic" to refer to cells having the capacity for autonomous growth (e.g., an abnormal state or condition characterized by rapidly proliferating cell growth). Hyperproliferative and neoplastic disease states may be categorized as pathologic (e.g., characterizing or constituting a disease state), or they may be categorized as non-pathologic (e.g., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures.

Examples of tumor cells include but are not limited to AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia. Any cancer, where the cancer cells exhibit increased expression of CD47 compared to non-cancer cells, is a suitable cancer to be treated by the subject methods and compositions.

In other embodiments the methods of the invention are used in the treatment of infection. As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces increased CD47 expression in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

In yet other embodiments, regulatory T cells are engineered for the treatment of autoimmune disease. The spectrum of inflammatory diseases and diseases associated with inflammation is broad and includes autoimmune diseases such rheumatoid arthritis (RA), systemic lupus erythematosus (SLE), multiple sclerosis (MS), and autoimmune hepatitis; insulin dependent diabetes mellitus, degenerative diseases such as osteoarthritis (OA), Alzheimer's disease (AD), and macular degeneration.

Many, if not most, autoimmune and inflammatory diseases involve multiple types of T cells, e.g. TH1, TH2, TH17, and the like. Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease. Autoimmune diseases include diseases that affect specific tissues as well as diseases that can affect multiple tissues, which can depend, in part on whether the responses are directed to an antigen confined to a particular tissue or to an antigen that is widely distributed in the body.

Compositions and Methods

Engineered orthogonal cytokine receptor/ligand pairs, and methods of use thereof, are provided. An engineered (orthogonal) cytokine specifically binds to a counterpart engineered (orthogonal) receptor. Upon binding, the orthogonal receptor activates signaling that is transduced through native cellular elements to provide for a biological activity that mimics that native response, but which is specific to an engineered cell expressing the orthogonal receptor. The orthogonal receptor does not bind to the endogenous counterpart cytokine, including the native counterpart of the orthogonal cytokine, while the orthogonal cytokine does not bind to any endogenous receptors, including the native counterpart of the orthogonal receptor. In some embodiments, the affinity of the orthogonal cytokine for the orthogonal receptor is comparable to the affinity of the native cytokine for the native receptor.

The orthogonal cytokine and receptor pair may be selected from any cytokine of interest. The process for engineering an orthogonal cytokine receptor pair may comprise the steps of (a) engineering amino acid changes into a native receptor to disrupt binding to the native cytokine; (b) engineering amino acid changes into the native cytokine at contact residues for receptor binding, (c) selecting for cytokine orthologs that bind to the orthologous receptor; (d) discarding ortholog cytokines that bind to the native receptor, or (e) selecting for receptor orthologs that bind the ortholog cytokine; (f) discarding ortholog receptors that bind to the native cytokine. In preferred embodiments, knowledge of the structure of the cytokine/receptor complex is used to select amino acid positions for site-directed or error prone mutagenesis. Conveniently a yeast display system can be used for the selection process, although other display and selection methods are also useful.

In some cases, amino acid changes are obtained by affinity maturation. An "affinity matured" polypeptide is one having one or more alteration(s) in one or more residues which results in an improvement in the affinity of the orthologous polypeptide for the cognate orthologous receptor, or vice versa, compared to a parent polypeptide which does not possess those alteration(s). Affinity maturation can be done to increase the binding affinity by at least about 10% to 50-100-150% or more, or from 1 to 5 fold as compared to the "parent" polypeptide.

The engineered orthologous cytokine of the present invention specifically binds to one or more residues or regions in the orthologous receptor but also does not cross-react with the wild-type receptor. Typically, a lack of cross-reactivity means less than about 5% relative competitive inhibition between the molecules when assessed by ELISA and/or FACS analysis using sufficient amounts of the molecules under suitable assay conditions.

In some embodiments of the invention, the orthogonal receptor is a chain of the IL-2 receptor, i.e. a polypeptide selected from interleukin 2 receptor alpha (IL-2Rα; CD25), interleukin 2 receptor beta (IL-2Rβ; CD122), and interleukin 2 receptor gamma (IL-2Rγ; CD132; common gamma chain). In some specific embodiments the orthogonal receptor is CD132, which is involved in signaling from IL-2, IL-4, IL-7 and IL-15. In other specific embodiments, the orthogonal receptor is CD122, which is involved in signaling from IL-2 and IL-15. The orthogonal receptor is usually paired with a counterpart orthogonal cytokine, e.g. IL-2, IL-4, IL-7, IL-15, etc.

In some specific embodiments, the orthogonal receptor is CD122. In some such embodiments, the orthogonal receptor is introduced into a T cell or NK cell that may also express CD25 and/or CD132. Nucleic acid coding sequences and protein compositions of the modified CD122 protein are provided. In the present invention CD122 is engineered to disrupt binding of the native cytokine by substituting an amino acid of the native sequence with a non-native amino acid, or by deletion of a native amino acid, at a position involved in binding to native IL-2. In some embodiments, the amino acid is substituted with a non-conservative change. Positions of interest for substitution or deletion include, without limitation, in human CD122 (hCD122) R41, R42, Q70, K71, T73, T74, V75, S132, H133, Y134, F135, E136, Q214. Positions of interest for substitution or deletion include, without limitation, in mouse CD122 (mCD122) R42, F67, Q71, S72, T74, S75, V76, S133, H134, Y135, I136, E137, R215.

In some embodiments, CD122 is substituted at one or a combination of positions selected from Q71, T74, H134, Y135 in the mouse protein; or Q70, T73, H133, Y134 in the human protein. In some embodiments, the engineered protein comprises amino acid substitutions at mCD122 H134 and Y135; or hCD122 H133 and Y134. In some embodiments the amino acid substitution is to an acidic amino acid, e.g. aspartic acid and/or glutamic acid. Specific amino acid substitutions include, without limitation, mCD122 substitutions Q71Y; T74D; T74Y; H134D, H134E; H134K; Y135F; Y135E; Y135R; and hCD122 changes 070Y; T73D; T73Y; H133D, H133E; H133K; Y134F; Y134E; Y134R. The selection of an orthologous cytokine may vary with the choice of orthologous receptor.

In some embodiments, where the orthologous receptor is CD122, the orthologous cytokine is IL-2, or IL-15. The cytokine can be selected for binding to the orthologous receptor, e.g. by yeast display evolution, error-prone or targeted mutagenesis, and the like. A representative set of selected orthologous sequences is shown in FIG. 6.

In some embodiments, the orthogonal cytokine is IL-2. In some embodiments, one or more of the following amino acid residues are substituted with an amino acid other than that of the native protein, or are deleted at that position: for mouse IL-2 (mIL-2) any one of H27, L28, E29, Q30, M33, D34, Q36, E37, R41, N103; for human IL-2 (hIL-2) any one of Q13, L14, E15, H16, L19, D20, Q22, M23, G27, R81, N88. In some such embodiments, the set of amino acid substitutions are selected from one or more of (for mIL-2) E29, Q30, M33, D34, Q36, and E37; and for hIL-2, E15, H16, L19, D20, Q22, M23, R81.

In some embodiments, the amino acid substitution for mIL-2 is one or more of: [H27W], [L28M, L28W], [E29D, E29T, E29A], [O30N], [M33V, M33I, M33A], [D34L, D34M], [Q36S, Q36T, Q36E, Q36K, Q36E], [E37A, E37W, E37H, E37Y, E37F, E37A, E37Y], [R41K, R415], [N103E, N103O]; and for hIL-2 is one or more of: [O13W], [L14M, L14W], [E15D, E15T, E15A, E15S], [H16N, H16Q], [L19V, L19I, L19A], [D20L, D20M], [Q22S, Q22T, Q22E, Q22K, Q22E], [M23A, M23W, M23H, M23Y, M23F, M23Q, M23Y], [G27K, G27S], [R81 D, R81Y], [N88E, N88Q], [T51 I]. In some embodiments the set of amino acid substitutions comprises one of the following sets of substitutions for mIL-2: [Q30N, M33V, D34N, Q36T, E37H, R41 K]; [E29D, Q30N, M33V, D34L, 036T, E37H]; [E29D, Q30N, M33V, D34L, Q36T, E37A], and [E29D, Q30N, M33V, D34L, Q36K, E37A] and for hIL-2: [H16N, L19V, D20N, Q22T, M23H, G27K]; [E15D, H16N, L19V, D20L, Q22T, M23H]; [E15D, H16N, L19V, D20L, Q22T, M23A], and [E15D, H16N, L19V, D20L, Q22K, M23A]; or a conservative variant thereof.

In some embodiments the amino acid substitution for hIL-2 is one or more of: [E15S, E15T, E150, E15H]; [H16Q]; [L19V, L19I]; [D20T, D20S, D20M, D20L]; [Q22K, Q22N]; [M23L, M23S, M23V, M23T]. In some embodiments a consensus set of mutations for hIL-2 is [E15S, H16Q, L19V, D20T/S/M; Q22K; M23L/S]. In some embodiments a consensus set of mutations for hIL-2 is [E15S, H16Q, L19V, D20L, M23 Q/A] and optionally Q22K.

In some embodiments the set of amino acid substitutions comprises one of the following sets of substitutions for hIL-2: [E15S; H16Q; L19V, D20T/S; Q22K, M23L/S]; [E15S; H16Q; L19I; D20S; Q22K; M23L]; [E15S; L19V; D20M; Q22K; M23S]; [E15T; H16Q; L19V; D20S; M23S]; [E15Q; L19V; D20M; Q22K; M23S]; [E15Q; H16Q; L19V; D20T; Q22K; M23V]; [E15H; H16Q; L19I; D20S; Q22K; M23L]; [E15H; H16Q; L19I; D20L; Q22K; M23T]; [L19V; D20M; Q22N; M23S]; [E15S, H16Q, L19V, D20L, M23Q, R81 D, T51I], [E15S, H16Q, L19V, D20L,M23Q, R81Y], [E15S, H16Q, L19V, D20L,Q22K, M23A], [E15S, H16Q, L19V, D20L,M23A].

Methods of Treatment

Methods are provided for enhancing cellular responses, by engineering cells from a recipient or donor by introduction of an orthologous receptor of the invention, and stimulating the orthologous receptor by contacting the engineered cell with the cognate orthologous cytokine. The subject methods include a step of obtaining the targeted cells, e.g. T cells, hematopoietic stem cells, etc., which may be isolated from a biological sample, or may be derived in vitro from a source of progenitor cells. The cells are transduced or transfected with an expression vector comprising a sequence encoding the orthologous receptor, which step may be performed in any suitable culture medium.

In some embodiments, an engineered cell is provided, in which the cell has been modified by introduction of an orthologous receptor of the invention. Any cell can be used for this purpose. In some embodiments the cell is a T cell, including without limitation naïve $CD8^+$ T cells, cytotoxic $CD8^+$ T cells, naïve $CD4^+$ T cells, helper T cells, e.g. $T_H1$, $T_H2$, $T_H9$, $T_H11$, $T_H22$, $T_{FH}$; regulatory T cells, e.g. $T_R1$, natural $T_{Reg}$, inducible $T_{Reg}$; memory T cells, e.g. central memory T cells, effector memory T cells, NKT cells, γδ T cells; etc. In other embodiments the engineered cell is a stem cell, e.g. a hematopoietic stem cell, or an NK cell. In some embodiments the cell is genetically modified in an ex vivo procedure, prior to transfer into a subject. The engineered cell can be provided in a unit dose for therapy, and can be allogeneic, autologous, etc. with respect to an intended recipient.

In some embodiments a vector comprising a coding sequence that encodes the orthogonal receptor is provided, where the coding sequence is operably linked to a promoter active in the desired cell. Various vectors are known in the art and can be used for this purpose, e.g. viral vectors, plasmid vectors, minicircle vectors, which vectors can be integrated into the target cell genome, or can be episomally maintained. The receptor encoding vector may be provided in a kit, combined with a vector encoding an orthologous cytokine that binds to and activates the receptor. In some embodiments the coding sequence for the orthologous cytokine is operably linked to a high expression promoter, and may be optimized for production. In other embodiments, a kit is provided in which the vector encoding the orthologous receptor is provided with a purified composition of the orthologous cytokine, e.g. in a unit dose, packaged for administration to a patient.

In some embodiments a therapeutic method is provided, the method comprising introducing into a recipient in need thereof of an engineered cell population, wherein the cell population has been modified by introduction of a sequence encoding an orthologous receptor of the invention. The cell population may be engineered ex vivo, and is usually autologous or allogeneic with respect to the recipient. In some embodiments, the introduced cell population is contacted with the cognate orthologous cytokine in vivo, following administration of the engineered cells. An advantage of the present invention is a lack of cross-reactivity between the orthologous cytokine and the native receptor.

Where the cells are contacted with the orthologous cytokine in vitro, the cytokine is added to the engineered cells in a dose and for a period of time sufficient to activate signaling from the receptor, which may utilize the native cellular machinery, e.g. accessory proteins, co-receptors, and the like. Any suitable culture medium may be used. The cells thus activated may be used for any desired purpose, including experimental purposes relating to determination of antigen specificity, cytokine profiling, and the like, and for delivery in vivo.

Where the contacting is performed in vivo, an effective dose of engineered cells are infused to the recipient, in combination with or prior to administration of the orthologous cytokine. Dosage and frequency may vary depending on the agent; mode of administration; nature of the cytokine; and the like. It will be understood by one of skill in the art that such guidelines will be adjusted for the individual circumstances. The dosage may also be varied for localized administration, e.g. intranasal, inhalation, etc., or for systemic administration, e.g. i.m., i.p., i.v., and the like. Generally at least about $10^4$ engineered cells/kg are administered, at least about $10^5$ engineered cells/kg; at least about $10^6$ engineered cells/kg, at least about $10^7$ engineered cells/kg, or more.

Where the engineered cells are T cells, an enhanced immune response may be manifest as an increase in the cytolytic response of T cells towards the target cells present in the recipient, e.g. towards elimination of tumor cells, infected cells; decrease in symptoms of autoimmune disease; and the like.

Cellular Compositions. Engineered T cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bollus or slow drip), intraarterial, intraperitoneal, intrathecal or subcutaneous administration.

The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Kits

Also provided are kits for use in the methods. The subject kits include an expression vector encoding an orthologous cytokine receptor, or a cell comprising the expression vector. Kits may further comprise the cognate orthologous cytokine. In some embodiments, the components are provided in a dosage form (e.g., a therapeutically effective dosage form), in liquid or solid form in any convenient packaging (e.g., stick pack, dose pack, etc.). Reagents for the selection or in vitro derivation of cells may also be provided, e.g. growth factors, differentiation agents, tissue culture reagents; and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

In some embodiments the subject compositions, methods and kits are used to enhance a T cell mediated immune response. In some embodiments the immune response is directed towards a condition where it is desirable to deplete or regulate target cells, e.g., cancer cells, infected cells, immune cells involved in autoimmune disease, etc.

In some embodiments the condition is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, SIV, etc. Hepatitis B virus, etc. Microbes of interest, but not limited to the following, include: *Yersinia* sp., e.g. *Y. pestis, Y. pseudotuberculosis, Y enterocolitica*; Franciscella sp.; *Pasteurella* sp.; *Vibrio* sp., e.g. *V. cholerae, V. parahemolyticus; Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., Giardia sp., *Toxoplasma* sp., *Leishmania* sp., etc.

An infection treated with the methods of the invention generally involves a pathogen with at least a portion of its life-cycle within a host cell, i.e. an intracellular phase. The methods of the invention provide for a more effective killing of infected cells by the T effector cells of the host organism, relative to removal in the absence of treatment, and thus are directed to the intracellular phase of the pathogen life cycle. The methods may further include monitoring the patient for efficacy of treatment. Monitoring may measure clinical indicia of infection, e.g. fever, white blood cell count, etc., and/or direct monitoring for presence of the pathogen.

Treatment may be combined with other active agents. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

In some embodiments the condition is cancer. The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

The invention now being fully described, it will be apparent to one of ordinary skill in the art that various changes and modifications can be made without departing from the spirit or scope of the invention.

EXPERIMENTAL

Orthologous IL-2 and IL-2Rβ

Here, we describe an invention involving engineered cytokines and receptors that enables selective expansion of desired cell subsets in settings of ex vivo adoptive cell therapy. The specific invention is described for the cytokine interleukin-2 (IL-2) and its receptor the IL-2R β chain (IL-2Rβ), which enables the specific expansion of T cells in adoptive cell therapy, and thus addresses an unmet need in immunotherapy. The approach described herein can be generalized to any setting of adoptive cell therapy where cells are stimulated by a specific receptor-ligand pair, including bone marrow and stem cell transplantation, and many other modalities.

Specifically described are orthogonal IL-2 and IL-2Rβ ligand-receptor pairs. Ortholog versions of IL-2 and ortholog versions of the IL-2Rβ bind specifically to each other, but not their wild-type counterpart. Multiple orthogonal IL-2 variant sequences are provided, with various degrees of affinity for orthogonal 1L-2Rβ. Orthogonal IL-2 dependent signaling and T cell proliferation of T cells engineered to express orthogonal 1L-2Rβ is shown.

IL-2 is an attractive biologic for the treatment of cancer and autoimmunity due to its ability to promote the expansion of effector T cells and regulatory T cells, respectively. However, this pleiotropic nature of IL-2 as well as off target toxicities limit its use in the clinic. The ability to decouple the immunostimulatory and immunoinhibitory properties of IL-2 can provide a superior form of IL-2 immunotherapy.

Demonstrated herein is the ability to engineer T cells to express the orthogonal 1L-2Rβ. These engineered T cells are shown to respond to orthogonal IL-2, resulting in phosphorylation of downstream signal transduction molecules (e.g. STAT5), and T cell proliferation. The activity of orthogonal IL-2 on wild-type T cells is either completely abrogated or significantly blunted compared to the activity wild-type IL-2. Thus, selective T cell expansion using orthogonal IL-2/IL-2 receptor pairs is demonstrated.

Applications of orthogonal IL-2/IL-2 receptor pairs include but are not limited to the selective expansion of tumor reactive cytotoxic T cells for cancer therapy, NK cells for infectious disease and/or cancer, and regulatory T cells for autoimmune disorders.

IL-2 variants with blunted affinity for the intermediate (1L-2Rβ and IL-2Rγ) or high-affinity wild-type IL-2 receptor (IL-2Rα, Rβ, Rγ) due to mutations that disrupt but do not fully ablate binding to IL-2Rβ are also useful for selectively targeting the activity of ortholog IL-2 towards IL-2Rα high cells, e.g. in the treatment of autoimmune disease. IL-2 variants with ablated affinity for the IL-2Rβ chain, but that retain binding to IL-2Rα and therefore act as a competitive antagonist with wild-type IL-2 by inhibiting high-affinity IL-2R formation are useful to treat autoimmunity or graft-v-host disease.

The overall concept of generating and utilizing orthogonal IL-2/IL-2 receptor pairs to control T cell expansion are shown in the schematic of FIG. 1. FIG. 2 provides a work flow, including the steps of generating 1L-2Rβ orthologs that lack binding to wild-type IL-2, using structure guided mutagenesis. Mutations predicted to disrupt 1L-2Rβ binding to wild-type IL-2 are confirmed experimentally using a yeast based screening assay, and are further verified using purified recombinant protein via surface plasmon resonance. Using this approach a number of 1L-2Rβ point mutations that disrupt binding to wild-type IL-2 are described and each of these receptor variants may function as the orthologous receptor. Single point mutations may also be combined with one, two, or more additional point mutations, to generate a larger library of 1L-2Rβ orthologs.

The sequences of orthogonal mouse IL-2Rβ variants are shown in FIG. 3. These mutations may be used as single point mutations, or any combination thereof, to generate IL-2Rβ orthologs with 1, 2, 3, or more point mutations, so long as the combined mutations disrupt wild-type IL-2 binding.

FIG. 4 shows the characterization of a mIL-2Rβ variant comprising the amino acid changes H134D, Y135F, which abrogate wild-type mIL-2 binding. These two residues are known IL-2 interaction hot spots (Ring A et al, Nat Immunol (2012) 13: 1187-95) and we confirmed the mutations disrupt wild-type IL-2 binding via surface plasmon resonance (SPR).

FIG. 5 illustrates the work flow for engineering orthogonal IL-2/IL-2Rβ pairs. An ortholog library is generated of IL-2 that randomizes residues in proximity to or in contact with the IL-2Rβ orthogonal ortholog amino acid residues. Using yeast display, select for IL-2 variants that bind ortholog IL-2Rβ, discard clones that bind wild-type IL-2Rβ. This process may be repeated using site-directed or error prone mutagenesis to generate IL-2 variants with differential binding properties to ortholog but not wild-type IL-2Rβ. Using this approach we generated a library of IL-2 orthologs that: 1) retain binding to the IL-2Rα chain indicating intact structural integrity of the yeast-displayed orthogonal IL-2 variants, 2) bind to the orthogonal IL-2Rβ but, 3) not to the wild-type IL-2 Rβ.

Sequences of characterized orthogonal mouse IL-2 variants are shown in FIG. 6. An alignment of mouse IL-2 and IL-2Rβ and the human counterparts are shown in FIG. 15. These 4 sequences provide a reference for the native, or wild-type sequences. Amino acid residues that were altered to create orthogonal mouse IL-2/IL-2Rβ pairs are mainly conserved in humans. Therefore, the orthogonal mouse IL-2 and IL-2Rβ sequences can be readily translated to the human IL-2 and IL-2Rβ proteins.

As shown in FIG. 7, orthoIL-2 variants bind orthoIL-2Rβ with affinity similar to or greater than the wild-type IL-2 and IL-2Rβ interaction. Soluble orthogonal IL-2 or wild-type IL-2 protein was flowed over a sensor chip coated with wild-type or orthoIL-2Rβ. Binding was determined by surface plasmon resonance (SPR) and curves were fitted using a 1:1 binding model. Shown in FIG. 8, orthoIL-2 variants exhibit blunted activity (phosphoSTAT5) on wild-type CD25 positive and CD25 negative splenocytes.

Generation of orthoIL-2Rβ expressing mouse CTLL-2 T cells is shown in FIG. 9. We created an immortalized mouse T cell line (CTLL-2) that expresses the orthogonal IL-2Rβ (orthoCTLL-2) via lentiviral transduction with of the gene encoding the full length orthogonal receptor. Transduced cells were selected with puromycin, which is toxin to untransduced cells, resulting in a stable CTLL-2 cell line that expresses both the wild-type and orthogonal IL-2Rβ. This cell line is also positive for CD25 and CD132 and thus represents T cells expressing the high-affinity IL-2 receptor complex. The antibody used to detect cell surface IL-2Rβ (CD122) does not discriminate between wild-type and orthoIL-2Rβ. Therefore, the increase in mean fluorescent intensity between wild-type and orthoIL-2Rβ CTLL-2 cells suggests that these cells express the orthogonal receptor. This is further supported by their resistance to puromycin, which is encoded by the same vector used to express the orthoIL-2Rβ.

As shown in FIG. 10, the first set of orthoIL-2 variants are selective for ortho T cells. To interrogate orthogonal IL-2 signaling, we utilized our CTLL-2 cell model, either unmanipulated (wild-type) or transduced to also express the orthogonal IL-2Rβ (ortho). We then determined the ability of wild-type or various orthogonal IL-2 clones to induce phosphorylation of STAT5 (a quantitative readout of IL-2 dependent signal transduction). We identified a number of orthogonal IL-2 variants that induce selective STAT5 phosphorylation on orthogonal IL-2Rβ expressing cells compared to wild-type cells. Dose-response curves for select clones are shown on FIG. 11.

Primary lymph node derived T cells engineered to express orthoIL-2Rβ (H134D Y135F). In addition to our immortalized mouse T cell model, we have also generated orthoIL-2Rβ expressing primary mouse T cells by isolation of mouse lymph node and spleen cells, activation with CD3/CD28, followed by retroviral transduction of the gene encoding the full length orthogonal receptor. This construct also contains an IRES followed by the fluorescent protein YFP, which allows confirmation of transduction by analyzing YFP expression via FACS. The mouse T cells also express the high affinity IL-2 receptor complex (e.g. CD25, CD122, and CD132), shown in FIG. 12

OrthoIL-2 variants induce selective STAT5 phosphorylation on orthoIL-2Rβ expressing primary mouse T cells, shown in FIG. 13.

orthoIL-2 variants that selectively signal through the orthoIL-2Rβ (FIG. 11) also induce selective expansion of CTLL-2 cells expressing the orthoIL-2Rβ compared to wild-type CTLL-2 cells (FIG. 14).

The orthogonal IL-2 engineering approach was also applied to human IL-2 and human IL-2Rβ. We introduced the H133D Y134F mutations that were used to create the mouse orthoIL-2Rβ into human IL-2Rβ, as these residues are highly conserved between mouse and human. Indeed, the wild-type hIL-2Rβ binds yeast-displayed wild-type IL-2, whereas the hIL-2Rβ H133D Y134F mutant (ortho-hIL-2Rβ) lacks detectable binding to wild-type IL-2 (FIG. 15). We created a library of human IL-2 mutants displayed on the surface of yeast by randomizing residues predicted to contact or be in proximity to the H133D Y134F mutations, and selected for IL-2 variants that bound the ortho but not wild-type human IL-2Rβ. This scheme was identical to what was employed to engineer mouse IL-2 orthogonal pairs, and was successful for the human pairs. The strategy is shown in FIG. 16. A consensus set of mutations were identified indicating a convergence of ortho hIL-2 sequences capable of binding the ortho hIL-2Rβ, shown in FIG. 16C.

The polypeptides of the invention are also active in vivo. A mouse model was used to demonstrate selective expansion or increased survival of orthogonal IL-2Rb expressing T cells in mice, shown in FIGS. 17-19. It is shown that orthoIL-2 clone 1G12/149 selectively expands orthogonal but not wild-type T cells in mice. Treatment with wild-type IL-2 results in expansion of both wild-type and ortho T cells compared to a PBS control, whereas treatment with orthoIL-2 clone 1G12/149 selectively expands ortho T cells with limited activity on wild-type T cells.

Example 2

Human IL-2 Orthologs

Materials and Methods

Protein production. DNA encoding wild-type human IL-2 was cloned into the insect expression vector pAcGP67-A, which includes a C-terminal 8xHIS tag for affinity purification. DNA encoding mouse serum albumin (MSA) was purchased from Integrated DNA Technologies (IDT) and cloned into pAcGP67-A as a fusion between the N-terminus of hIL-2 and C-terminus of MSA. Variants of ortho human IL-2 isolated from the activity screen were synthesized as GBlocks (IDT) and cloned into the pAcGP67-A-MSA vector though overlap extension.

Insect expression DNA constructs were transfected into *Trichoplusia ni* (High Five) cells (Invitrogen) using the BaculoGold baculovirus expression system (BD Biosciences) for secretion and purified from the clarified supernatant via Ni-NTA followed by size exclusion chromatography with a Superdex-200 column and formulated in sterile Phosphate Buffer Saline (PBS). Proteins were concentrated and stored at −80° C.

Mammalian expression vectors. Full-length human CD25 was cloned into the lentiviral vector pCDH-CMV-MSC-EF1-Puro (System Biosciences). cDNA encoding full-length human IL-2Rβ was used as a template to clone the full length orthoIL-2Rβ by overlap extension PCR using mutagenic primers that introduce the H133D and Y134F mutations. The resulting PCR product was cloned into the retroviral vector pMSCV-MCS-IRES-YFP.

Cell culture. YT-NK-like cell line was generously provided by Dr. Junji Yodoi, Kyoto University. YT-cells were transduced with the pCDH-CMV-MSC-EF1-Puro-hCD25 lentivirus, and YT cells stably expressing full-length human CD25 (YT+) were selected in 10 μg/mL puromycin. YT+ cells were transduced with retrovirus containing pMSCV-MCS-IRES-YFP-ortho-human-Rβ, and sorted by FACS to enrich the YFP+ (ortho) population to purity. HEK293T cells were generously provided by Dr. Irving Weissman's laboratory at Stanford University. HEK293T cells were maintained in DMEM supplemented with 10% Fetal Bovine Serum (FBS), 1% L-glutamine (L-glu), and 1% penicillin and streptomycin (P/S). YT cells were maintained in RPMI complete (RPMI+GlutaMax+10% FBS, 1% L-Glu, 1% NaPyr, 1% NEAA, 18 mM HEPES and 1% pen/strep).

Lentivirus and Retrovirus production. Lentivirus was produced in HEK293T cells using $3^{rd}$ generation packaging vectors. Briefly, HEK293T cells were seeded at a density of $5\times10^6$ cells per 10 cm tissue culture dish and allowed to adhere for 5-7 hr in complete media (DMEM, 10% FBS, 1% L-Glu, 1% Pen/Strep). Supernatant was removed and replenished with low FBS (5%) DMEM (10 mL) and cells were transfected with a 4:2:1 ratio of pCDH:psPAX2:pMD2G using X-tremeGENE™ HP DNA transfection reagent (Sigma Aldrich) following the manufactures recommendation and cultured overnight at 37° C. in complete media. Media was removed and replenished with 7.5 mL of low FBS DMEM (DMEM, 5% FBS, 1% L-Glu, 1% P/S) and lentivirus was collected from the supernatant 24 and 48 hrs later, pooled, clarified through a 0.45 μm filter, precipitated with PEG-it virus precipitation solution (System Bio), pelleted, re-suspended in complete media at $\frac{1}{100}^{th}$ of the original volume, flash frozen in liquid nitrogen, and stored at −80° C.

Retrovirus was produced in HEK293T cells. Briefly, HEK293T cells were seeded at a density of $5\times10^6$ cells per 10 cm tissue culture dish and allowed to adhere for 5-7 hr in complete media (DMEM, 10% FBS, 1% L-Glu, 1% P/S). Supernatant was removed and replenished with low FBS DMEM (10 mL) and cells were transfected with a 1.5:1 ratio of pMSCV retroviral vector and pCL10A packaging vector (a kind gift of Dr. Melissa McCracken, Stanford University) using X-tremeGENE™ HP following the manufactures recommendation and cultured overnight in low FBS DMEM. Media was removed and replenished with 7.5 mL of low FBS DMEM and cultured for an additional 24 hr. Media was collected, clarified using a 0.45 μm filter, and flash frozen in liquid nitrogen for storage at −80 C. Media was replenished (low FBS DMEM) and cells were cultured for an additional 24 hr and virus was collected and stored as above.

Yeast display of IL-2. Human IL-2 was displayed on the surface of the yeast *S. cerevisiae* strain EBY100 by fusion to the C-terminus of Aga2 using the pCT302 vector harboring a 3C protease cleavage site between the C-terminus of Aga2 and the N-terminus of IL-2 as well as a N-terminal cMyc epitope tag. Briefly, competent EBY100 were electroporated with plasmid encoding yeast-displayed h IL-2 and recovered overnight in SDCAA selection media at 30° C. Transformed yeast were passaged once in SDCAA and yeast cultures in log phase were pelleted and resuspended at an OD 600 of 1.0 in SGCAA induction media containing 10% SDCAA and cultured for 24 hr at 20° C. Surface expression of functional hIL-2 was confirmed by FACS by staining yeast with an Alexa488-labeled anti-cMyc mAb (1:100 dilution; Cell Signaling) and Alexa647-labeled streptavidin (SA) tetramers of wild-type hIL-2Rβ (500 nM SA).

Human IL-2 mutant yeast display library generation.

Site-directed libraries were created by assembly PCR using primers with the following degenerate codons: Library 3 (E15, H16, L19, D20, Q22, M23): (SEQ ID NO:10) 5'-CAAGTTCTACAAAGAAAACACAGCTACAACTGNHKNHKTTACTTNHKNHKT-TANHKNHKATT TTGAATGGAATTAATAATTACAAGAATCCCAAACTC-3' Library 4 (E15, H16, L19, D20, M23, N88): (SEQ ID NO:11) 5'-GTTCTACAAAGAAAACACAGCTACAACTGNHK NHKTACTTNHKNHKTTACAGNHKATTTTGAATGGAATTAATAATTACAAGAATCC-3', (SEQ ID NO:12) 5'-CCCAGGGACTTAATCAGCNHKAT-CAACGTAATAGTTCTGGAACTAAAGGG-3'.

The following primers were used in all libraries: (SEQ ID NO:13) 5'-CGGTAGCGGTGGGGGCGGTTCTCTGGAAGTTCTGTTCCAGGGTCCGAGCGGCGGA-3', (SEQ ID NO:14) 5'-GTAGCTGTGTTTTCTTTGTAGAACTTGAAGTAGGTGCGGATCCGC CGCTCGGACCCTGG-3', (SEQ ID NO:15) 5'-CTAAATGTGAGCATCCTGGTGAGTTT GGGATTCTTGTAATTATTAATTCCATTCAAAAT-3', (SEQ ID NO:16) 5'-CCAGGATGCTCA CATTTAAGTTTTACATGCCCAAGAAGGCCACAG-3', (SEQ ID NO:17) 5'-GAGGTTTGAGTT CTTCTTCTAGACACTGAAGATGTTTCAGTTCTGTGGCCTTCTTGGGC-3', (SEQ ID NO:18) 5'-CAGTGTCTAGAAGAAGAACTCAAACCTCTGGAGGAAGTGCTAAATTTAGCTCAAAGC-3', (SEQ ID NO:19) 5'-GATTAAGTCCCTGGGTCTTAAGTGAAAGTTTTTGCTTTG AGCTAAATT TAGCACTTCCTC-3', (SEQ ID NO:20) 5'-CAGCATATTCACACATGAATGTTGTTTCAGATC CCTTTAGTTCCAGAACTATTACGTTG-3', (SEQ ID NO:21) 5'-GAAACAACATTCATGTGTGAA TATGCT-GATGAGACAGCAACCATTGTAGAATTTCTGAAC-3', (SEQ ID NO:22) 5'-GAGATG ATGCTTTGACAAAAGGTAATC- CATCTGTTCAGAAATTCTACAATGGTTGCTG-3', (SEQ ID NO:23) 5'-GATTACCTTTTGTCAAAGCAT-CATCTCAACACTAACTGCGGCCGCTTCTGGTGG CGAAC-3', (SEQ ID NO:24) 5'-GATCTCGAGCAAGTCTTCTTCGGAGA-TAAGCTTTTGTTC GCCACCAGAAGCGG-3'.

The mutated IL-2 gene PCR product was assembled using Pfu Ultra DNA polymerase (Agilent) and an equal molar mixture of each primer. The product DNA was further PCR-amplified using the primers (SEQ ID NO:25) 5'-CGGTAGCGGTGGGGGCGGTTC-3' and (SEQ ID NO:26) 5'-CGAAGAAGACTTGCTCGAGATC-3' using Phusion DNA polymerase (NEB). The resulting assembled PCR product was gel purified and electroportated with linearized pCT302 vector into EBY-100 yeast to yield a library of ~2×10$^8$ transformants.

Evolution of orthogonal IL-2. Selection of yeast clones that specifically bind the orthoIL-2R were performed using a combination of magnetic activated cell sorting (MACS) and FACS. The first round of selection was performed with 2×10$^9$ yeast, approximately 10 times the library diversity, to ensure 100% coverage of all transformants. The overall strategy employed was to first enrich the library for all full-length h IL-2 variants that bind the orthoIL-2Rβ (Round 1-3) with subsequent rounds using negative selection to remove IL-2 clones that bind wild-type IL-2Rβ and decreasing concentrations of orthoIL-2Rβ to enrich for IL-2 clones that bind the orthoIL-2Rβ with high affinity.

Yeast-based binding and functional screen. Single yeast clones were isolated via culture on SDCAA plates and single colony extraction or single cell FACS both into 96-well round-bottom tissue culture plates containing 100 μL SDCAA and cultured overnight at 30° C. in a shaking incubator. Yeast clones were expanded further in 1.5 mL SDCAA per well of a 96-deep well V-bottom plate for an additional 24 hr at 30° C. prior to induction in SGCAA media containing 10% SDCAA for 72 hr at 20° C. in a shaking incubator at a starting OD 600 of 1.0, also in 1.5 mL and 96-deep well V-bottom plates. Induced yeast were pelleted, washed once with PBS, and resuspended in 200 μL/well of cleavage media (RPMI containing 25 mM HEPES, 0.2 mM TCEP, 20 μg/mL 3C protease) and incubated for 5 min at RT with agitation followed by an overnight incubation at 4° C. without agitation. Yeast were pelleted and the supernatant was clarified through a 96-well 0.45 μm cellulose acetate filter plates (Cat. 7700-2808, GE Heathcare). YT+ (wild-type and ortho expressing) and YT- were plated as described in the IL-2R signaling methods section and 50 μl of clarified yeast supernatant containing mutant IL-2 clones was added, incubated for 20 min at 37° C. and the reaction was terminated and pSTAT5 quantified as described below. The percentage of wild-type or ortho YT cells that are pSTAT5+ was quantified using FlowJo and used to select clones with selective or specific activity on ortho YT+ cells.

Retro viral transduction of human peripheral blood mononuclear cells (PBMCs). Leukoreduction chambers were acquired from the Stanford Blood Center. Blood was drained into a sterile 50 ml conical tube (~7 ml) and PBS+2% FBS was added to 34 ml total. Density gradient medium (15 ml, Ficoll-Paque Plus, GE Healthcare, 17-1440-03) was loaded into two SepMate™-50 tubes (Stemcell, 15450) and 17 ml of diluted cells were gently pipetted on top. The SepMate™ tubes were spun at 1200×g for 15 minutes at room temperature. The top layer, containing the PBMCs, was poured off into a new tube and RPMI was added to 50 ml. The cells were spun at 1200 rpm for 5 minutes to pellet. Pellets were resuspended in 10 ml ACK lysing buffer (Gibco A10492-01) for 4 minutes and quenched to 40 ml with RPMI complete. Cells were pelleted again, suspended in 15 ml of RPMI complete and counted. Cells (1×10$^6$) were plated into each well of a 24 well tissue culture dish, and 25 uL of Dynabeads Human T-Activator CD3/CD28 (Cat #11131 D) and 100U/ml hIL-2 was added to each well. Cells were allowed to activate at 37° C. in incubator for 48 hours.

Activated human PBMCs were transduced via spinfection using un-concentrated retroviral supernatant (~2 mL per well) containing 10 μg/mL polybrene and 100 IU/mL hIL-2 for 1.5 hr at 32° C. and 2500 RPM. The viral supernatant was gently aspirated and replaced with fresh RPMI complete media containing 100 IU/mL hIL-2 and cultured for 24 hr at 37° C. Cells were harvested via gentle pipetting and Dynabeads removed with a magnet. Cells were pelleted via centrifugation, and re-suspended at a density of 1×10$^6$ cells/mL in fresh RPMI complete media containing 100 IU/mL hIL-2 and expanded overnight at 37° C. prior to further downstream cellular assays.

IL-2R signaling via phosphorylation of STAT5. Quantification of IL-2 and orthoIL-2 signal transduction via intracellular pSTAT5 was done. Actively growing YT+ and YT+ ortho cells were pelleted, combined in a 50/50 ratio and plated at a density of 5×10$^5$ cells per well of an ultra-low binding 96-well round bottom plate (Cat. 7007; Costar) in 50 μL warm media. Cells were stimulated by addition of 50 μL media containing serial dilutions of wild-type or ortho IL-2 for 20 min at 37° C., and the reaction was terminated by fixation with 1.5% paraformaldehyde for 10 min at room temperature (RT) with agitation. Cells were pelleted, decanted, and permeabilized with 200 μL of 100% ice-cold methanol for at least 30 min on ice or incubation at −80° C. overnight. Fixed, permeabilized cells were washed three times with FACS buffer and intracellular phosphorylated STAT5 was detected with Alexa647 labeled anti-STAT5 pY694 (BD Biosciences) diluted 1:50 in FACS buffer and incubated for 1 hr at 4 C in the dark. Cells were washed and analyzed on a CytoFLEX equipped with a high-throughput autosampler (Beckman Coulter). Data represent the mean fluorescence intensity and points were fit to a log(agonist) vs. response (three parameters) model using Prism 5 (Graph Pad). All data are presented as mean (n=3) ±SD.

In vitro primary human PBMC proliferation assay. Human peripheral blood monocyte cells containing a mixture of wild-type and ortho transduced T cells were collected by centrifugation, re-suspended in RPMI complete media lacking hIL-2 and seeded at a density of 50,000 cells per/well (in 50 μL) in a 96-well round bottom tissue culture plate (day 1). Cell growth was stimulated by addition of serial dilutions of wild-type or orthoIL-2 (50 μL) to a total volume of 100 μL and cultured for 2 days at 37° C. On day 3, cells were fed fresh cytokine in an additional 100 μL volume and cultured for another 2 days. On day 5, 50 μL of DAPI was added to a final concentration of 0.5 μg/mL and cell counts for each test population were quantified by FACS using the CytoFLEX equipped with a high throughput sampler. The total number of live cells in a set volume was derived after gating for live cells based on FSC and SSC and DAPI negative. Data were analyzed using FlowJo (Tree Star Inc.). Data represent the total live cell count plotted vs. the concentration of cytokine, or as the ratio of ortho cells to total live cells plotted vs the concentration of cytokine. Data are presented as mean (n=4) ±SD.

As shown in FIG. 22, ortho human IL-2 signals through the orthoIL-2R expressed in YT cells in vitro. As shown in FIG. 23, ortho human IL-2 preferentially expands human PBMCs expressing the ortho IL-2R. Human PBMCs were isolated, activated and transformed with retrovirus containing ortho human IL-2Rβ with an IRES YFP (YFP+). Initial ratio of YFP+ cells to total live cells was 20%. 5×10⁵ cells were plated with the indicated concentrations of MSA-human IL-2 or ortho variants MSA-SQVLKAMSA-SQVLqA or MSA-1A1 (black triangles) on day 1, and re-fed the same concentration on day 3. On day 5 the plate was read by flow cytometry. (A) The ratio of YFP+(ortho expressing) cells to total live cells was calculated, and the mean (n=4) ±SD was plotted versus the concentration (left). (B) Total live cell counts (mean (n=4) ±SD) were also plotted versus the cytokine concentration (right). The orthogonal cytokines were did not support as much total cell growth as wild type MSA-hIL-2 at the same concentration, but were selective in strongly expanding the ortho-expressing T cells.

The amino acid substitutions made in the orthogonal hIL-2 proteins are shown below in Table 1.

TABLE 1

| hIL2 | E15 | H16 | L19 | D20 | Q22 | M23 | R81 | Other |
|---|---|---|---|---|---|---|---|---|
| 1A1 (MJH lib 4) | S | Q | V | L |  | Q | D | T51I |
| 1C7 (MJH lib 3) | S | Q | V | L |  | Q | Y |  |
| SQVLKA (design) | S | Q | V | L | K | A |  |  |
| SQVLqA (design) | S | Q | V | L |  | A |  |  |

What is claimed is:

1. A nucleic acid encoding an engineered human IL-2 polypeptide, which comprises amino acid substitutions, numbered relative to reference SEQ ID NO:4:

E15S, E15T, E15Q, or E15H;
H16Q;
L19V or L19I;
D20T, D20S, D20L or D20M; and
M23L, M23S, M23V, M23A, or M23T;
and optionally comprises Q22K, Q22N, R81D, R81Y, T51I or a combination thereof.

2. The nucleic acid of claim 1, wherein the human IL-2 polypeptide comprises amino acid substitution Q22K.

3. The nucleic acid of claim 1, wherein the human IL-2 polypeptide comprises amino acid substitution T51I.

4. The nucleic acid of claim 1, wherein the human IL-2 polypeptide comprises amino acid substitution R81D or R81Y.

5. The nucleic acid of claim 1, wherein the human IL-2 polypeptide comprises amino acid substitutions Q22K and M23A.

6. The nucleic acid of claim 1, wherein the human IL-2 polypeptide comprises amino acid substitutions M23Q, R81D and T51I.

7. The nucleic acid of claim 1, wherein the human IL-2 polypeptide comprises amino acid substitutions M23Q and R81Y.

8. The nucleic acid of claim 1, wherein the human IL-2 polypeptide comprises amino acid substitution M23A.

9. A nucleic acid encoding an engineered human IL-2 polypeptide, which comprises a set of amino acid substitutions, numbered relative to reference SEQ ID NO:4:

E15S;
H16Q;
L19V;
D20L;
M23A; and
Q22K.

10. The nucleic acid of claim 1, wherein the human IL-2 polypeptide comprises a set of amino acid substitutions, numbered relative to reference SEQ ID NO:4:

E15S;
H16Q;
L19V;
D20L;
M23Q;
R81D; and
T51I.

11. The nucleic acid of claim 1, wherein the human IL-2 polypeptide comprises a set of amino acid substitutions, numbered relative to reference SEQ ID NO:4:

E15S;
H16Q;
L19V;
D20L;
M23Q;
and R81Y.

12. The nucleic acid of claim 1, wherein the human IL-2 polypeptide comprises a set of amino acid substitutions, numbered relative to reference SEQ ID NO:4:
E15S;
H16Q;
L19V;
D20L; and
M23A.

13. The nucleic acid of claim 1, wherein the human IL-2 polypeptide is fused to an Fc domain of IgG, or albumin.

14. The nucleic acid of claim 1, wherein the human IL-2 polypeptide binds to and activates an orthogonal human CD122 protein.

15. The nucleic acid of claim 1, wherein the nucleic acid is RNA.

16. The nucleic acid of claim 1, wherein the nucleic acid is DNA.

17. An expression vector comprising the nucleic acid of claim 1.

18. The expression vector of claim 17, wherein the vector is a viral vector.

19. The expression vector of claim 17, wherein the vector is a plasmid vector.

20. The expression vector of claim 17, wherein the vector is an integrating vector.

21. A cell genetically engineered to comprise the nucleic acid of claim 1.

22. The nucleic acid of claim 9, wherein the human IL-2 polypeptide binds to and activates an orthogonal human CD122 protein.

23. The nucleic acid of claim 22, wherein the nucleic acid is RNA.

24. The nucleic acid of claim 22, wherein the nucleic acid is DNA.

25. An expression vector comprising the nucleic acid of claim 22.

26. The expression vector of claim 25, wherein the vector is a viral vector.

27. The expression vector of claim 25, wherein the vector is a plasmid vector.

28. The expression vector of claim 25, wherein the vector is an integrating vector.

29. A cell genetically engineered to comprise the nucleic acid of claim 9.

* * * * *